(12) United States Patent
Lim et al.

(10) Patent No.: US 12,358,930 B2
(45) Date of Patent: Jul. 15, 2025

(54) COMPOUND AND SENSOR AND SENSOR EMBEDDED DISPLAY PANEL AND ELECTRONIC DEVICE

(71) Applicant: Samsung Electronics Co., Ltd., Suwon-si (KR)

(72) Inventors: Youn Hee Lim, Suwon-si (KR); Taejin Choi, Suwon-si (KR); Feifei Fang, Suwon-si (KR); Jeoungin Yi, Seoul (KR); Kyung Bae Park, Hwaseong-si (KR); Sung Young Yun, Suwon-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 602 days.

(21) Appl. No.: 17/839,751

(22) Filed: Jun. 14, 2022

(65) Prior Publication Data
US 2023/0192721 A1 Jun. 22, 2023

(30) Foreign Application Priority Data
Dec. 20, 2021 (KR) ........................ 10-2021-0182833

(51) Int. Cl.
*C07D 517/16* (2006.01)
*C07D 471/06* (2006.01)
(Continued)

(52) U.S. Cl.
CPC ......... *C07D 517/16* (2013.01); *C07D 471/06* (2013.01); *H10K 50/125* (2023.02); *H10K 71/16* (2023.02); *H10K 71/30* (2023.02); *H10K 85/654* (2023.02); *H10K 85/657* (2023.02); *H10K 2102/361* (2023.02)

(58) Field of Classification Search
None
See application file for complete search history.

(56) References Cited

U.S. PATENT DOCUMENTS 8,525,577 B2 9/2013 Yofu et al.
9,818,956 B2 11/2017 Ro et al.
(Continued)

FOREIGN PATENT DOCUMENTS

KR 10-2016-0052448 A 5/2016
KR 10-2016-0062708 A 6/2016
(Continued)

*Primary Examiner* — Anthony Ho
(74) *Attorney, Agent, or Firm* — Harness, Dickey & Pierce, P.L.C.

(57) ABSTRACT

A compound represented by Chemical Formula 1, a sensor including the compound, a sensor-embedded display panel including the compound, and an electronic device including the compound.

[Chemical Formula 1]

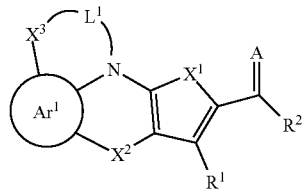

In Chemical Formula 1, $X^1$, $X^2$, $X^3$, $Ar^1$, $L^1$, $A$, $R^1$, and $R^2$ are the same as in the specification.

20 Claims, 13 Drawing Sheets

(51) Int. Cl.
   *H10K 50/125* (2023.01)
   *H10K 71/16* (2023.01)
   *H10K 71/30* (2023.01)
   *H10K 85/60* (2023.01)
   *H10K 102/00* (2023.01)

(56) References Cited

U.S. PATENT DOCUMENTS

| | | |
|---|---|---|
| 9,960,362 B2 | 5/2018 | Bulliard et al. |
| 10,290,812 B2 | 5/2019 | Lim et al. |
| 10,326,083 B2 | 6/2019 | Yagi et al. |
| 10,461,256 B2 | 10/2019 | Choi et al. |
| 10,566,544 B2 | 2/2020 | Shibuya et al. |
| 11,145,822 B2 | 10/2021 | Shin et al. |
| 2021/0234103 A1 | 7/2021 | Lim et al. |
| 2022/0073542 A1 | 3/2022 | Kim et al. |

FOREIGN PATENT DOCUMENTS

| | | |
|---|---|---|
| KR | 10-2017-0114839 A | 10/2017 |
| KR | 10-2017-0126753 A | 11/2017 |
| KR | 10-2017-0135449 A | 12/2017 |
| KR | 10-2017-0137648 A | 12/2017 |
| KR | 10-2019-0044555 A | 4/2019 |
| KR | 10-2021-0091064 A | 7/2021 |
| KR | 10-2022-0028957 A | 3/2022 |
| WO | WO-2010/115184 A2 | 10/2010 |

COMPOUND AND SENSOR AND SENSOR EMBEDDED DISPLAY PANEL AND ELECTRONIC DEVICE

CROSS-REFERENCE TO RELATED APPLICATION

This application claims priority to and the benefit of, under 35 U.S.C. § 119, Korean Patent Application No. 10-2021-0182833 filed in the Korean Intellectual Property Office on Dec. 20, 2021, the entire contents of which are incorporated herein by reference.

BACKGROUND

1. Field

Compounds, sensors, sensor-embedded display panels, and electronic devices are disclosed.

2. Description of the Related Art

Recently, there is an increasing demand for a display device implementing a biometric recognition technology that authenticates the person by extracting specific biometric information or behavioral characteristic information of a person with an automated device centering on finance, healthcare, and mobile. Accordingly, the display device may include a sensor for biometric recognition.

On the other hand, such a sensor for biometric recognition may be divided into an electrostatic type, an ultrasonic type, or an optical type. Among them, the optical type sensor is a sensor configured to absorb light and convert the absorbed light into an electrical signal. The organic material has a large extinction coefficient and may be configured to selectively absorb light in a specific wavelength region according to a molecular structure, and thus it may be usefully applied to an optical type sensor.

SUMMARY

The sensor provided in the display device may be disposed under the display panel or may be manufactured as a separate module and mounted on the outside of the display panel. However, when the sensor is disposed under the display panel, the object should be recognized through the display panel, various films, and/or parts, and thus performance may be degraded. When the sensor is separately manufactured and mounted as a separate module, there are limitations in terms of design and usability. Accordingly, an embedded sensor including a sensor embedded in the display panel may be proposed. However, since the performance and physical properties required for the display panel and the sensor are different from each other, it is difficult to implement in an integrated form.

Some example embodiments provide a compound that may be effectively applied to a sensor.

Some example embodiments provide a sensor including the compound.

Some example embodiments provide a sensor-embedded display panel including the compound or the sensor.

Some example embodiments provide an electronic device including the compound, the sensor, or the sensor-embedded display panel.

According to some example embodiments, a compound represented by Chemical Formula 1 is provided.

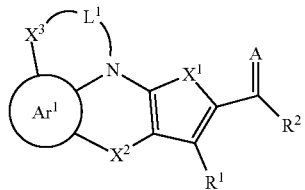

[Chemical Formula 1]

In Chemical Formula 1, $X^1$ is Se, Te, SO, $SO_2$, $NR^a$, $BR^b$, $CR^cR^d$, $SiR^eR^f$, or $GeR^gR^h$, $Ar^1$ is a substituted or unsubstituted C6 to C30 aromatic ring, a substituted or unsubstituted C2 to C30 heteroaromatic ring, or a fused ring thereof, $X^2$ and $X^3$ are each independently O, S, Se, Te, SO, $SO_2$, $NR^i$, $BR^j$, $CR^kR^l$, $SiR^mR^n$, or $GeR^oR^p$, $L^1$ is $(CR^3R^4)_n$ or $R^5C{=}CR^6$, wherein n is an integer of 1 to 3, A is a cyclic group including $C{=}Z^1$, a halogen, a C1 to C30 haloalkyl group, a cyano group, a dicyanovinyl group, or any combination thereof, wherein $Z^1$ is O, S, Se, Te, or $CR^qR^r$, $R^q$ and $R^r$ are each independently hydrogen, a substituted or unsubstituted C1 to C20 alkyl group, a carbonyl group, a cyano group, a dicyanovinyl group, or any combination thereof, and $R^q$ and $R^r$ are each independently present or linked to each other to form a ring, $R^1$ to $R^6$ and $R^a$ to $R^p$ are each independently hydrogen, a substituted or unsubstituted C1 to C20 alkyl group, a substituted or unsubstituted C2 to C30 alkenyl group, a substituted or unsubstituted C1 to C30 alkoxy group, a substituted or unsubstituted C1 to C30 alkylthio group, a substituted or unsubstituted C6 to C30 aryl group, a substituted or unsubstituted C3 to C30 heterocyclic group, a halogen, a cyano group, or any combination thereof, and $R^1$ to $R^6$ and $R^a$ to $R^p$ are each independently present or adjacent two of $R^1$ to $R^6$ and $R^a$ to $R^p$ are linked to each other to form a ring.

$Ar^1$ may be a substituted or unsubstituted benzene, a substituted or unsubstituted naphthalene, a substituted or unsubstituted anthracene, a substituted or unsubstituted phenanthrene, a substituted or unsubstituted tetracene, a substituted or unsubstituted furan, a substituted or unsubstituted thiophene, a substituted or unsubstituted selenophene, a substituted or unsubstituted tellurophene, or a fused ring of two or more therefrom.

At least one of $X^2$ or $X^3$ may be $CR^kR^l$, $SiR^mR^n$, or $GeR^oR^p$, wherein $R^k$ to $R^p$ may each independently be hydrogen, a substituted or unsubstituted C1 to C20 alkyl group, a substituted or unsubstituted C2 to C30 alkenyl group, a substituted or unsubstituted C1 to C30 alkoxy group, a substituted or unsubstituted C1 to C30 alkylthio group, a substituted or unsubstituted C6 to C30 aryl group, a substituted or unsubstituted C3 to C30 heterocyclic group, a halogen, a cyano group, or any combination thereof.

A may be a cyclic group represented by any one of Chemical Formulas 1A to 1E.

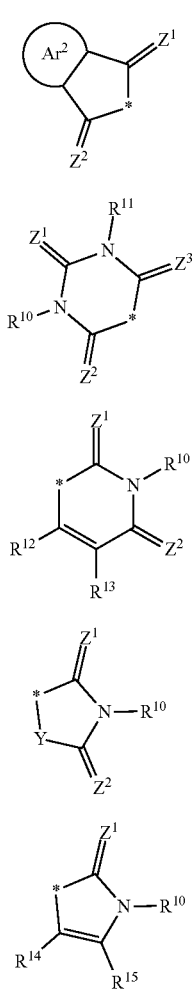

[Chemical Formula 1A]

[Chemical Formula 1B]

[Chemical Formula 1C]

[Chemical Formula 1D]

[Chemical Formula 1E]

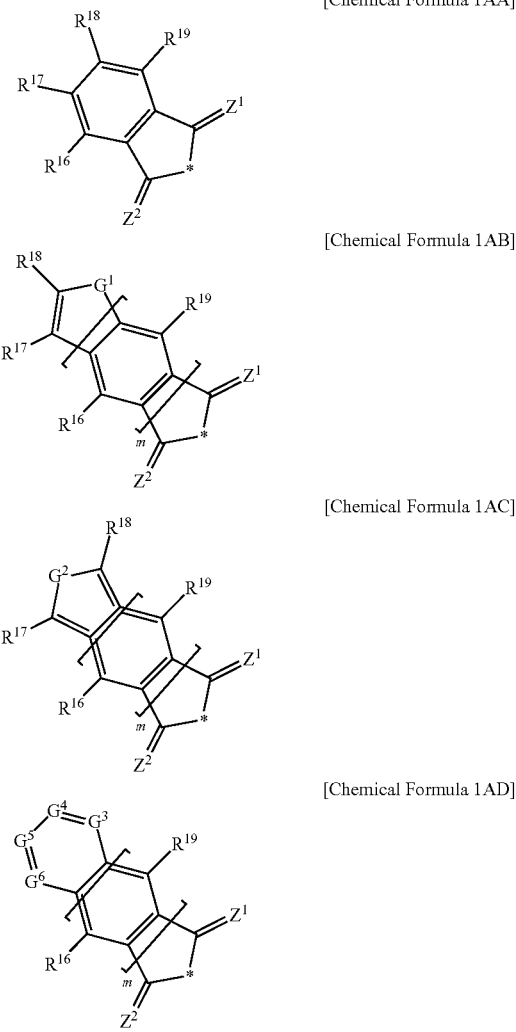

[Chemical Formula 1AA]

[Chemical Formula 1AB]

[Chemical Formula 1AC]

[Chemical Formula 1AD]

In Chemical Formulas 1A to 1E, $Ar^2$ is a substituted or unsubstituted C6 to C30 arylene group, a substituted or unsubstituted C3 to C30 cycloalkylene group, a substituted or unsubstituted C3 to C30 cycloalkenylene group, a substituted or unsubstituted C2 to C30 heterocyclic group, or a fused ring thereof, $Z^1$ to $Z^3$ are each independently O, S, Se, Te or $CR^qR^r$, wherein $R^q$ and $R^r$ are each independently hydrogen, a substituted or unsubstituted C1 to C20 alkyl group, a carbonyl group, a cyano group, a dicyanovinyl group, or any combination thereof, and $R^q$ and $R^r$ are each independently present or linked to each other to form a ring, Y is O, S, Se, or Te, $R^{10}$ to $R^{15}$ are each independently hydrogen, a substituted or unsubstituted C1 to C20 alkyl group, a substituted or unsubstituted C2 to C30 alkenyl group, a substituted or unsubstituted C1 to C30 alkoxy group, a substituted or unsubstituted C1 to C30 alkylthio group, a substituted or unsubstituted C6 to C30 aryl group, a substituted or unsubstituted C3 to C30 heterocyclic group, a halogen, a cyano group, or any combination thereof, $R^{10}$ to $R^{15}$ are each independently present or adjacent two of $R^{10}$ to $R^{15}$ are linked to each other to form a ring, and

* is a linking point with Chemical Formula 1.

The cyclic group represented by Chemical Formula 1A may be a cyclic group represented by any one of Chemical Formulas 1AA to 1AD.

In Chemical Formulas 1AA to 1AD, $Z^1$ and $Z^2$ are each independently O, S, Se, Te or $CR^qR^r$, wherein $R^q$ and $R^r$ are each independently hydrogen, a substituted or unsubstituted C1 to C20 alkyl group, a carbonyl group, a cyano group, a dicyanovinyl group, or any combination thereof, and $R^q$ and $R^r$ are each independently present or linked to each other to form a ring, $G^1$ and $G^2$ are each independently O, S, Se, or Te, $G^3$ to $G^6$ are each independently N or $CR^{20}$, $R^{16}$ to $R^{20}$ are each independently hydrogen, a substituted or unsubstituted C1 to C20 alkyl group, a substituted or unsubstituted C2 to C30 alkenyl group, a substituted or unsubstituted C1 to C30 alkoxy group, a substituted or unsubstituted C1 to C30 alkylthio group, a substituted or unsubstituted C6 to C30 aryl group, a substituted or unsubstituted C3 to C30 heterocyclic group, a halogen, a cyano group, or any combination thereof, $R^{16}$ to $R^{20}$ are each independently present or adjacent two of $R^{16}$ to $R^{20}$ are linked to each other to form a ring, m is an integer of 0 to 2, and

* is a linking point with Chemical Formula 1.

The compound may be represented by Chemical Formula 2 or 3.

[Chemical Formula 2]

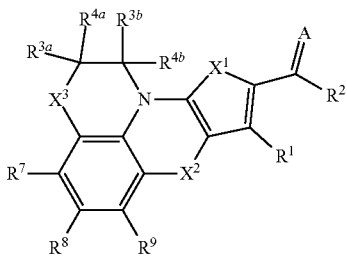

[Chemical Formula 3]

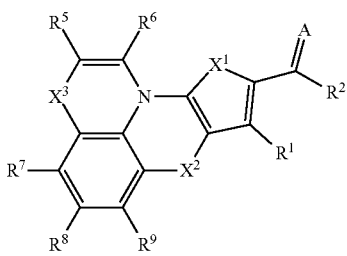

[Chemical Formula 1-1]

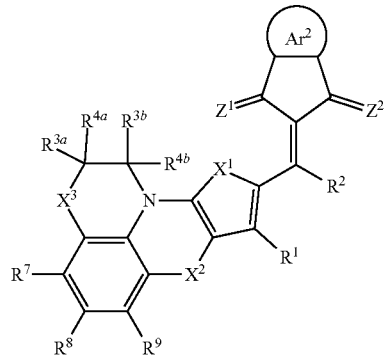

[Chemical Formula 1-2]

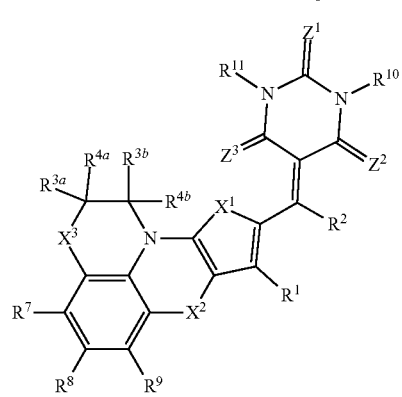

[Chemical Formula 1-3]

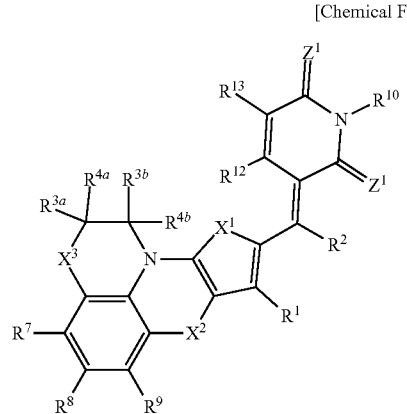

[Chemical Formula 1-4]

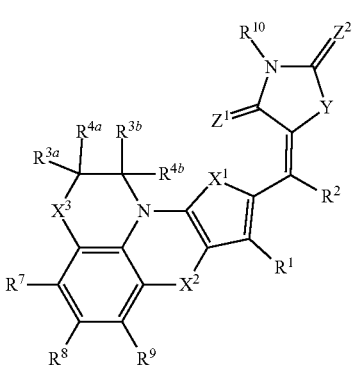

In Chemical Formula 2 or 3, $X^1$ is Se, Te, SO, $SO_2$, $NR^a$, $BR^b$, $CR^cR^d$, $SiR^eR^f$, or $GeR^gR^h$, $X^2$ and $X^3$ are each independently O, S, Se, Te, SO, $SO_2$, $NR^i$, $BR^j$, $CR^kR^l$, $SiR^mR^n$, or $GeR^oR^p$, A is a cyclic group including $C=Z^1$, a halogen, a C1 to C30 haloalkyl group, a cyano group, a dicyanovinyl group, or any combination thereof, wherein $Z^1$ is O, S, Se, Te, or $CR^qR^r$, $R^q$ and $R^r$ are each independently hydrogen, a substituted or unsubstituted C1 to C20 alkyl group, a carbonyl group, a cyano group, a dicyanovinyl group, or any combination thereof, and $R^q$ and $R^r$ are each independently present or linked to each other to form a ring, $R^1$, $R^2$, $R^{3a}$, $R^{3b}$, $R^{4a}$, $R^{4b}$, $R^5$ to $R^9$, and $R^a$ to $R^p$ are each independently hydrogen, a substituted or unsubstituted C1 to C20 alkyl group, a substituted or unsubstituted C2 to C30 alkenyl group, a substituted or unsubstituted C1 to C30 alkoxy group, a substituted or unsubstituted C1 to C30 alkylthio group, a substituted or unsubstituted C6 to C30 aryl group, a substituted or unsubstituted C3 to C30 heterocyclic group, a halogen, a cyano group, or any combination thereof, and $R^1$, $R^2$, $R^{3a}$, $R^{3b}$, $R^{4a}$, $R^{4b}$, $R^5$ to $R^9$, and $R^a$ to $R^p$ are each independently present or adjacent two of $R^1$, $R^2$, $R^{3a}$, $R^{3b}$, $R^{4a}$, $R^{4b}$, $R^5$ to $R^9$, and $R^a$ to $R^p$ are linked to each other to form a ring.

The compound may be represented by any one of the following Chemical Formulas 1-1 to 1-5.

-continued

[Chemical Formula 1-5]

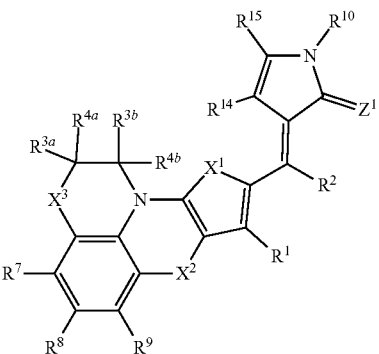

In Chemical Formulas 1-1 to 1-5, $X^1$ is Se, Te, SO, $SO_2$, $NR^a$, $BR^b$, $CR^cR^d$, $SiR^eR^f$, or $GeR^gR^h$, $X^2$ and $X^3$ are each independently O, S, Se, Te, SO, $SO_2$, $NR^i$, $BR^j$, $CR^kR^l$, $SiR^mR^n$, or $GeR^oR^p$, $Ar^2$ is a substituted or unsubstituted C6 to C30 arylene group, a substituted or unsubstituted C3 to C30 cycloalkylene group, a substituted or unsubstituted C3 to C30 cycloalkenylene group, a substituted or unsubstituted C2 to C30 heterocyclic group, or a fused ring thereof, $Z^1$ to $Z^3$ are each independently O, S, Se, Te, or $CR^qR^r$, wherein $R^q$ and $R^r$ are each independently hydrogen, a substituted or unsubstituted C1 to C20 alkyl group, a carbonyl group, a cyano group, a dicyanovinyl group, or any combination thereof, and $R^q$ and $R^r$ are each independently present or linked to each other to form a ring, Y is O, S, Se, or Te, $R^1$, $R^2$, $R^{3a}$, $R^{3b}$, $R^{4a}$, $R^{4b}$, $R^7$ to $R^{15}$ and $R^a$ to $R^p$ are each independently hydrogen, a substituted or unsubstituted C1 to C20 alkyl group, a substituted or unsubstituted C2 to C30 alkenyl group, a substituted or unsubstituted C1 to C30 alkoxy group, a substituted or unsubstituted C1 to C30 alkylthio group, a substituted or unsubstituted C6 to C30 aryl group, a substituted or unsubstituted C3 to C30 heterocyclic group, a halogen, a cyano group, or any combination thereof, and $R^1$, $R^2$, $R^{3a}$, $R^{3b}$, $R^{4a}$, $R^{4b}$, $R^7$ to $R^{15}$, and $R^a$ to $R^p$ are each independently present or adjacent two of $R^1$, $R^2$, $R^{3a}$, $R^{3b}$, $R^{4a}$, $R^{4b}$, $R^7$ to $R^{15}$, and $R^a$ to $R^p$ are linked to each other to form a ring.

According to some example embodiments, a sensor includes a first electrode, a second electrode, and a photoelectric conversion layer between the first electrode and the second electrode and including the compound.

The compound may be a p-type semiconductor, and the photoelectric conversion layer may further include an n-type semiconductor forming a pn junction with the compound.

According to some example embodiments, a sensor-embedded display panel includes a substrate, a light emitting element on the substrate and including a light emitting layer, and a light absorption sensor on the substrate and including a photoelectric conversion layer, wherein the light emitting element and the light absorption sensor are arranged in parallel along an in-plane direction of the substrate such that the light absorption sensor and the light emitting element at least partially overlap in the in-plane direction, and the photoelectric conversion layer includes the compound.

The light emitting element may include first, second, and third light emitting elements, the first, second, and third light emitting elements configured to emit light of different wavelength spectrum in relation to each other, and the light absorption sensor may be configured to absorb light that is emitted from at least one of the first, second, or third light emitting elements and then reflected by the recognition target, and convert it into an electrical signal.

The compound may be a p-type semiconductor, the photoelectric conversion layer may further include an n-type semiconductor forming a pn junction with the compound, and a difference between sublimation temperatures of the p-type semiconductor and the n-type semiconductor is less than or equal to 150° C., wherein each sublimation temperature of a given semiconductor of the p-type semiconductor or the n-type semiconductor is a temperature at which a weight loss of the given semiconductor of 10% compared to an initial weight of the given semiconductor occurs during thermogravimetric analysis of the given semiconductor at an ambient pressure of 10 Pa or less.

The sublimation temperatures of the p-type semiconductor and the n-type semiconductor may be 100° C. to 380° C., respectively.

The p-type semiconductor may be a light absorbing material configured to absorb at least a portion of light in a visible light wavelength spectrum, and the n-type semiconductor may be a transparent semiconductor configured not to substantially absorb light in the visible light wavelength spectrum.

The sensor-embedded display panel may include a common electrode configured to apply a common voltage to the light emitting element and the light absorption sensor.

The sensor-embedded display panel may further include a first common auxiliary layer that is a single piece of material that extends continuously between the light emitting element and the common electrode and between the light absorption sensor and the common electrode, and a second common auxiliary layer that is another single piece of material that extends continuously between the light emitting element and the substrate and between the light absorption sensor and the substrate.

The sensor-embedded display panel may include a display area configured to display a color and a non-display area excluding the display area, and the light absorption sensor may be in disposed the non-display area.

The light emitting element may include a first light emitting element configured to emit light of a red wavelength spectrum, a second light emitting element configured to emit light of a green wavelength spectrum, and a third light emitting element configured to emit light of a blue emission spectrum, the display area may include a plurality of first subpixels configured to display red and including the first light emitting element, a plurality of second subpixels configured to display green and including the second light emitting element, and a plurality of third subpixels configured to display blue and including the third light emitting element, and the light absorption sensor may be between at least two subpixels of a first subpixel of the plurality of first subpixels, a second subpixel of the plurality of second subpixels, or a third subpixel of the plurality of third subpixels.

According to some example embodiments, an electronic device including the sensor or the sensor-embedded display panel is provided.

The compound may have good optical and electrical properties and may be effectively applied to a sensor and a sensor-embedded display panel.

DETAILED DESCRIPTION

Figure 1:
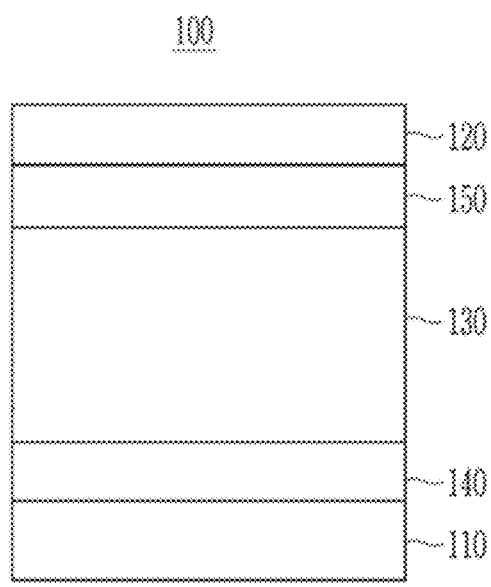
FIG. 1 is a cross-sectional view showing an example of a sensor according to some example embodiments.

Hereinafter, example embodiments will be described in detail so that a person skilled in the art would understand the same. However, a structure that is actually applied may be implemented in various different forms and is not limited to the embodiments described herein.

In the drawings, the thickness of layers, films, panels, regions, etc., are exaggerated for clarity. It will be understood that when an element such as a layer, film, region, or substrate is referred to as being "on" another element, it may be directly on the other element or intervening elements may also be present. In contrast, when an element is referred to as being "directly on" another element, there are no intervening elements present.

In the drawings, parts having no relationship with the description are omitted for clarity of the embodiments, and the same or similar constituent elements are indicated by the same reference numeral throughout the specification.

Hereinafter, the terms "lower" and "upper" are used for better understanding and ease of description, but do not limit the location relationship.

As used herein, when a definition is not otherwise provided, "substituted" refers to replacement of hydrogen of a compound by a substituent of a halogen, a hydroxy group, a nitro group, a cyano group, an amino group, an azido group, an amidino group, a hydrazino group, a hydrazono group, a carbonyl group, a carbamyl group, a thiol group, an ester group, a carboxyl group or a salt thereof, a sulfonic acid group or a salt thereof, a phosphoric acid or a salt thereof, a C1 to C30 alkyl group, a C2 to C30 alkenyl group, a C2 to C30 alkynyl group, a C6 to C30 aryl group, a C7 to C30 arylalkyl group, a C1 to C30 alkoxy group, a C1 to C20 heteroalkyl group, a C3 to C20 heterocyclic group, a C3 to C20 heteroarylalkyl group, a C3 to C30 cycloalkyl group, a C3 to C15 cycloalkenyl group, a C6 to C15 cycloalkynyl group, a C3 to C30 heterocycloalkyl group, or any combination thereof.

As used herein, when a definition is not otherwise provided, "hetero" refers to one including 1 to 4 heteroatoms of N, O, S, Se, Te, Si, or P.

As used herein, when a definition is not otherwise provided, "alkyl group" may be a linear or branched saturated monovalent hydrocarbon group (e.g., a methyl group, an ethyl group, a propyl group, an isobutyl group, a sec-butyl group, a tert-butyl group, a pentyl group, an iso-amyl group, a hexyl group, and the like).

As used herein, when a definition is not otherwise provided, "alkenyl group" refers to a linear or branched saturated monovalent hydrocarbon group including at least one carbon-carbon double bond (e.g., an ethenyl group).

As used herein, when a definition is not otherwise provided, "alkoxy group" may refer to an alkyl group that is linked via an oxygen, e.g., a methoxy group, an ethoxy group, and a sec-butyloxy group.

As used herein, when a definition is not otherwise provided, "aryl group" refers to a monovalent functional group formed by the removal of one hydrogen atom from one or more rings of an arene, e.g., phenyl or naphthyl. The arene refers to a hydrocarbon having an aromatic ring, and includes monocyclic and polycyclic hydrocarbons wherein the additional ring(s) of the polycyclic hydrocarbon may be aromatic or nonaromatic.

As used herein, when a definition is not otherwise provided, "heterocyclic group" is a higher concept of a heteroaryl group, and may include at least one heteroatom of N, O, S, Se, Te, P, or Si, and the remaining carbon. When the heterocyclic group is a fused ring, the entire heterocyclic group or each ring may include one or more heteroatoms.

As used herein, when a definition is not otherwise provided, "aromatic ring" refers to a functional group in which all atoms in the cyclic functional group have a p-orbital, and wherein these p-orbitals are conjugated. For example, the aromatic ring may be a C6 to C20 aryl group.

Hereinafter, when a definition is not otherwise provided, the energy level is the highest occupied molecular orbital (HOMO) energy level or the lowest unoccupied molecular orbital (LUMO) energy level.

It will further be understood that when an element is referred to as being "on" another element, it may be above or beneath or adjacent (e.g., horizontally adjacent) to the other element.

It will be understood that elements and/or properties thereof (e.g., structures, surfaces, directions, or the like), which may be referred to as being "perpendicular," "parallel," "coplanar," or the like with regard to other elements and/or properties thereof (e.g., structures, surfaces, directions, or the like) may be "perpendicular," "parallel," "coplanar," or the like or may be "substantially perpendicular," "substantially parallel," "substantially coplanar," respectively, with regard to the other elements and/or properties thereof.

Elements and/or properties thereof (e.g., structures, surfaces, directions, or the like) that are "substantially perpendicular" with regard to other elements and/or properties thereof will be understood to be "perpendicular" with regard to the other elements and/or properties thereof within manufacturing tolerances and/or material tolerances and/or have a deviation in magnitude and/or angle from "perpendicular," or the like with regard to the other elements and/or properties thereof that is equal to or less than 10% (e.g., a. tolerance of ±10%).

Elements and/or properties thereof (e.g., structures, surfaces, directions, or the like) that are "substantially parallel" with regard to other elements and/or properties thereof will be understood to be "parallel" with regard to the other elements and/or properties thereof within manufacturing tolerances and/or material tolerances and/or have a deviation in magnitude and/or angle from "parallel," or the like with regard to the other elements and/or properties thereof that is equal to or less than 10% (e.g., a. tolerance of ±10%).

Elements and/or properties thereof (e.g., structures, surfaces, directions, or the like) that are "substantially coplanar" with regard to other elements and/or properties thereof will be understood to be "coplanar" with regard to the other elements and/or properties thereof within manufacturing tolerances and/or material tolerances and/or have a deviation in magnitude and/or angle from "coplanar," or the like with regard to the other elements and/or properties thereof that is equal to or less than 10% (e.g., a. tolerance of ±10%).

It will be understood that elements and/or properties thereof may be recited herein as being "the same" or "equal" as other elements, and it will be further understood that elements and/or properties thereof recited herein as being "identical" to, "the same" as, or "equal" to other elements may be "identical" to, "the same" as, or "equal" to or "substantially identical" to, "substantially the same" as or "substantially equal" to the other elements and/or properties thereof. Elements and/or properties thereof that are "substantially identical" to, "substantially the same" as or "substantially equal" to other elements and/or properties thereof will be understood to include elements and/or properties thereof that are identical to, the same as, or equal to the other elements and/or properties thereof within manufacturing tolerances and/or material tolerances. Elements and/or properties thereof that are identical or substantially identical to and/or the same or substantially the same as other elements and/or properties thereof may be structurally the same or substantially the same, functionally the same or substantially the same, and/or compositionally the same or substantially the same.

It will be understood that elements and/or properties thereof described herein as being the "substantially" the same and/or identical encompasses elements and/or properties thereof that have a relative difference in magnitude that is equal to or less than 10%. Further, regardless of whether elements and/or properties thereof are modified as "substantially," it will be understood that these elements and/or properties thereof should be construed as including a manufacturing or operational tolerance (e.g., ±10%) around the stated elements and/or properties thereof.

While the term "same," "equal" or "identical" may be used in description of some example embodiments, it should be understood that some imprecisions may exist. Thus, when one element is referred to as being the same as another element, it should be understood that an element or a value is the same as another element within a desired manufacturing or operational tolerance range (e.g., ±10%).

When the terms "about" or "substantially" are used in this specification in connection with a numerical value, it is intended that the associated numerical value includes a manufacturing or operational tolerance (e.g., ±10%) around the stated numerical value. Moreover, when the words "about" and "substantially" are used in connection with geometric shapes, it is intended that precision of the geometric shape is not required but that latitude for the shape is within the scope of the disclosure. Further, regardless of whether numerical values or shapes are modified as "about" or "substantially," it will be understood that these values and shapes should be construed as including a manufacturing or operational tolerance (e.g., ±10%) around the stated numerical values or shapes. When ranges are specified, the range includes all values therebetween such as increments of 0.1%.

Hereinafter, when a definition is not otherwise provided, a work function or an energy level is expressed as an absolute value from a vacuum level. In addition, when the work function or the energy level is referred to be deep, high, or large, it may have a large absolute value based on "0 eV" of the vacuum level while when the work function or the energy level is referred to be shallow, low, or small, it may have a small absolute value based on "0 eV" of the vacuum level. Further, the differences between the work function and/or the energy level may be values obtained by subtracting a small value of the absolute value from a large value of the absolute value.

Hereinafter, when a definition is not otherwise provided, the HOMO energy level may be evaluated with an amount of photoelectrons emitted by energy when irradiating UV light to a thin film using AC-2 (Hitachi) or AC-3 (Riken Keiki Co., Ltd.).

Hereinafter, when a definition is not otherwise provided, the LUMO energy level may be obtained by obtaining a bandgap energy using a UV-Vis spectrometer (Shimadzu Corporation), and then calculating the LUMO energy level from the bandgap energy and the already measured HOMO energy level.

Hereinafter, a compound according to some example embodiments is described.

A compound according to some example embodiments is represented by Chemical Formula 1.

[Chemical Formula 1]

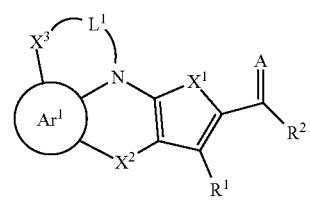

In Chemical Formula 1, $X^1$ is Se, Te, SO, $SO_2$, $NR^a$, $BR^b$, $CR^cR^d$, $SiR^eR^f$, or $GeR^gR^h$, $Ar^1$ is a substituted or unsubstituted C6 to C30 aromatic ring, a substituted or unsubstituted C2 to C30 heteroaromatic ring, or a fused ring thereof, $X^2$ and $X^3$ are each independently O, S, Se, Te, SO, $SO_2$, $NR^i$, $BR^j$, $CR^kR^l$, $SiR^mR^n$, or $GeR^oR^p$, $L^1$ is $(CR^3R^4)_n$ or $R^5C=CR^6$, wherein n is an integer of 1 to 3, A is an electron accepting group, $R^1$ to $R^6$ and $R^a$ to $R^p$ are each independently hydrogen, a substituted or unsubstituted C1 to C20 alkyl group, a substituted or unsubstituted C2 to C30 alkenyl group, a substituted or unsubstituted C1 to C30 alkoxy group, a substituted or unsubstituted C1 to C30 alkylthio group, a substituted or unsubstituted C6 to C30 aryl group, a substituted or unsubstituted C3 to C30 heterocyclic group, a halogen, a cyano group, or any combination thereof, and $R^1$ to $R^6$ and $R^a$ to $R^p$ are each independently present or adjacent two of $R^1$ to $R^6$ and $R^a$ to $R^p$ are linked to each other to form a ring.

The compound represented by Chemical Formula 1 may have a D-A structure in which an electron donating group (D) forming a planar shape by fusion with an $X^1$-containing ring is bonded with an electron accepting group (A) represented by A.

The compound may have a semi-flat shape as a whole by having the structure as described above, and thus may be formed into a high-density thin film due to good molecular stacking during deposition. Since such a high-density thin film may have a high extinction coefficient, light absorption characteristics may be improved.

For example, $X^1$ in Chemical Formula 1 may be Se or Te.

For example, in Chemical Formula 1, $Ar^1$ may be a substituted or unsubstituted benzene, a substituted or unsubstituted naphthalene, a substituted or unsubstituted anthracene, a substituted or unsubstituted phenanthrene, a substituted or unsubstituted tetracene, a substituted or unsubstituted furan, a substituted or unsubstituted thiophene, a substituted or unsubstituted selenophene, a substituted or unsubstituted a substituted or unsubstituted tellurophene, or a fused ring of two or more therefrom.

For example, in Chemical Formula 1, $X^2$ and $X^3$ may be the same as or different from each other, and at least one of $X^2$ or $X^3$ may be $CR^kR^l$, $SiR^mR^n$, or $GeR^oR^p$, where $R^k$ to $R^p$ are each independently hydrogen, a substituted or unsubstituted C1 to C20 alkyl group, a substituted or unsubstituted C2 to C30 alkenyl group, a substituted or unsubstituted C1 to C30 alkoxy group, a substituted or unsubstituted C1 to C30 alkylthio group, a substituted or unsubstituted C6 to C30 aryl group, a substituted or unsubstituted C3 to C30 heterocyclic group, a halogen, a cyano group, or any combination thereof. For example, $X^2$ and $X^3$ may be each $CR^kR^l$, $SiR^mR^n$, or $GeR^oR^p$, and may be each, for example, $CR^kR^l$.

For example, in Chemical Formula 1, $R^1$ and $R^2$ may each independently be hydrogen or a substituted or unsubstituted C1 to C30 alkyl group.

For example, in Chemical Formula 1, A may be a cyclic group including C=$Z^1$, a halogen, a C1 to C30 haloalkyl group, a cyano group, a dicyanovinyl group, or any combination thereof. Herein, $Z^1$ may be O, S, Se, Te, or $CR^qR^r$, wherein $R^q$ and $R^r$ may each independently be hydrogen, a substituted or unsubstituted C1 to C20 alkyl group, a carbonyl group, a cyano group, a dicyanovinyl group, or any combination thereof, and $R^q$ and $R^r$ may each independently be present or may be linked to each other to form a ring.

For example, A may be a cyclic group including C=$Z^1$, and may be, for example, a cyclic group represented by any one of Chemical Formulas 1A to 1E.

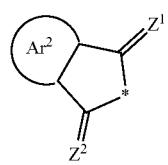

[Chemical Formula 1A]

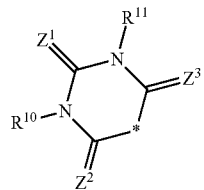

[Chemical Formula 1B]

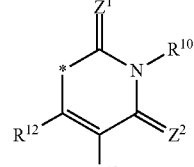

[Chemical Formula 1C]

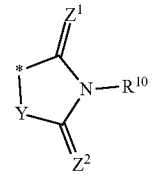

[Chemical Formula 1D]

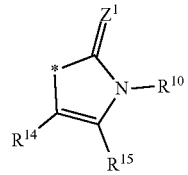

[Chemical Formula 1E]

In Chemical Formulas 1A to 1E, $Ar^2$ may be a substituted or unsubstituted C6 to C30 arylene group, a substituted or unsubstituted C3 to C30 cycloalkylene group, a substituted or unsubstituted C3 to C30 cycloalkenylene group, a substituted or unsubstituted C2 to C30 heterocyclic group, or a fused ring thereof, $Z^1$ to $Z^3$ may each independently be O, S, Se, Te, or $CR^qR^r$, wherein $R^q$ and $R^r$ may each independently be hydrogen, a substituted or unsubstituted C1 to C20 alkyl group, a carbonyl group, a cyano group, a dicyanovinyl group, or any combination thereof, and $R^q$ and $R^r$ may each independently be present or may be linked to each other to form a ring, Y may be O, S, Se, or Te, $R^{10}$ to $R^{15}$ may each independently be hydrogen, a substituted or unsubstituted C1 to C20 alkyl group, a substituted or unsubstituted C2 to C30 alkenyl group, a substituted or unsubstituted C1 to C30 alkoxy group, a substituted or unsubstituted C1 to C30 alkylthio group, a substituted or unsubstituted C6 to C30 aryl group, a substituted or unsubstituted C3 to C30 heterocyclic group, a halogen, a cyano group, or any combination thereof, $R^{10}$ to $R^{15}$ may each independently be present or adjacent two of $R^{10}$ to $R^{15}$ may be linked to each other to form a ring, and

* may be a linking point with Chemical Formula 1.

For example, in Chemical Formula 1A, 1C, or 1D, $Z^1$ and $Z^2$ may be the same as or different from each other, and may each independently be O, S, Se, Te, CH(CN), C(CN)$_2$, or any combination thereof. For example, $Z^1$ and $Z^2$ may be the same as each other, and may be each O. For example, $Z^1$ and $Z^2$ may be the different from each other, and any one of $Z^1$ or $Z^2$ may be O and the other may be Se, Te, CH(CN), or C(CN)$_2$.

For example, in Chemical Formula 1B, $Z^1$, $Z^2$, and $Z^3$ may be the same as or different from each other, and may each independently be O, S, Se, Te, CH(CN), C(CN)$_2$, or any combination thereof. For example, $Z^1$, $Z^2$, and $Z^3$ may be the same as each other, and may be each O. For example, $Z^1$, $Z^2$, and $Z^3$ may be the same as each other, and may be each S. For example, $Z^1$, $Z^2$, and $Z^3$ may be the different from each other, and two of $Z^1$, $Z^2$, and $Z^3$ may be O and the other may be S, Se, Te, CH(CN), or C(CN)$_2$.

For example, $R^{10}$ and $R^{11}$ in Chemical Formula 1B may be the same as or different from each other, and may each independently be hydrogen or a substituted or unsubstituted C1 to C30 alkyl group.

For example, $R^{10}$ and $R^{12}$ to $R^{15}$ in Chemical Formula 1C, 1 D, or 1E may each independently be hydrogen or a substituted or unsubstituted C1 to C30 alkyl group.

For example, the cyclic group represented by Chemical Formula 1A may be a cyclic group represented by any one of Chemical Formulas 1AA to 1AD according to $Ar^2$.

[Chemical Formula 1AA]

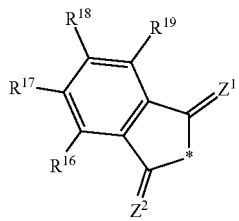

[Chemical Formula 1AB]

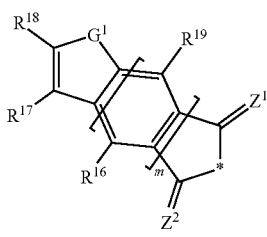

[Chemical Formula 1AC]

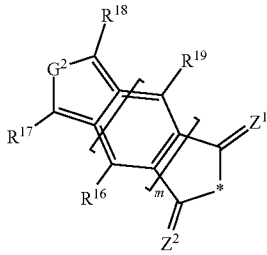

[Chemical Formula 1AD]

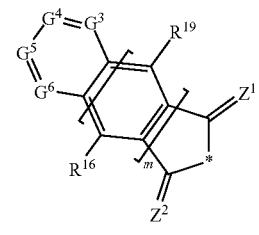

In Chemical Formulas 1AA to 1AD, $Z^1$ and $Z^2$ are the same as described above, for example, $Z^1$ and $Z^2$ are each independently O, S, Se, Te or $CR^qR^r$, wherein $R^q$ and $R^r$ are each independently hydrogen, a substituted or unsubstituted C1 to C20 alkyl group, a carbonyl group, a cyano group, a dicyanovinyl group, or any combination thereof, and $R^q$ and $R^r$ are each independently present or linked to each other to form a ring, $G^1$ and $G^2$ may each independently be O, S, Se, or Te, $G^3$ to $G^6$ may each independently be N or $CR^{20}$, $R^{16}$ to $R^{20}$ may each independently be hydrogen, a substituted or unsubstituted C1 to C20 alkyl group, a substituted or unsubstituted C2 to C30 alkenyl group, a substituted or unsubstituted C1 to C30 alkoxy group, a substituted or unsubstituted C1 to C30 alkylthio group, a substituted or unsubstituted C6 to C30 aryl group, a substituted or unsubstituted C3 to C30 heterocyclic group, a halogen, a cyano group, or any combination thereof, $R^{16}$ to $R^{20}$ may each independently be present or adjacent two of $R^{16}$ to $R^{20}$ may be linked to each other to form a ring, m may be an integer of 0 to 2, and

* may be a linking point with Chemical Formula 1.

For example, the compound represented by Chemical Formula 1 may be represented by Chemical Formula 2 or 3 according to $Ar^1$ and $L^1$.

[Chemical Formula 2]

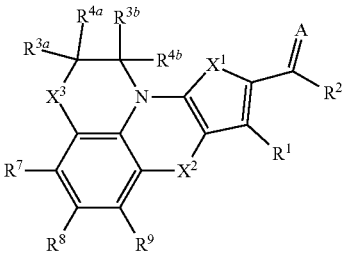

[Chemical Formula 3]

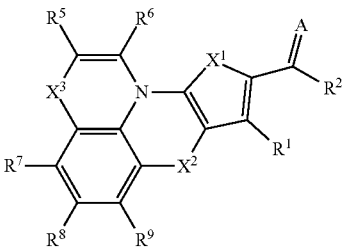

In Chemical Formula 2 or 3, $X^1$, $X^2$, $X^3$, and A are the same as described above, for example, $X^1$ is Se, Te, SO, SO$_2$, NR$^a$, BR$^b$, CR$^c$R$^d$, SiR$^e$R$^f$, or GeR$^g$R$^h$ $X^2$ and $X^3$ are each independently O, S, Se, Te, SO, SO$_2$, NR$^i$, BR$^j$, CR$^k$R$^l$, SiR$^m$R$^n$, or GeR$^o$R$^p$, A is a cyclic group including C=Z$^1$, a halogen, a C1 to C30 haloalkyl group, a cyano group, a dicyanovinyl group, or any combination thereof, wherein $Z^1$ is O, S, Se, Te, or CR$^q$R$^r$, $R^q$ and $R^r$ are each independently hydrogen, a substituted or unsubstituted C1 to C20 alkyl group, a carbonyl group, a cyano group, a dicyanovinyl group, or any combination thereof, and $R^q$ and $R^r$ are each independently present or linked to each other to form a ring, $R^1$, $R^2$, $R^{3a}$, $R^{3b}$, $R^{4a}$, $R^{4b}$, $R^5$ to $R^9$, and $R^a$ to $R^p$ may each independently be hydrogen, a substituted or unsubstituted C1 to C20 alkyl group, a substituted or unsubstituted C2 to C30 alkenyl group, a substituted or unsubstituted C1 to C30 alkoxy group, a substituted or unsubstituted C1 to C30 alkylthio group, a substituted or unsubstituted C6 to C30 aryl group, a substituted or unsubstituted C3 to C30 heterocyclic group, a halogen, a cyano group, or any combination thereof, and R$^1$, R$^2$, R$^{3a}$, R$^{3b}$, R$^{4a}$, R$^{4b}$, R$^5$ to R$^9$, and R$^a$ to R$^p$ may each independently be present or adjacent two of R$^1$, R$^2$, R$^{3a}$, R$^{3b}$, R$^{4a}$, R$^4$,R$^5$ to R$^9$, and R$^a$ to R$^p$ may be linked to each other to form a ring.

For example, the compound represented by Chemical Formula 1 may be represented by any one of Chemical Formulas 1-1 to 1-5 according to Ar$^1$, L$^1$, and A.

[Chemical Formula 1-1]

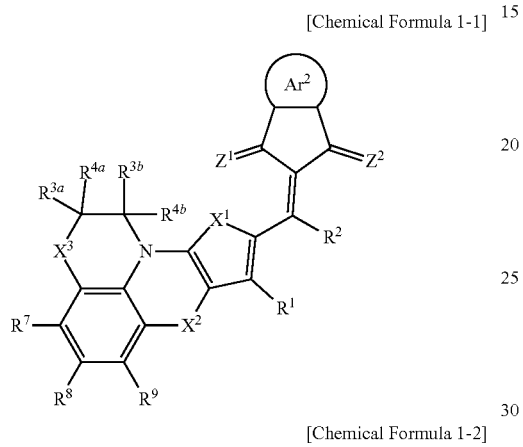

[Chemical Formula 1-2]

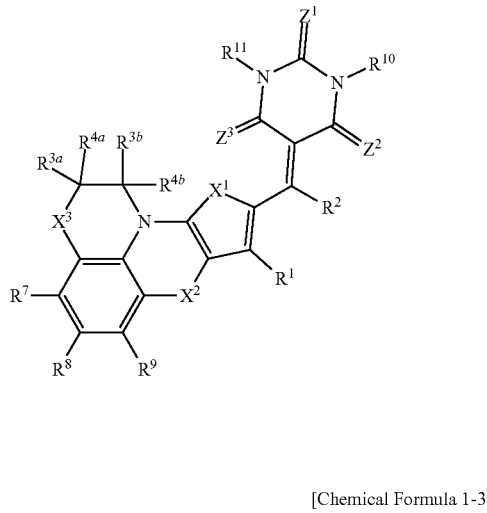

[Chemical Formula 1-3]

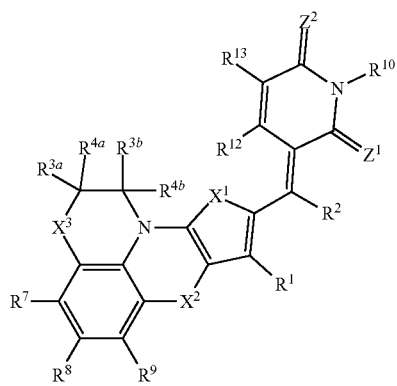

[Chemical Formula 1-4]

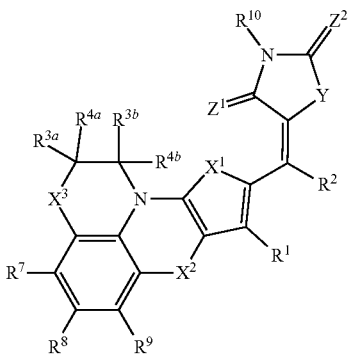

[Chemical Formula 1-5]

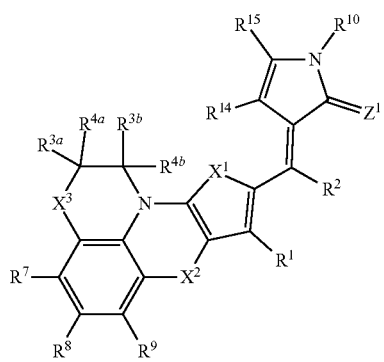

In Chemical Formulas 1-1 to 1-5, X$^1$, X$^2$, X$^3$, Ar$^2$, Z$^1$ to Z$^3$, Y, R$^1$, R$^2$, R$^{3a}$, R$^{3b}$, R$^{4a}$, R$^{4b}$, and R$^7$ to R$^{15}$ are the same as described above. For example, in some example embodiments, in Chemical Formulas 1-1 to 1-5, X$^1$ is Se, Te, SO, SO$_2$, NR$^a$, BR$^b$, CR$^c$R$^d$, SiR$^e$R$^f$, or GeR$^g$R$^h$ X$^2$ and X$^3$ are each independently O, S, Se, Te, SO, SO$_2$, NR$^i$, BR$^j$, CR$^k$R$^l$, SiR$^m$R$^n$, or GeR$^o$R$^p$, Ar$^2$ is a substituted or unsubstituted C6 to C30 arylene group, a substituted or unsubstituted C3 to C30 cycloalkylene group, a substituted or unsubstituted C3 to C30 cycloalkenylene group, a substituted or unsubstituted C2 to C30 heterocyclic group, or a fused ring thereof, Z$^1$ to Z$^3$ are each independently O, S, Se, Te or CR$^q$R$^r$, wherein R$^q$ and R$^r$ are each independently hydrogen, a substituted or unsubstituted C1 to C20 alkyl group, a carbonyl group, a cyano group, a dicyanovinyl group, or any combination thereof, and R$^q$ and R$^r$ are each independently present or linked to each other to form a ring, Y is O, S, Se, or Te, R$^1$, R$^2$, R$^{3a}$, R$^{3b}$, R$^{4a}$, R$^{4b}$, R$^7$ to R$^{15}$, and R$^a$ to R$^p$ are each independently hydrogen, a substituted or unsubstituted C1 to C20 alkyl group, a substituted or unsubstituted C2 to C30 alkenyl group, a substituted or unsubstituted C1 to C30 alkoxy group, a substituted or unsubstituted C1 to C30 alkylthio group, a substituted or unsubstituted C6 to C30 aryl group, a substituted or unsubstituted C3 to C30 heterocyclic group, a halogen, a cyano group, or any combination thereof, and R$^1$, R$^2$, R$^{3a}$, R$^{3b}$, R$^{4a}$, R$^{4b}$, R$^7$ to R$^{15}$, and R$^a$ to R$^p$ are each independently present or adjacent two of R$^1$, R$^2$, R$^{3a}$, R$^{3b}$, R$^{4a}$, R$^{4b}$, R$^7$ to R$^{15}$, and R$^a$ to R$^p$ are linked to each other to form a ring.

The compound may be a photoelectric conversion material, and may be a visible light photoelectric conversion material configured to selectively absorb light of a portion of a visible wavelength spectrum and convert it into an electrical signal. For example, the compound may be configured to selectively absorb light in the green wavelength spectrum among the visible light wavelength spectrum to be photoelectrically converted, and a peak absorption wavelength $\lambda_{peak}$ of the absorption spectrum of the compound may belong to, for example, about 500 nm to about 600 nm, and within the range about 510 nm to about 580 nm, about 520 nm to about 570 nm, about 520 nm to about 560 nm, or about 520 nm to about 550 nm. A full width half maximum FWHM of the absorption spectrum of the compound may be, for example, less than or equal to about 150 nm, and within the above range, about 40 nm to about 150 nm, about 50 nm to about 140 nm, or about 70 nm to about 130 nm. Herein, the FWHM of the absorption spectrum may be a width of a wavelength corresponding to half of the absorption intensity at the absorption peak wavelength.

The compound may have stable thermal properties and may be a sublimable material that may be vacuum-deposited by sublimation without substantial decomposition or polymerization, within a particular (or, alternatively, predetermined) temperature range. The sublimable materials may be identified by thermogravimetric analysis TGA (e.g., TGA of the compound) and may be organic materials that lose a weight with increasing temperature and lose a weight by at least about 10% of their initial weight without substantial decomposition or polymerization.

For example, the compound may have a temperature (hereinafter referred to as a "sublimation temperature") at which a weight loss of 10% relative to the initial weight occurs during thermogravimetric analysis (e.g., thermogravimetric analysis of the compound) at a pressure (e.g., ambient pressure) of about 10 Pa or less (e.g., 0 Pa to about 10 Pa, about 0.01 Pa to about 10 Pa, or the like), within a particular (or, alternatively, predetermined) range. For example, the sublimation temperature of the compound may be less than or equal to about 380° C., and within the above range, less than or equal to about 370° C., less than or equal to about 360° C., less than or equal to about 350° C., less than or equal to about 340° C., less than or equal to about 330° C., less than or equal to about 320° C., less than or equal to about 310° C., less than or equal to about 300° C., less than or equal to about 290° C., less than or equal to about 280° C., less than or equal to about 270° C., or less than or equal to about 250° C., about 100° C. to about 380° C., about 100° C. to about 370° C., about 100° C. to about 360° C., about 100° C. to about 350° C., about 100° C. to about 340° C., about 100° C. to about 330° C., about 100° C. to about 320° C., about 100° C. to about 310° C., about 100° C. to about 300° C., about 100° C. to about 290° C., about 100° C. to about 280° C., about 100° C. to about 270° C., about 100° C. to about 250° C., about 150° C. to about 380° C., about 150° C. to about 370° C., about 150° C. to about 360° C., about 150° C. to about 350° C., about 150° C. to about 340° C., about 150° C. to about 330° C., about 150° C. to about 320° C., about 150° C. to about 310° C., about 150° C. to about 300° C., about 150° C. to about 290° C., about 150° C. to about 280° C., about 150° C. to about 270° C., or about 150° C. to about 250° C.

In addition, the compound may exhibit semiconductor properties by having the electron donating group and the electron accepting group of the aforementioned structure, for example, p-type semiconductor properties. For example, the HOMO energy level of the compound may be about 5.0 eV to about 6.0 eV, and within the above range, about 5.1 eV to about 5.9 eV, about 5.2 eV to about 5.8 eV, or about 5.3 eV to about 5.8 eV. For example, the LUMO energy level of the compound may be about 2.7 to about 4.3 eV, and within the above range, about 2.8 eV to about 4.1 eV or about 3.0 to about 4.0 eV. For example, the bandgap energy of the compound may be about 1.7 eV to about 2.3 eV, and within the above range, about 1.8 eV to about 2.2 eV or about 1.9 eV to about 2.1 eV.

The compound may be applied to various devices due to the aforementioned electrical and thermal properties.

For example, the compound may be applied to a sensor. The sensor may be a light absorption sensor capable of receiving light and converting it into an electrical signal. The sensor may be an organic sensor including the aforementioned compound as a photoelectric conversion material.

FIG. 1 is a cross-sectional view showing an example of a sensor according to some example embodiments.

Referring to FIG. 1, a sensor 100 according to some example embodiments includes a first electrode 110, a second electrode 120, a photoelectric conversion layer 130, and optionally auxiliary layers 140 and 150.

A substrate (not shown) may be disposed below the first electrode 110 or above the second electrode 120. The substrate may be for example an inorganic substrate such as a glass plate or silicon wafer or an organic substrate made of an organic material such as polycarbonate, polymethylmethacrylate, polyethyleneterephthalate, polyethylenenaphthalate, polyamide, polyethersulfone, or any combination thereof. The substrate may be omitted.

The substrate may be, for example, a semiconductor substrate, or a silicon substrate. The semiconductor substrate may include a circuit unit (not shown) including for example circuitry, and the circuit unit (e.g., circuitry) may include transmission transistors (not shown) and/or charge storage (not shown) integrated in the semiconductor substrate. The circuit unit may be electrically connected to the first electrode 110 or the second electrode 120.

One of the first electrode 110 or the second electrode 120 may be an anode and the other may be a cathode. For example, the first electrode 110 may be an anode and the second electrode 120 may be a cathode. For example, the first electrode 110 may be a cathode and the second electrode 120 may be an anode.

At least one of the first electrode 110 or the second electrode 120 may be a light-transmitting electrode. The light-transmitting electrode may be a transparent electrode or a semi-transmissive electrode. The transparent electrode may have a light transmittance of about 85% to 100%, about 90% to 100%, or about 95% to 100% and semi-transmissive electrode may have a light transmittance of greater than or equal to about 30% and less than about 85%, about 40% to about 80%, or about 40% to about 75%. The transparent electrode and the semi-transmissive electrode may include, for example, at least one of an oxide conductor, a carbon conductor, or a metal thin film. The oxide conductors may include, for example, one or more of indium tin oxide (ITO), indium zinc oxide (IZO), zinc tin oxide (ZTO), aluminum tin oxide (ATO), and aluminum zinc oxide (AZO), the carbon conductor may include one or more of graphene and carbon nanostructures, and the metal thin film may be a very thin film including aluminum (Al), magnesium (Mg), silver (Ag), gold (Au), magnesium-silver (Mg—Ag), magnesium-aluminum (Mg—Al), an alloy thereof, or any combination thereof.

Any one of the first electrode 110 or the second electrode 120 may be a reflective electrode. The reflective electrode may include a reflective layer having a light transmittance of about 0% to about 5% and/or a reflectance of about 80% to about 100%, and the reflective layer may include an optically opaque material. The optically opaque material may include a metal, a metal nitride, or any combination thereof, for example silver (Ag), copper (Cu), aluminum (Al), gold (Au), titanium (Ti), chromium (Cr), nickel (Ni), an alloy thereof, a nitride thereof (e.g., TiN), or any combination thereof, but is not limited thereto. The reflective electrode may be formed of (e.g., may comprise) a reflective layer or may have a stacked structure of a reflective layer/transmissive layer or a transmissive layer/reflective layer/transmissive layer, and the reflective layer may be one layer or two or more layers.

For example, each of the first electrode 110 and the second electrode 120 may be a light-transmitting electrode, and any one of the first electrode 110 or the second electrode 120 may be a light-receiving electrode disposed on the light receiving side.

For example, the first electrode 110 may be a light-transmitting electrode, the second electrode 120 may be a reflective electrode, and the first electrode 110 may be a light-receiving electrode.

For example, the first electrode 110 may be a reflective electrode, the second electrode 120 may be a light-transmitting electrode, and the second electrode 120 may be a light-receiving electrode.

The photoelectric conversion layer 130 may be configured to absorb light of at least a portion of a wavelength spectrum and convert the absorbed light into an electrical signal, and for example, may be configured to selectively absorb light in a portion of a visible light wavelength spectrum and convert it into an electrical signal. For example, the photoelectric conversion layer 130 may be configured to selectively absorb light of a green wavelength spectrum and convert it into an electrical signal.

The photoelectric conversion layer 130 may include at least one p-type semiconductor and at least one n-type semiconductor for photoelectric conversion of the absorbed light. The p-type semiconductor and the n-type semiconductor may form a pn junction, generate excitons by receiving light from the outside, and then separate the generated excitons into holes and electrons.

The aforementioned compound may be included in the photoelectric conversion layer 130, and may be, for example, a p-type semiconductor or an n-type semiconductor. For example, the aforementioned compound may be a p-type semiconductor, and the photoelectric conversion layer 130 may further include an n-type semiconductor that forms a pn junction with the compound. For example, the LUMO energy level (based on an absolute value) of the n-type semiconductor may be about 2.1 eV to about 4.0 eV, and within the above range, about 2.2 eV to about 4.0 eV, about 2.3 eV to about 4.0 eV, or about 2.4 eV to about 3.9 eV.

For example, the n-type semiconductor may be a light absorbing material configured to absorb light of a visible light wavelength spectrum, and may include, for example, fullerene or a fullerene derivative.

For example, the n-type semiconductor may be a transparent material configured not to substantially absorb light of a visible light wavelength spectrum. The transparent material may have a wide energy bandgap so as not to substantially absorb light of a visible light wavelength spectrum, and for example, may have an energy bandgap of greater than or equal to about 2.5 eV. The energy bandgap of the transparent material may be, for example, about 2.5 eV to about 6.0 eV, within the above range.

The n-type semiconductor may be a material that may be vacuum-deposited like the aforementioned compound, for example, a sublimable material that may be vacuum-deposited by sublimation without substantial decomposition or polymerization, within a particular (or, alternatively, predetermined) temperature range. The sublimable materials may be identified by thermogravimetric analysis (TGA) and may be organic materials that lose a weight with increasing temperature and lose a weight by at least about 10% of their initial weight without substantial decomposition or polymerization. For example, the n-type semiconductor may have a sublimation temperature at which a weight loss of 10% relative to the initial weight occurs during thermogravimetric analysis at a pressure of about 10 Pa or less, within a particular (or, alternatively, predetermined) range. For example, the sublimation temperature of the n-type semiconductor may be each less than or equal to about 380° C., within the above range, less than or equal to about 370° C., less than or equal to about 360° C., less than or equal to about 350° C., less than or equal to about 340° C., less than or equal to about 330° C., less than or equal to about 320° C., less than or equal to about 310° C., less than or equal to about 300° C., less than or equal to about 290° C., less than or equal to about 280° C., less than or equal to about 270° C., less than or equal to about 250° C., about 100° C. to about 380° C., about 100° C. to about 370° C., about 100° C. to about 360° C., about 100° C. to about 350° C., about 100° C. to about 340° C., about 100° C. to about 330° C., about 100° C. to about 320° C., about 100° C. to about 310° C., about 100° C. to about 300° C., about 100° C. to about 290° C., about 100° C. to about 280° C., about 100° C. to about 270° C., about 100° C. to about 250° C., about 150° C. to about 380° C., about 150° C. to about 370° C., about 150° C. to about 360° C., about 150° C. to about 350° C., about 150° C. to about 340° C., about 150° C. to about 330° C., about 150° C. to about 320° C., about 150° C. to about 310° C., about 150° C. to about 300° C., about 150° C. to about 290° C., about 150° C. to about 280° C., about 150° C. to about 270° C., or about 150° C. to about 250° C.

The photoelectric conversion layer 130 may be an intrinsic layer (layer 1) in which a p-type semiconductor and an n-type semiconductor are blended in a bulk heterojunction form. Herein, the p-type semiconductor and the n-type semiconductor may be blended in a volume ratio (thickness ratio) of about 1:9 to about 9:1, and within the above range, about 2:8 to about 8:2, within the above range, about 3:7 to about 7:3, within the above range, about 4:6 to about 6:4, and within the above range, about 5:5.

The photoelectric conversion layer 130 may further include a p-type layer and/or an n-type layer in addition to the intrinsic layer (I layer). The p-type layer may include the aforementioned p-type semiconductor, and the n-type layer may include the aforementioned n-type semiconductor. For example, they may be included in various combinations such as p-type layer/I-layer, I-layer/n-type layer, p-type layer/I-layer/n-type layer, and the like.

The photoelectric conversion layer 130 may include a bi-layer including a p-type layer including the aforementioned p-type semiconductor and an n-type layer including the aforementioned n-type semiconductor. Herein, the thickness ratio of the p-type layer and the n-type layer may be about 1:9 to about 9:1, and within the above range, for example, about 2:8 to about 8:2, about 3:7 to about 7:3, about 4:6 to about 6:4, or about 5:5.

The photoelectric conversion layer 130 may have a thickness of about 10 nm to about 500 nm, and within the above range, about 20 nm to about 300 nm. Within the above thickness range, photoelectric conversion efficiency may be effectively improved by effectively absorbing light and effectively separating and transferring holes and electrons.

The auxiliary layers 140 and 150 may include a first auxiliary layer 140 between the first electrode 110 and the photoelectric conversion layer 130 and a second auxiliary layer 150 between the second electrode 120 and the photoelectric conversion layer 130. The first and second auxiliary layers 140 and 150 may each independently be a charge auxiliary layer for controlling the mobility of holes and/or electrons separated from the photoelectric conversion layer 130 or a light absorption auxiliary layer for improving light absorption characteristics.

The first and second auxiliary layers 140 and 150 may each independently include an organic material, an inorganic material, and/or an organic-inorganic material. The first and second auxiliary layers 140 and 150 may include at least one of a hole injecting layer (HIL), a hole transporting layer (HTL), an electron blocking layer (EBL), an electron injecting layer (EIL), an electron transporting layer (ETL), a hole blocking layer (HBL), or a light absorption auxiliary layer, but are not limited thereto.

The hole injection layer, the hole transport layer, and/or the electron blocking layer may include, for example, a phthalocyanine compound such as copper phthalocyanine; DNTPD (N,N'-diphenyl-N,N'-bis-[4-(phenyl-m-tolylamino)-phenyl]-biphenyl-4,4'-diamine), m-MTDATA (4,4',4"-[tris(3-methylphenyl)phenylamino]triphenylamine), TDATA (4,4'4"-tris(N,N-diphenylamino)triphenylamine), 2-TNATA (4,4',4"-tris{N,N-(2-naphthyl)-N-phenylamino}-triphenylamine), PEDOT/PSS (poly(3,4-ethylenedioxythiophene)/poly(4-styrenesulfonate)), PANI/DBSA (polyaniline/dodecylbenzenesulfonic acid), PANI/CSA (polyaniline/Camphor sulfonic acid), PANI/PSS (polyaniline/poly(4-styrenesulfonate)), NPB (N,N'-di(naphthalene-1-yl)-N,N'-diphenylbenzidine), polyetherketone including triphenylamine (TPAPEK), 4-isopropyl-4'-methyldiphenyliodonium[tetrakis(pentafluorophenyl)borate], HAT-CN (dipyrazino[2,3-f: 2',3'-h]quinoxaline-2,3,6,7,10,11-hexacarbonitrile), a carbazole-based derivative such as N-phenylcarbazole, polyvinylcarbazole, and the like, a fluorene-based derivative, TPD (N,N'-bis(3-methylphenyl)-N,N'-diphenyl-[1,1-biphenyl]-4,4'-diamine), a triphenylamine-based derivative such as TCTA (4,4',4"-tris(N-carbazolyl)triphenylamine), NPB (N,N'-di(naphthalene-1-yl)-N,N'-diphenyl-benzidine), TAPC (4,4'-cyclohexylidene bis[N,N-bis(4-methylphenyl)benzenamine]), HMTPD (4,4'-bis[N,N'-(3-tolyl)amino]-3,3'-dimethylbiphenyl), mCP (1,3-bis(N-carbazolyl)benzene), or any combination thereof, but are not limited thereto.

The electron injection layer, the electron transport layer, and/or the hole blocking layer may be, for example, a halogenated metal such as LiF, NaCl, CsF, RbCl, and Rbl; a lanthanide metal such as Yb; a metal such as calcium (Ca), potassium (K), aluminum (Al), or an alloy thereof; a metal oxide such as $Li_2O$ or BaO; Liq (lithium quinolate), Alq3 (tris(8-hydroxyquinolinato)aluminum), 1,3,5-tri[(3-pyridyl)-phen-3-yl]benzene, 2,4,6-tris(3'-(pyridin-3-yl)biphenyl-3-yl)-1,3,5-triazine, 2-(4-(N-phenylbenzoimidazolyl-1-ylphenyl)-9,10-dinaphthylanthracene, TPBi (1,3,5-tri(1-phenyl-1H-benzo[d]imidazol-2-yl)phenyl), BCP (2,9-dimethyl-4,7-diphenyl-1,10-phenanthroline), Bphen (4,7-diphenyl-1,10-phenanthroline), TAZ (3-(4-biphenylyl)-4-phenyl-5-tertbutylphenyl-1,2,4-triazole), NTAZ (4-(naphthalen-1-yl)-3,5-diphenyl-4H-1,2,4-triazole), tBu-PBD (2-(4-biphenylyl)-5-(4-tert-butylphenyl)-1,3,4-oxadiazole), BAlq (bis(2-methyl-8-quinolinolato-N1,O8)-(1,1'-biphenyl-4-olato)aluminum), $Bebq_2$ (berylliumbis(benzoquinolin-10-olate), ADN (9,10-di(naphthalene-2-yl) anthracene, BmPyPhB (1,3-bis[3,5-di(pyridin-3-yl)phenyl] benzene), or any combination thereof, but are not limited thereto.

Any one of the first or second auxiliary layers 140 and 150 may be omitted.

The sensor 100 may further include an anti-reflection layer (not shown) disposed under the first electrode 110 or on the second electrode 120. For example, when the first electrode 110 is a light-receiving electrode, the anti-reflection layer may be disposed under the first electrode 110. For example, when the second electrode 120 is a light-receiving electrode, the anti-reflection layer may be disposed on the second electrode 120. The anti-reflection layer may be disposed at a light incidence side and lower reflectance of light of incident light and thereby light absorbance is further improved. The anti-reflection layer may include, for example a material having a refractive index of about 1.6 to about 2.5, and may include for example at least one of metal oxide, metal sulfide, or an organic material having a refractive index within the above ranges. The anti-reflection layer may include, for example a metal oxide such as aluminum-containing oxide, molybdenum-containing oxide, tungsten-containing oxide, vanadium-containing oxide, rhenium-containing oxide, niobium-containing oxide, tantalum-containing oxide, titanium-containing oxide, nickel-containing oxide, copper-containing oxide, cobalt-containing oxide, manganese-containing oxide, chromium-containing oxide, tellurium-containing oxide, or any combination thereof; a metal sulfide such as zinc sulfide; or an organic material such as an amine derivative, but is not limited thereto.

The sensor 100 may further include a focusing lens (not shown). The focusing lens may collect the light to a single point by controlling the direction of the incident light at a light incident position. The focusing lens may have a shape of, for example, a cylinder or a hemisphere, but is not limited thereto.

In the sensor 100, when light enters from the first electrode 110 or the second electrode 120 and the photoelectric conversion layer 130 absorbs light in a particular (or, alternatively, predetermined) wavelength region, excitons may be produced thereinside. The excitons may be separated into holes and electrons in the photoelectric conversion layer 130, and the separated holes are transported to an anode that is one of the first electrode 110 or the second electrode 120 and the separated electrons are transported to the cathode that is the other of the first electrode 110 and the second electrode 120 so as to flow a current.

The sensor 100 may be included in, for example, an image sensor or a biometric sensor.

The image sensor may be for example a CMOS image sensor.

The biometric sensor may include, for example, a fingerprint sensor, an iris recognition sensor, a distance sensor, a photoplethysmography (PPG) sensor device, an electroencephalogram (EEG) sensor device, an electrocardiogram (ECG) sensor device, a blood pressure (BP) sensor device, an electromyography (EMG) sensor device, a blood glucose (BG) sensor device, an accelerometer device, a RFID antenna device, an inertial sensor device, an activity sensor device, a strain sensor device, a motion sensor device, or any combination thereof, but is not limited thereto.

For example, the aforementioned sensor 100 may be included in an image sensor, and has improved optical and electrical properties and reduces an image afterimage due to remaining charges, thereby being applied to an image sensor suitable for high-speed photographing.

Hereinafter, an image sensor according to some example embodiments is described.

Figure 2:
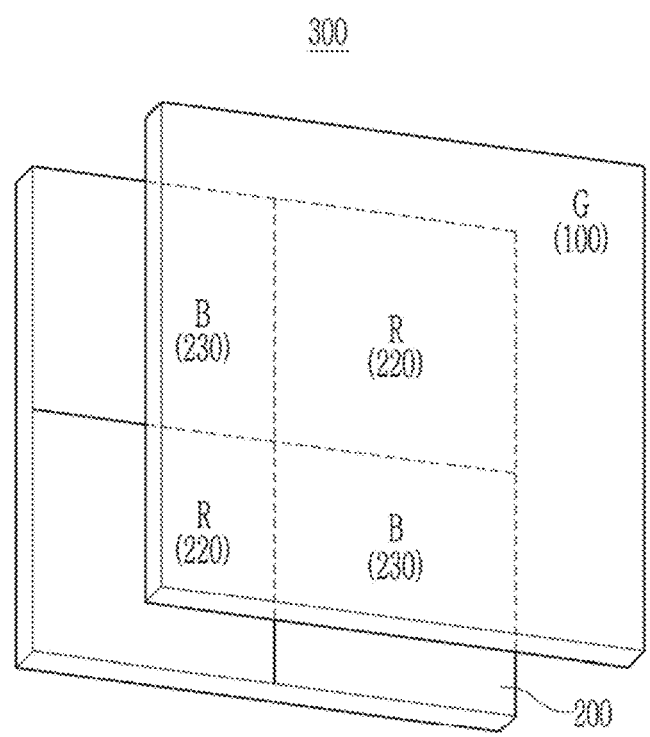
FIG. 2 is a plan view showing an example of an image sensor according to some example embodiments.
Figure 3:
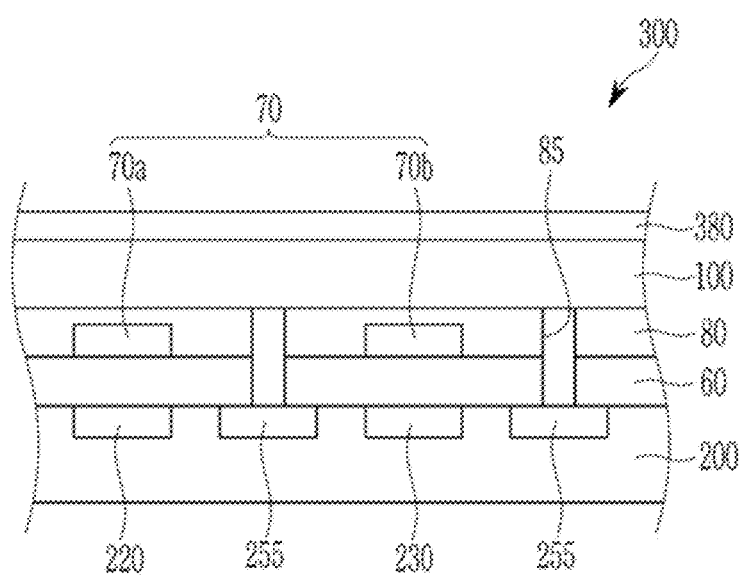
FIG. 3 is a cross-sectional view showing an example of the image sensor of FIG. 2 according to some example embodiments.

FIG. 2 is a plan view showing an example of an image sensor according to some example embodiments and FIG. 3 is a cross-sectional view showing an example of the image sensor of FIG. 2.

Referring to FIG. 2, the image sensor 300 according to some example embodiments may be a stacked sensor in which a semiconductor substrate 200 and the aforementioned sensor 100 are stacked, and the semiconductor substrate 200 includes a first photodiode 220 and a second photodiode 230 which are overlapped with the sensor 100. FIG. 2 illustrates an example of a repeating unit pixel group in the image sensor 300, and the unit pixel group is repeatedly arranged along rows and/or columns. In FIG. 2, the unit pixel group is shown as a 2×2 array in which two red pixels (R) and two blue pixels (B) are arranged on a semiconductor substrate 200, but not limited thereto.

A first photodiode 220 and a second photodiode 230 are each integrated on the semiconductor substrate 200 and thus may be configured to absorb and convert light in each different wavelength spectrum which is filtered by a color filter layer 70, which will be described later. A wavelength spectrum photoelectrically converted in the sensor 100 may be different respectively from the wavelength spectra photoelectrically converted in the first photodiode 220 and the second photodiode 230, for example, the wavelength spectrum photoelectrically converted in the first photodiode 220 and the wavelength spectrum photoelectrically converted in the second photodiode 230 may be respectively different from the wavelength spectrum photoelectrically converted in the sensor 100 and selected from light of a red wavelength spectrum, a green wavelength spectrum, and a blue wavelength spectrum. For example, the first photodiode 220 may be configured to photoelectrically convert light of the red wavelength spectrum (R), the second photodiode 230 may be configured to photoelectrically convert light of the blue wavelength spectrum (B), and the sensor 100 may be configured to photoelectrically convert light of the green wavelength spectrum (G).

Referring to FIG. 3, an image sensor 300 according to some example embodiments includes a substrate 200, a lower insulation layer 60, a color filter layer 70, an upper insulation layer 80, a sensor 100, and an encapsulation layer 380.

The substrate 200 may be a semiconductor substrate, and the first and second photodiodes 220 and 230, a transmission transistor (not shown) and the charge storage 255 are integrated therein. The first or second photodiode 220 and 230, transmission transistor and/or charge storage 255 may be integrated for each pixel. As shown in the drawing, the first photodiode 220 may be included in the red pixel R and the second photodiode 230 may be included in the blue pixel B. The charge storage 255 is electrically connected to the sensor 100.

A metal wire (not shown) and a pad (not shown) are formed under the substrate 200. In order to decrease signal delay, the metal wire and pad may be made of a metal having low resistivity, for example, aluminum (Al), copper (Cu), silver (Ag), and alloys thereof, but is not limited thereto.

The lower insulation layer 60 is formed on the substrate 200. The lower insulation layer 60 may be made of an inorganic insulating material such as a silicon oxide and/or a silicon nitride, or a low dielectric constant (low K) material such as SiC, SiCOH, SiCO, and SiOF. The lower insulation layer 60 has a trench 85 exposing the charge storage 255. The trench 85 may be filled with fillers.

The color filter layer 70 is formed on the lower insulation layer 60. The color filter layer 70 includes a red filter 70a formed in the red pixel R and a blue filter 70b formed in the blue pixel B. However, the present inventive concepts are not limited thereto, and a cyan filter, a magenta filter, and/or a yellow filter may be included instead of the red filter 70a and/or the blue filter 70b, or may be additionally included in addition to the red filter 70a and the blue filter 70b. Although an example in which the green filter is not provided is described in some example embodiments, including the example embodiments shown in FIG. 3, a green filter may be provided in some example embodiments.

The upper insulation layer 80 is formed on the color filter layer 70. The upper insulation layer 80 may remove the step difference caused by the color filter layer 70 and may be planarized. The upper insulation layer 80 and the lower insulation layer 60 have a contact (not shown) exposing the pad and a trench 85 exposing the charge storage 255.

The aforementioned sensor 100 is formed on the upper insulation layer 80. A detailed description of the sensor 100 is the same as described above. One of the first electrode 110 or the second electrode 120 of the sensor 100 may be electrically connected to the charge storage 255 and the other of the first electrode 110 and the second electrode 120 of the sensor 100 may be a light-receiving electrode. For example, the first electrode 110 of the sensor 100 may be electrically connected to the charge storage 255, and the second electrode 120 of the sensor 100 may be a light-receiving electrode.

The encapsulation layer 380 may protect the image sensor 300, and may include a thin film of one or two or more layers including an organic material, an inorganic material, an organic-inorganic material, or any combination thereof. The encapsulation layer 380 may include, for example, a glass plate, a metal thin film, an organic layer, an inorganic layer, an organic-inorganic layer, or any combination thereof. The organic layer may include, for example, an acrylic resin, a (meth)acrylic resin, polyisoprene, a vinyl resin, an epoxy resin, a urethane resin, a cellulose resin, a perylene resin, or any combination thereof, but is not limited thereto. The inorganic layer may include, for example, oxide, nitride, and/or oxynitride, for example, silicon oxide, silicon nitride, silicon oxynitride, aluminum oxide, aluminum nitride, aluminum oxynitride, zirconium oxide, zirconium nitride, zirconium oxynitride, titanium oxide, titanium nitride, titanium oxynitride, hafnium oxide, hafnium nitride, hafnium oxynitride, tantalum oxide, tantalum nitride, tantalum oxynitride, lithium fluoride, or any combination thereof, but is not limited thereto. The organic/inorganic layer may include, for example, polyorganosiloxane but is not limited thereto. The encapsulation layer 380 may have one layer or two or more layers. The encapsulation layer 380 may be omitted.

A focusing lens (not shown) may be further formed on the sensor 100 (or the encapsulation layer 380). The focusing lens may control the direction of the incident light to collect the light to a single point. The focusing lens may have a shape of, for example, a cylinder or a hemisphere, but is not limited thereto.

Figure 4:
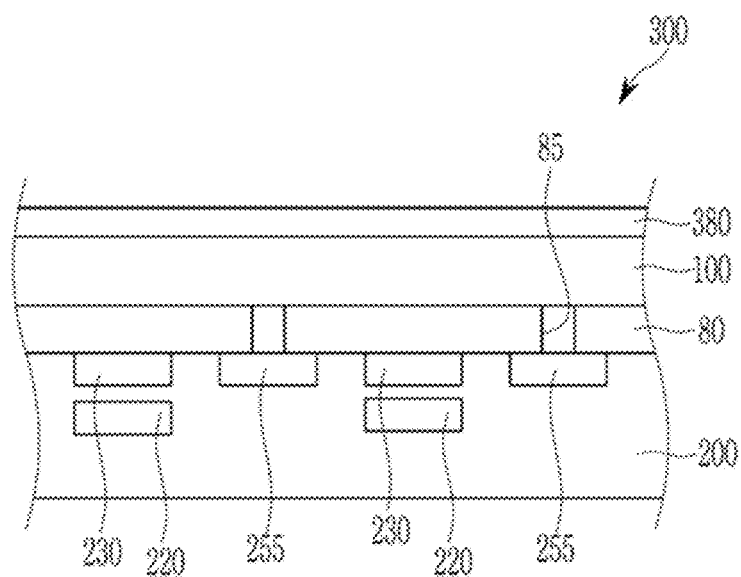
FIG. 4 is a cross-sectional view showing another example of the image sensor of FIG. 2 according to some example embodiments.

FIG. 4 is a cross-sectional view showing another example of the image sensor of FIG. 2 according to some example embodiments.

Referring to FIG. 4, the image sensor 300 according to some example embodiments includes a substrate 200 integrated with the first and second photodiodes 220 and 230, a transmission transistor (not shown), and a charge storage 255; an upper insulation layer 80; a sensor 100; and an encapsulation layer 380, like some example embodiments, including the example embodiments shown in FIG. 3.

However, in the image sensor 300 according to some example embodiments, including the example embodiments shown in FIG. 4, the first and second photodiodes 220 and 230 are stacked in a vertical direction with respect to the in-plane direction (e.g., a thickness direction of substrate 200) of the substrate 200, and the color filter layer 70 is omitted, unlike some example embodiments, including the example embodiments shown in FIG. 3. The first and second photodiodes 220 and 230 are electrically connected to a charge storage (not shown) and may be transferred by a transmission transistor. The first and second photodiodes 220 and 230 may be configured to selectively absorb light in each wavelength region according to the stacking depth.

The sensor 100 is the same as described above. One of the first electrode 110 or the second electrode 120 of the sensor 100 may be a light-receiving electrode, and the other of the first electrode 110 and the second electrode 120 of the sensor 100 may be electrically connected to the charge storage 255.

Figure 5:
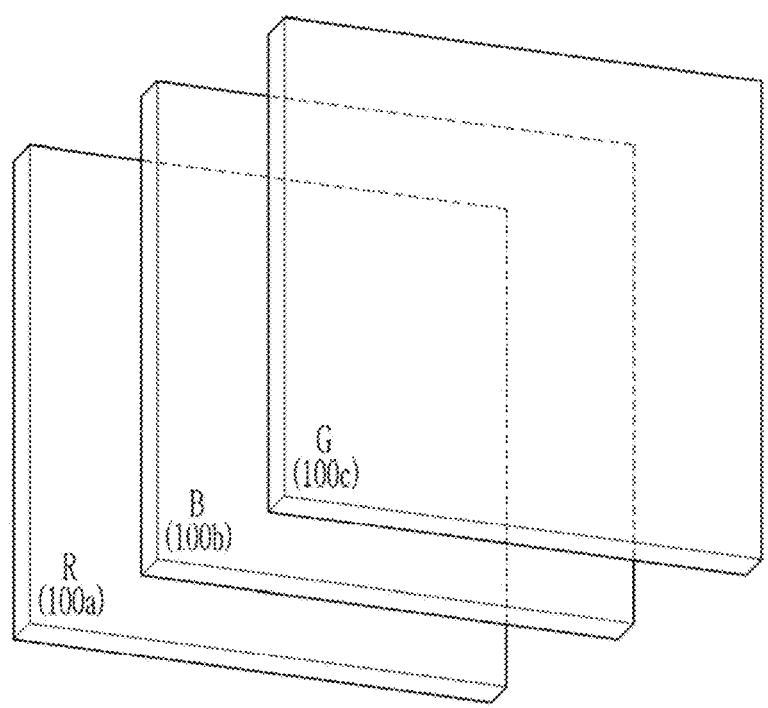
FIG. 5 is a plan view showing another example of an image sensor according to some example embodiments.
Figure 6:
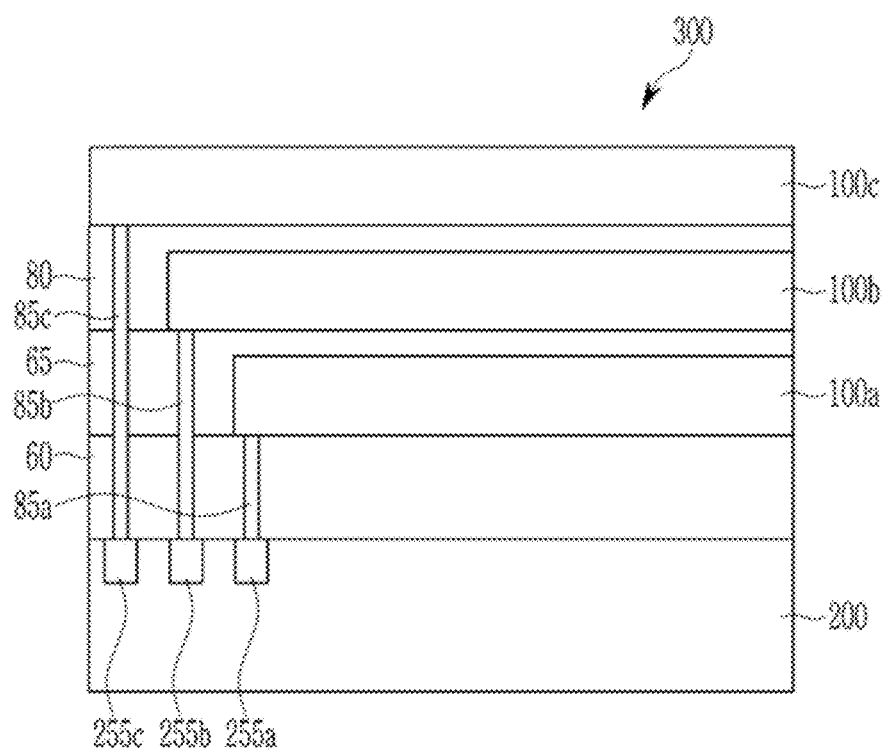
FIG. 6 is a cross-sectional view showing an example of the image sensor of FIG. 5 according to some example embodiments.

FIG. 5 is a plan view showing another example of an image sensor according to some example embodiments, and FIG. 6 is a cross-sectional view showing an example of the image sensor of FIG. 5.

The image sensor 300 according to some example embodiments, including the example embodiments shown in FIGS. 5 and 6 may have a structure in which a green sensor configured to selectively absorb light in a green wavelength region, a blue sensor configured to selectively absorb light in a blue wavelength region, and a red sensor configured to selectively absorb light in a red wavelength region are stacked.

The image sensor 300 according to some example embodiments includes a substrate 200, a lower insulation layer 60, an intermediate insulation layer 65, an upper insulation layer 80, a first sensor 100a, a second sensor 100b, and a third sensor 100c.

The substrate 200 may be a semiconductor substrate such as a silicon substrate, and a transmission transistor (not shown) and charge storages 255a, 255b, and 255c are integrated.

A metal wire (not shown) and a pad (not shown) are formed on the substrate 200, and a lower insulation layer 60 is formed on the metal wire and the pad.

The first sensor 100a, the second sensor 100b, and the third sensor 100c are sequentially formed on the lower insulation layer 60.

The first, second, and third sensors 100a, 100b, and 100c may each be the aforementioned sensor 100. One of the first electrode 110 or the second electrode 120 of the first, second, and third sensors 100a, 100b, and 100c may be a light-receiving electrode, and the other of the first electrode 110 or the second electrode 120 of the first, second, and third sensors 100a, 100b, and 100c may be connected to the charge storages 255a, 255b, and 255c.

The first sensor 100a may be configured to selectively absorb light in any one wavelength region of red, blue, and green to photoelectrically convert it. For example, the first sensor 100a may be a red sensor. The intermediate insulation layer 65 is formed on the first sensor 100a.

The second sensor 100b is formed on the intermediate insulation layer 65. The second sensor 100b may be configured to selectively absorb light of any one wavelength region among red, blue, and green to photoelectrically convert it. For example, the second sensor 100b may be a blue sensor.

The upper insulation layer 80 is formed on the second sensor 100b. The lower insulation layer 60, the intermediate insulation layer 65, and the upper insulation layer 80 have a plurality of trenches 85a, 85b, and 85c exposing charge storages 255a, 255b, and 255c.

The third sensor 100c is formed on the upper insulation layer 80. The third sensor 100c may be configured to selectively absorb light of any one wavelength region among red, blue, and green to photoelectrically convert it. For example, the third sensor 100c may be a green sensor.

A focusing lens (not shown) may be further formed on the third sensor 100c. The focusing lens may control the direction of the incident light to collect the light to a single point. The focusing lens may have a shape of, for example, a cylinder or a hemisphere, but is not limited thereto.

Although the drawing shows a structure in which the first sensor 100a, the second sensor 100b, and the third sensor 100c are sequentially stacked, the stacking order is not limited thereto and the stacking order may be variously changed.

As described above, the first sensor 100a, the second sensor 100b, and the third sensor 100c, which are configured to absorb light in different wavelength regions from each other, are stacked, thereby further reducing a size of the image sensor to provide a miniaturized image sensor.

Figure 7:
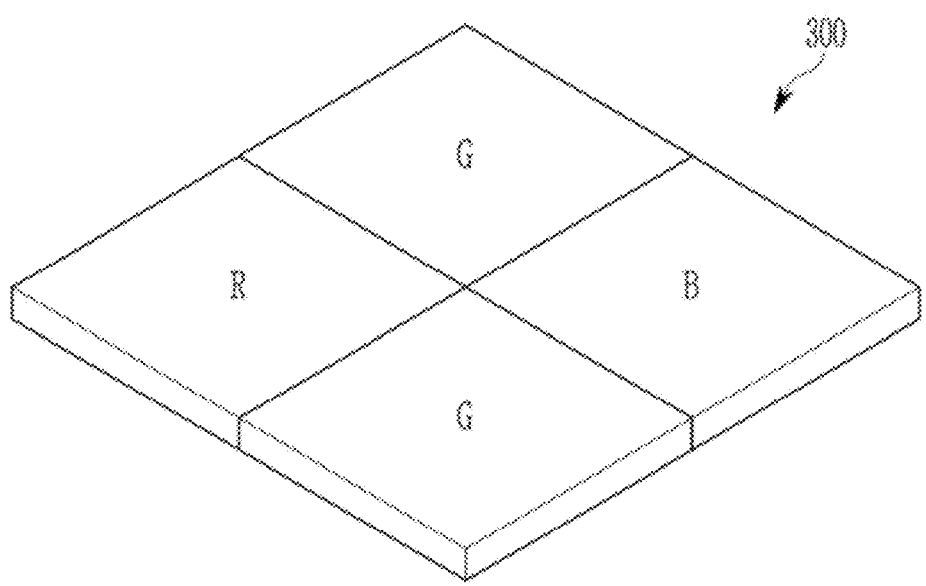
FIG. 7 is a plan view showing another example of an image sensor according to some example embodiments.
Figure 8:
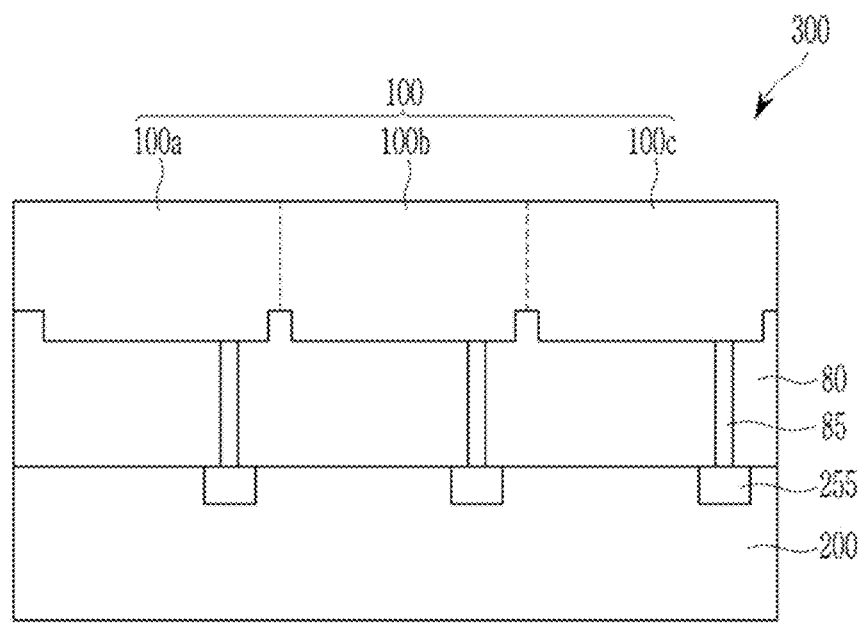
FIG. 8 is a cross-sectional view showing an example of the image sensor of FIG. 7 according to some example embodiments.

FIG. 7 is a plan view showing another example of an image sensor according to some example embodiments, and FIG. 8 is a cross-sectional view showing an example of the image sensor of FIG. 7.

Referring to FIGS. 7 and 8, the image sensor 300 includes the sensor 100 disposed on the substrate 200, and the sensor 100 includes the first, second, and third sensors 100a, 100b, and 100c. The first, second, and third sensors 100a, 100b, and 100c may be configured to convert light of different wavelength regions (e.g., blue light, green light, or red light) into electrical signals.

Referring to FIG. 8, the first, second, and third sensors 100a, 100b, and 100c are arranged in a parallel direction (e.g., in-plane direction of the substrate 200) to the surface of the substrate 200 unlike some example embodiments, including the example embodiments shown in FIGS. 5 and 6. Each first, second, and third sensor 100a, 100b, and 100c is electrically connected to the charge storage 255 integrated in the substrate 200 through the trench 85.

For example, the aforementioned sensor 100 may be included in a display panel, and may be, for example, applied to a sensor-embedded display panel in which the sensor 100 is embedded in the display panel.

Hereinafter, a sensor-embedded display panel including the aforementioned sensor is described.

The sensor-embedded display panel according to some example embodiments may be a display panel capable of performing a display function and a recognition function (e.g., biometric recognition function), and may be an in-cell type display panel in which a sensor performing a recognition function (e.g., biometric recognition function) is embedded in the display panel.

Figure 9:
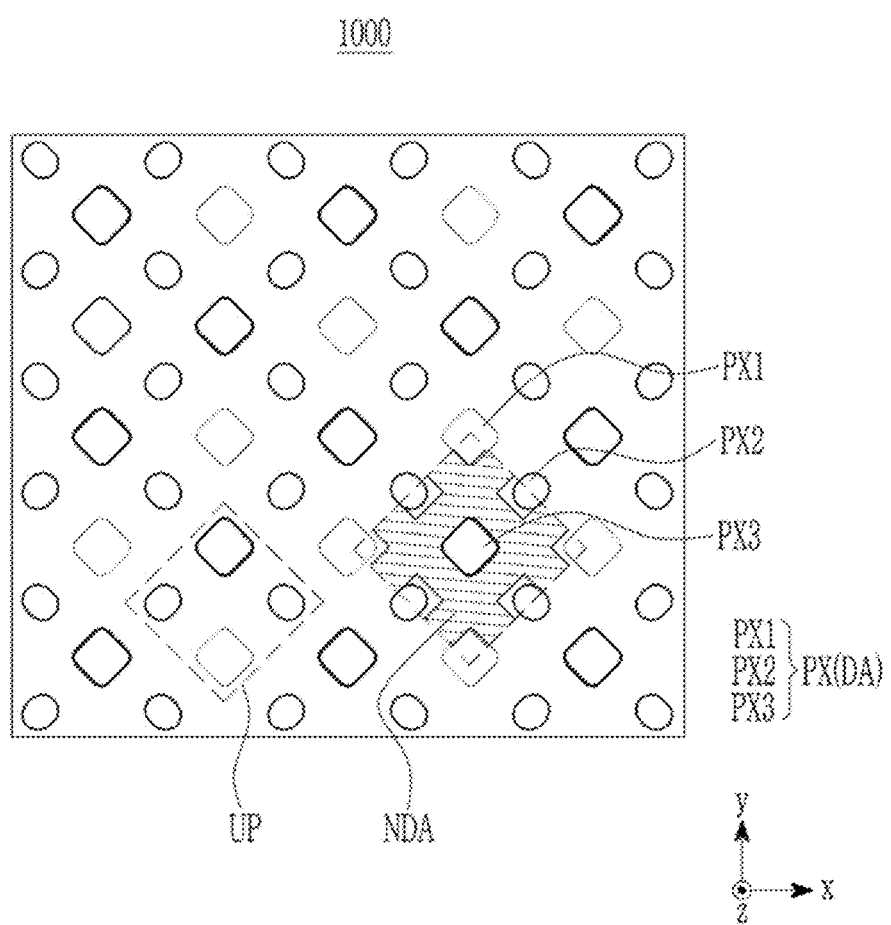
FIG. 9 is a plan view illustrating an example of a sensor-embedded display panel according to some example embodiments.
Figure 10:
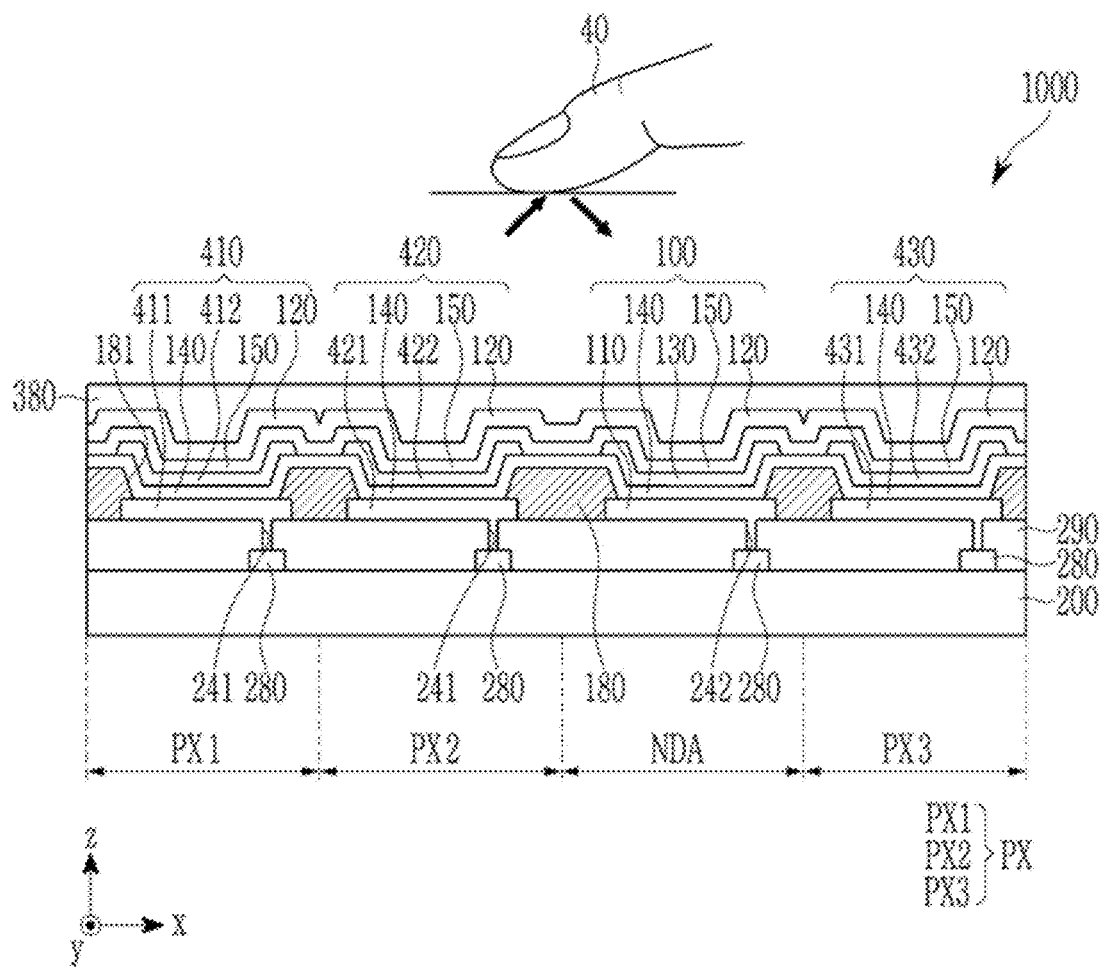
FIG. 10 is a cross-sectional view illustrating an example of a sensor-embedded display panel according to some example embodiments.

FIG. 9 is a plan view illustrating an example of a sensor-embedded display panel according to some example embodiments, and FIG. 10 is a cross-sectional view illustrating an example of a sensor-embedded display panel according to some example embodiments.

Referring to FIGS. 9 and 10, a sensor-embedded display panel 1000 according to some example embodiments includes a plurality of subpixels PXs configured to display different colors. The plurality of subpixels PXs may be configured to display at least three primary colors, for example, a first subpixel PX1, a second subpixel PX2, and a third subpixel PX3 configured to display different first color, second color, and third color selected from red, green, and blue. For example, the first color, the second color, and the third color may be red, green, and blue, respectively. The first subpixel PX1 may be a red subpixel configured to display red, the second subpixel PX2 may be a green subpixel configured to display green, and the third subpixel PX3 may be a blue subpixel configured to display blue. However, the present inventive concepts are not limited thereto, and an auxiliary subpixel (not shown) such as a white subpixel may be further included.

The plurality of subpixels PXs including the first subpixel PX1, the second subpixel PX2, and the third subpixel PX3 may constitute one unit pixel UP to be arranged repeatedly along the row and/or column. In FIG. 9, a structure including one first subpixel PX1, two second subpixels PX2, and one third subpixel PX3 in the unit pixel UP is illustrated, but the present inventive concepts are not limited thereto. At least one first subpixel PX1, at least one second subpixel PX2, and at least one third subpixel PX3 may be included in the unit pixel UP. In the drawing of FIGS. 9 and 10, as an example, an arrangement of a Pentile type is illustrated, but the present inventive concepts are not limited thereto. The subpixels PXs may be arranged variously. An area occupied by the plurality of subpixels PXs and displaying colors by the plurality of subpixels PXs may be a display area DA displaying an image.

Each of the first subpixel PX1, the second subpixel PX2, and the third subpixel PX3 may include a light emitting element. As an example, the first subpixel PX1 may include a first light emitting element 410 configured to emit light of a wavelength spectrum of a first color, the second subpixel PX2 may include a second light emitting element 420 configured to emit light of a wavelength spectrum of a second color, and the third subpixel PX3 may include a third light emitting element 430 configured to emit light of a wavelength spectrum of a third color. However, the present inventive concepts are not limited thereto, and at least one of the first subpixel PX1, the second subpixel PX2, or the third subpixel PX3 may include a light emitting element configured to emit light of a combination of a first color, a second color, and a third color, that is, light in a white wavelength spectrum, and may be configured to display a first color, a second color, or a third color through a color filter (not shown).

The sensor-embedded display panel 1000 according to some example embodiments includes the aforementioned sensor 100. The sensor 100 may be disposed in a non-display area NDA. The non-display area NDA may be an area other than the display area DA, in which the first subpixel PX1, the second subpixel PX2, the third subpixel PX3, and auxiliary subpixels are not occupied. For example, the area (e.g., in the xy plane) of the sub-pixels (PX) may collectively define the display area (DA) that is configured to display an image thereon (e.g., configured to display one or more colors). A portion of the area (e.g., in the xy plane) of the sensor embedded display panel 1000 that excludes the display area (DA) (e.g., portions of the area of the sensor embedded display panel 1000 that are between adjacent subpixels (PX) in the xy direction, xy plane, etc.) may be a non-display area (NDA) that is configured to not display an image thereon (e.g., configured to not display any color). The sensor 100 may be between at least two subpixels of the first subpixel PX1, the second subpixel PX2, or the third subpixel PX3 (e.g., between at least two subpixels of a first subpixel PX1 of a plurality of first subpixels PX1, a second subpixel PX2 of the plurality of second subpixels PX2, or a third subpixel PX3 of the plurality of third subpixels PX3, and may be in parallel with the first, second, and third light emitting elements 410, 420, and 430 in the display area DA.

The sensor 100 may be an optical type recognition sensor (e.g., a biometric sensor), and may be configured to absorb light generated by reflection of light emitted from at least one of the first, second or third light emitting elements 410, 420, or 430 in the display area DA, by a recognition target 40 such as a living body, a tool, or an object to convert it into an electrical signal. Herein, the living body may be a finger, a fingerprint, a palm, an iris, a face, and/or a wrist, but is not limited thereto. The sensor 100 may be, for example, a fingerprint sensor, an illumination sensor, an iris sensor, a distance sensor, a blood vessel distribution sensor, and/or a heart rate sensor, but is not limited thereto.

The sensor 100 may be disposed on the same plane as the first, second, and third light emitting elements 410, 420, and 430 on the substrate 200, and may be embedded in the sensor-embedded display panel 1000.

Referring to FIG. 10, the sensor-embedded display panel 1000 includes a substrate 200; a thin film transistor 280 on the substrate 200; an insulation layer 290 on the thin film transistor 280; a pixel definition layer 180 on the insulation layer 290; and first, second, or third light emitting element 410, 420, and 430 and the sensor 100 in a space partitioned by the pixel definition layer 180.

The substrate 200 may be a light-transmitting substrate, for example, a glass substrate or a polymer substrate. The polymer substrate may include, for example, polycarbonate, polymethylmethacrylate, polyethyleneterephthalate, polyethylenenaphthalate, polyimide, polyamide, polyamideimide, polyethersulfone, polyorganosiloxane, styrene-ethylene-butylene-styrene, polyurethane, polyacrylate, polyolefin, or any combination thereof, but is not limited thereto.

A plurality of thin film transistors 280 are formed on the substrate 200. One or more thin film transistor 280 may be included in each subpixel PX, and may include, for example, at least one switching thin film transistor and/or at least one driving thin film transistor. The substrate 200 on which the thin film transistor 280 is formed may be referred to as a thin film transistor substrate (TFT substrate) or a thin film transistor backplane (TFT backplane).

The insulation layer 290 may cover the substrate 200 and the thin film transistor 280 and may be formed on the whole surface of the substrate 200. The insulation layer 290 may be a planarization layer or a passivation layer, and may include an organic insulating material, an inorganic insulating material, an organic-inorganic insulating material, or any combination thereof. The insulation layer 290 may have a plurality of contact holes 241 for connecting the first, second, and third light emitting elements 410, 420, and 430 and the thin film transistor 280 and a plurality of contact holes 242 for electrically connecting the sensor 100 and the thin film transistor 280.

The pixel definition layer 180 may also be formed on the whole surface of the substrate 200 and may be between adjacent subpixels PXs to partition each subpixel PX. The pixel definition layer 180 may have a plurality of openings 181 in each subpixel PX, and in each opening 181, any one of first, second, or third light emitting elements 410, 420, or 430 or the image sensor 300 may be disposed.

The first, second, and third light emitting elements 410, 420, and 430 are formed on the substrate 200 (or thin film transistor substrate), and are repeatedly arranged along the in-plane direction (e.g., xy direction) of the substrate 200. As described above, the first, second, and third light emitting elements 410, 420, and 430 may be included in the first subpixel PX1, the second subpixel PX2, and the third subpixel PX3, respectively. The first, second, and third light emitting elements 410, 420, and 430 may be electrically connected to separate thin film transistors 280 and may be driven independently.

The first, second, and third light emitting elements 410, 420, and 430 may be configured to each independently emit light in one of a red wavelength spectrum, a green wavelength spectrum, a blue wavelength spectrum, or any combination thereof. For example, the first light emitting element 410 may be configured to emit light of a red wavelength spectrum, the second light emitting element 420 may be configured to emit light of a green wavelength spectrum, and the third light emitting element 430 may be configured to emit light of a blue wavelength spectrum. Herein, the red wavelength spectrum, the green wavelength spectrum, and the blue wavelength spectrum may have a peak emission wavelength $\lambda_{peak,L}$ in a wavelength region of greater than about 600 nm and less than about 750 nm, about 500 nm to about 600 nm, and greater than or equal to about 400 nm and less than about 500 nm, respectively.

The first, second, and third light emitting elements 410, 420, and 430 may be, for example, light emitting diodes, and for example, an organic light emitting diode including an organic material, an inorganic light emitting diode including an inorganic material, a quantum dot light emitting diode including quantum dots, or a perovskite light emitting diode including perovskite.

The sensor 100 may be formed on the substrate 200 (or thin film transistor substrate) and may be randomly or regularly arranged along the in-plane direction (e.g., xy direction) of the substrate 200. As described above, the sensor 100 may be disposed in the non-display area NDA, and may be connected to a separate thin film transistor 280 to be independently driven. The sensor 100 may be configured to absorb light of the same wavelength spectrum as the light emitted from at least one of the first, second, or third light emitting elements 410, 420, or 430 and then convert it into an electrical signal. For example, the sensor 100 may be configured to absorb light of one of a red wavelength spectrum and a green wavelength spectrum, a blue wavelength spectrum, or any combination thereof, and then convert it into an electrical signal. The sensor 100 may be, for example, a photoelectric conversion diode, for example an organic photoelectric conversion diode including an organic material.

Each of the first, second, and third light emitting elements 410, 420, and 430 and the sensor 100 may include a pixel electrode 411, 421, 431, or 110; a common electrode 120 facing the pixel electrodes 411, 421, 431, and 110 and to which a common voltage is applied, and light emitting layers 412, 422, and 432 or a photoelectric conversion layer 130, a first common auxiliary layer 140, and a second common auxiliary layer 150 between the pixel electrodes 411, 421, 431, and 110 and the common electrode 120. The pixel electrode 110 of the sensor 100 may correspond to the first electrode 110 of the aforementioned sensor 100, and the common electrode 120 of the sensor 100 may correspond to the second electrode 120 of the aforementioned sensor 100, and the first and second common auxiliary layers 140 and 150 may correspond to the first and second auxiliary layers 140 and 150 of the aforementioned sensor 100.

The first, second, and third light emitting elements 410, 420, and 430 and the sensor 100 may be arranged in parallel along the in-plane direction (e.g., xy direction) of the substrate 200, and may share the common electrode 120, the first common auxiliary layer 140, and the second common auxiliary layer 150 which are formed on the whole surface. For example, as shown in at least FIG. 10, the photoelectric conversion layer 130 of the sensor 100 and the light emitting layers 412, 422, and 432 of the first, second, and third light emitting elements 410, 420, and 430 may at least partially overlap with each other (e.g., partially or completely overlap each other) in the in-plane direction (e.g., xy direction) of the substrate 200, which may be understood to be a horizontal direction that extends in parallel to an in-plane direction of the substrate 200 as shown in FIG. 10 and/or a horizontal direction that extends in parallel to an upper surface of the substrate 200 as shown in FIG. 10, and the photoelectric conversion layer 130 and the light emitting layers 412, 422, and 432 may be at least partially positioned on the same plane (e.g., an xy plane extending in the xy directions that intersects each of the photoelectric conversion layer 130 and the light emitting layers 412, 422, and 432).

The common electrode 120 is continuously formed on the light emitting layers 412, 422, and 432 and the photoelectric conversion layer 130, and is substantially formed on the whole surface of the substrate 200. The common electrode 120 may apply a common voltage to the first, second, and third light emitting elements 410, 420, and 430 and the sensor 100.

The first common auxiliary layer 140 is between the pixel electrodes 411, 421, 431, and 110 and the light emitting layers 412, 422, 432, and the photoelectric conversion layer 130, and may be continuously formed as a single piece of material that extends on the pixel electrodes 411, 421, 431, and 110, and under the light emitting layers 412, 422, and 432 and the photoelectric conversion layer 130.

The first common auxiliary layer 140 is a charge auxiliary layer (e.g., hole auxiliary layer) that facilitates injection and/or movement of charges (e.g., holes) from the pixel electrodes 411, 421, and 431 to the light emitting layers 412, 422, and 432

For example, the HOMO energy level of the first common auxiliary layer 140 may be disposed between the HOMO energy level of the light emitting layers 412, 422, and 432 and the work function of the pixel electrodes 411, 421, 431. The work function of the pixel electrodes 411, 421, and 431, the HOMO energy level of the first common auxiliary layer 140, and the HOMO energy level of the light emitting layers 412, 422, and 432 may be sequentially deepened. On the other hand, the LUMO energy level of the first common auxiliary layer 140 may be shallower than the LUMO energy level of the photoelectric conversion layer 130 and the work function of the pixel electrode 110, respectively.

The first common auxiliary layer 140 may include an organic material, an inorganic material, an organic-inorganic material, or any combination thereof satisfying the HOMO energy level, for example a phthalocyanine compound such as copper phthalocyanine; DNTPD (N,N'-diphenyl-N,N'-bis-[4-(phenyl-m-tolyl-amino)-phenyl]-biphenyl-4,4'-diamine), m-MTDATA (4,4',4"-[tris(3-methylphenyl)phenylamino]triphenylamine), TDATA (4,4'4"-tris(N,N-diphenylamino)triphenylamine), 2-TNATA (4,4',4"-tris{N,N-(2-naphthyl)-N-phenylamino}-triphenylamine), PEDOT/PSS (poly(3,4-ethylenedioxythiophene)/poly(4-styrenesulfonate)), PANI/DBSA (polyaniline/dodecylbenzenesulfonic acid), PANI/CSA (polyaniline/Camphor sulfonic acid), PANI/PSS (polyaniline/poly(4-styrenesulfonate)), NPB (N,N'-di(naphthalene-1-yl)-N,N'-diphenylbenzidine), polyetherketone including triphenylamine (TPAPEK), 4-isopropyl-4'-methyldiphenyliodonium[tetrakis(pentafluorophenyl)borate], HAT-CN (dipyrazino[2,3-f: 2',3'-h]quinoxaline-2,3,6,7,10,11-hexacarbonitrile), a carbazole-based derivative such as N-phenylcarbazole, polyvinylcarbazole, and the like, a fluorene-based derivative, TPD (N,N'-bis(3-methylphenyl)-N,N'-diphenyl-[1,1-biphenyl]-4,4'-diamine), a triphenylamine-based derivative such as TCTA (4,4',4''-tris(N-carbazolyl)triphenylamine), NPB (N,N'-di(naphthalene-l-yl)-N,N'-diphenylbenzidine), TAPC (4,4'-cyclohexylidene bis[N,N-bis(4-methylphenyl)benzenamine]), HMTPD (4,4'-bis[N,N'-(3-tolyl)amino]-3,3'-dimethylbiphenyl), mCP (1,3-bis(N-carbazolyl)benzene), or any combination thereof, but is not limited thereto. The first common auxiliary layer 140 may be one layer or two or more layers.

The second common auxiliary layer 150 may be between the light emitting layers 412, 422, and 432 and the photoelectric conversion layer 130, and the common electrode 120. The second common auxiliary layer 150 may be continuously formed as a single piece of material that extends on the light emitting layers 412, 422, and 432, and the photoelectric conversion layer 130, and under the common electrode 120.

The second common auxiliary layer 150 is a charge auxiliary layer (e.g., an electron auxiliary layer) that facilitates injection and/or movement of charges (e.g., electrons) from the common electrode 120 to the light emitting layers 412, 422, and 432. For example, the LUMO energy level of the second common auxiliary layer 150 may be between the LUMO energy level of the light emitting layers 412, 422, and 432 and the work function of the common electrode 120. The work function of the common electrode 120, the LUMO energy level of the second common auxiliary layer 150, and the LUMO energy level of the light emitting layers 412, 422, and 432 may become shallow in sequence.

The second common auxiliary layer 150 may include an organic material, an inorganic material, an organic-inorganic material, or any combination thereof satisfying the LUMO energy level, for example a halogenated metal such as LiF, NaCl, CsF, RbCl, and Rbl; a lanthanides metal such as Yb; a metal oxide such as $Li_2O$ or BaO; Liq (lithium quinolate), Alq3 (tris(8-hydroxyquinolinato)aluminum), 1,3,5-tri[(3-pyridyl)-phen-3-yl]benzene, 2,4,6-tris (3'-(pyridin-3-yl)biphenyl-3-yl)-1,3,5-triazine, 2-(4-(N-phenylbenzoimidazolyl-1-ylphenyl)-9,10-dinaphthylanthracene, TPBi (1,3,5-tri(1-phenyl-1H-benzo[d]imidazol-2-yl)phenyl), BCP (2,9-dimethyl-4,7-diphenyl-1,10-phenanthroline), Bphen (4,7-diphenyl-1,10-phenanthroline), TAZ (3-(4-biphenylyl)-4-phenyl-5-tertbutylphenyl-1,2,4-triazole), NTAZ (4-(naphthalen-1-yl)-3,5-diphenyl-4H-1,2,4-triazole), tBu-PBD (2-(4-biphenylyl)-5-(4-tert-butylphenyl)-1,3,4-oxadiazole), BAlq (bis(2-methyl-8-quinolinolato-N1,O8)-(1,1'-biphenyl-4-olato)aluminum), $Bebq_2$ (berylliumbis(benzoquinolin-10-olate), ADN (9,10-di(naphthalene-2-yl) anthracene), BmPyPhB (1,3-bis[3,5-di(pyridin-3-yl)phenyl] benzene), or any combination thereof, but is not limited thereto. The first common auxiliary layer 140 may be one layer or two or more layers.

Each of the first, second, and third light emitting elements 410, 420, and 430 and the sensor 100 may include pixel electrodes 411, 421, 431, and 110 facing the common electrode 120. One of the pixel electrodes 411, 421, 431, and 110 or the common electrode 120 is an anode and the other is a cathode. For example, the pixel electrodes 411, 421, 431, and 110 may be an anode and the common electrode 120 may be a cathode. The pixel electrodes 411, 421, 431, and 110 are separated for each subpixel PX, and may be electrically connected to a separate thin film transistor 280 to be independently driven.

Each of the pixel electrodes 411, 421, 431, and 110 and the common electrode 120 may be a light-transmitting electrode or a reflective electrode. For example, at least one of the pixel electrodes 411, 421, 431, and 110 or the common electrode 120 may be a light-transmitting electrode.

For example, when the pixel electrodes 411, 421, 431, and 110 are light-transmitting electrodes and the common electrode 120 is a reflective electrode, the sensor-embedded display panel 1000 may be a bottom emission type display panel configured to emit light toward the substrate 200. For example, when the pixel electrodes 411, 421, 431, and 110 are reflective electrodes and the common electrode 120 is a light-transmitting electrode, the sensor-embedded display panel 1000 may be a top emission type display panel configured to emit light toward the opposite side of the substrate 200. For example, when the pixel electrodes 411, 421, 431, and 110 and the common electrode 120 are light-transmitting electrodes, respectively, the sensor-embedded display panel 1000 may be a both side emission type display panel configured to emit light toward both the substrate 200 and the opposite side of the substrate 200.

For example, the pixel electrodes 411, 421, 431, and 110 may be reflective electrodes and the common electrode 120 may be a semi-transmissive electrode. In this case, the sensor-embedded display panel 1000 may have a microcavity structure. In the microcavity structure, reflection may occur repeatedly between the reflective electrode and the semi-transmissive electrode separated by a particular (or, alternatively, predetermined) optical length (e.g., a distance between the semi-transmissive electrode and the reflective electrode) and light of a particular (or, alternatively, predetermined) wavelength spectrum may be enhanced to improve optical properties.

For example, among the light emitted from the light emitting layers 412, 422, and 432 of the first, second, and third light emitting elements 410, 420, and 430, light of a particular (or, alternatively, predetermined) wavelength spectrum may be repeatedly reflected between the semi-transmissive electrode and the reflective electrode and then may be modified. Among the modified light, light of a wavelength spectrum corresponding to a resonance wavelength of a microcavity may be enhanced to exhibit amplified light emission characteristics in a narrow wavelength region. Accordingly, the sensor-embedded display panel 1000 may express colors with high color purity.

For example, among the light incident on the sensor 100, light of a particular (or, alternatively, predetermined) wavelength spectrum may be repeatedly reflected between the semi-transmissive electrode and the reflective electrode to be modified. Among the modified light, light having a wavelength spectrum corresponding to the resonance wavelength of a microcavity may be enhanced to exhibit photoelectric conversion characteristics amplified in a narrow wavelength region. Accordingly, the sensor 100 may exhibit high photoelectric conversion characteristics in a narrow wavelength region.

Each of the first, second, and third light emitting elements 410, 420, and 430 includes light emitting layers 412, 422, and 432 between the pixel electrodes 411, 421, and 431 and the common electrode 120. Each of the light emitting layer 412 included in the first light emitting element 410, the light emitting layer 422 included in the second light emitting element 420, and the light emitting layer 432 included in the third light emitting element 430 may be configured to emit light in the same or different wavelength spectra and may be configured to emit light in, for example a red wavelength spectrum, a green wavelength spectrum, a blue wavelength spectrum, or any combination thereof.

For example, when the first light emitting element 410, the second light emitting element 420, and the third light emitting element 430 are a red light emitting elements, a green light emitting element, and a blue light emitting element, respectively, the light emitting layer 412 may be a red light emitting layer configured to emit light in a red wavelength spectrum, the light emitting layer 422 included in the second light emitting element 420 may be a green light emitting layer configured to emit light in a green wavelength spectrum, and the light emitting layer 432 included in the third light emitting element 430 may be a blue light emitting layer configured to emit light in a blue wavelength spectrum. Herein, the red wavelength spectrum, the green wavelength spectrum, and the blue wavelength spectrum may have a peak emission wavelength in a wavelength region of greater than about 600 nm and less than about 750 nm, about 500 nm to about 600 nm, and greater than or equal to about 400 nm and less than about 500 nm, respectively.

For example, when at least one of the first light emitting element 410, the second light emitting element 420, or the third light emitting element 430 is a white light emitting element, the light emitting layer of the white light emitting element may be configured to emit light of a full visible light wavelength spectrum, for example, light in a wavelength spectrum of greater than or equal to about 380 nm and less than about 750 nm, about 400 nm to about 700 nm, or about 420 nm to about 700 nm.

The light emitting layers 412, 422, and 432 may include an organic light emitting material, a quantum dot, a perovskite, or any combination thereof as a light emitting material. For example, the light emitting layers 412, 422, and 432 may include an organic light emitting material, and may include at least one host material, or a fluorescent or phosphorescent dopant.

The organic light emitting material may be, for example, perylene; rubrene; 4-(dicyanomethylene)-2-methyl-6-[p-(di-methylamino)styryl]-4H-pyran; coumarin or a derivative thereof; carbazole or a derivative thereof; TPBi (2,2',2"-(1,3,5-benzinetriyl)-tris(1-phenyl-1-H-benzimidazole); TBADN (2-t-butyl-9,10-di(naphth-2-yl)anthracene); AND (9,10-di(naphthalene-2-yl)anthracene); CBP (4,4'-bis(N-car-bazolyl)-1,1'-biphenyl); TCTA (4,4',4"-tris(carbazol-9-yl)-triphenylamine); TPBi (1,3,5-tris(N-phenylbenzimidazole-2-yl)benzene); TBADN (3-tert-butyl-9,10-di(naphth-2-yl) anthracene); DSA (distyrylarylene); CDBP (4,4"-dimethyl-biphenyl); MADN (2-Methyl-9,10-bis(naphthalen-2-yl) anthracene); TCP (1,3,5-tris(carbazol-9-yl)benzene); Alq3 (tris(8-hydroxyquinolino)lithium); an organometallic compound including Pt, Os, Ti, Zr, Hf, Eu, Tb, Tm, Rh, Ru, Re, Be, Mg, Al, Ca, Mn, Co, Cu, Zn, Ga, Ge, Pd, Ag and/or Au, a derivative thereof, or any combination thereof, but is not limited thereto.

The sublimation temperature of the known material that may be included in the light emitting layers 412, 422, and 432 may be less than or equal to about 380° C., and within the above range, less than or equal to about 370° C., less than or equal to about 360° C., less than or equal to about 350° C., less than or equal to about 340° C., less than or equal to about 330° C., less than or equal to about 320° C., less than or equal to about 310° C., less than or equal to about 300° C., less than or equal to about 290° C., less than or equal to about 280° C., less than or equal to about 270° C., less than or equal to about 250° C., about 100° C. to about 380° C., about 100° C. to about 370° C., about 100° C. to about 360° C., about 100° C. to about 350° C., about 100° C. to about 340° C., about 100° C. to about 330° C., about 100° C. to about 320° C., about 100° C. to about 310° C., about 100° C. to about 300° C., about 100° C. to about 290° C., about 100° C. to about 280° C., about 100° C. to about 270° C., about 100° C. to about 250° C., about 150° C. to about 380° C., about 150° C. to about 370° C., about 150° C. to about 360° C., about 150° C. to about 350° C., about 150° C. to about 340° C., about 150° C. to about 330° C., about 150° C. to about 320° C., about 150° C. to about 310° C., about 150° C. to about 300° C., about 150° C. to about 290° C., about 150° C. to about 280° C., about 150° C. to about 270° C., or about 150° C. to about 250° C.

The quantum dot may include, for example, a Group II-VI semiconductor compound, a Group III-V semiconductor compound, a Group IV-VI semiconductor compound, a Group IV semiconductor compound, a Group I-III-VI semiconductor compound, a Group I-II-IV-VI semiconductor compound, a Group II-III-V semiconductor compound, or any combination thereof. The Group II-IV semiconductor compound may be, for example, selected from a binary element semiconductor compound selected from CdSe, CdTe, ZnS, ZnSe, ZnTe, ZnO, HgS, HgSe, HgTe, MgSe, MgS, or a mixture thereof, a ternary element semiconductor compound selected from CdSeS, CdSeTe, CdSTe, ZnSeS, ZnSeTe, ZnSTe, HgSeS, HgSeTe, HgSTe, CdZnS, CdZnSe, CdZnTe, CdHgS, CdHgSe, CdHgTe, HgZnS, HgZnSe, HgZnTe, MgZnSe, MgZnS, or a mixture thereof; and a quaternary element semiconductor compound selected from HgZnTeS, CdZnSeS, CdZnSeTe, CdZnSTe, CdHgSeS, CdHgSeTe, CdHgSTe, HgZnSeS, HgZnSeTe, HgZnSTe, or a mixture thereof, but is not limited thereto. The Group III-V semiconductor compound may be, for example, selected from a binary element semiconductor compound selected from GaN, GaP, GaAs, GaSb, AlN, AlP, AlAs, AlSb, InN, InP, InAs, InSb, or a mixture thereof; a ternary element semiconductor compound selected from GaNP, GaNAs, GaNSb, GaPAs, GaPSb, AlNP, AlNAs, AlNSb, AlPAs, AlPSb, InNP, InNAs, InNSb, InPAs, InPSb, or a mixture thereof; and a quaternary element semiconductor compound selected from GaAlNP, GaAlNAs, GaAlNSb, GaAlPAs, GaAlPSb, GaInNP, GaInNAs, GaInNSb, GaInPAs, GaInPSb, InAlNP, InAlNAs, InAlNSb, InAlPAs, InAlPSb, or a mixture thereof, but is not limited thereto. The Group IV-VI semiconductor compound may be, for example, selected from a binary element semiconductor compound selected from SnS, SnSe, SnTe, PbS, PbSe, PbTe, or a mixture thereof; a ternary element semiconductor compound selected from SnSeS, SnSeTe, SnSTe, PbSeS, PbSeTe, PbSTe, SnPbS, SnPbSe, SnPbTe, or a mixture thereof; and a quaternary element semiconductor compound selected from SnPbSSe, SnPbSeTe, SnPbSTe, or a mixture thereof, but is not limited thereto. The Group IV semiconductor compound may be, for example, selected from a single-element semiconductor compound such as Si, Ge, or a mixture thereof; and a binary element compound selected from SiC, SiGe, or a mixture thereof, but is not limited thereto. The Group 1-III-VI semiconductor compound may be, for example, $CuInSe_2$, $CuInS_2$, CuInGaSe, CuInGaS, or a mixture thereof, but is not limited thereto. The Group I-II-IV-VI semiconductor compound may be, for example, CuZnSnSe, CuZnSnS, or a mixture thereof, but is not limited thereto. The Group II-III-V semiconductor compound may be, for example, InZnP, but is not limited thereto.

The perovskite may be $CH_3NH_3PbBr_3$, $CH_3NH_3PbI_3$, $CH_3NH_3SnBr_3$, $CH_3NH_3SnI_3$, $CH_3NH_3Sn_{1-x}Pb_xBr_3$, $CH_3NH_3Sn_{1-x}Pb_xI_3$, $HC(NH_2)_2PbI_3$, $HC(NH_2)_2SnI_3$, $(C_4H_9NH_3)_2PbBr_4$, $(C_6H_5CH_2NH_3)_2PbBr_4$, $(C_6H_5CH_2NH_3)_2PbI_4$, $(C_6H_5C_2H_4NH_3)_2PbBr_4$, $(C_6H_{13}NH_3)_2(CH_3NH_3)_{n1}Pb_nI_{3n+1}$, any combination thereof, but is not limited thereto.

The sensor 100 includes a photoelectric conversion layer 130 between the pixel electrode 110 and the common electrode 120. The photoelectric conversion layer 130 may be in parallel with the light emitting layers 412, 422, and 432 of the first, second, and third light emitting elements 410, 420, and 430 along the in-plane direction (e.g., xy direction) of the substrate 200. The photoelectric conversion layer 130 and the light emitting layers 412, 422, and 432 may be disposed on the same plane.

The photoelectric conversion layer 130 may be configured to absorb light of a particular (or, alternatively, predetermined) wavelength spectrum and convert the absorbed light into an electrical signal, and may be configured to absorb light emitted from at least one of the first, second, or third light emitting elements 410, 420, or 430 and then reflected by the recognition target 40 and convert it into an electrical signal. The photoelectric conversion layer 130 may be configured to absorb light of a red wavelength spectrum, a green wavelength spectrum, a blue wavelength spectrum, an infrared wavelength spectrum, or any combination thereof.

For example, the photoelectric conversion layer 130 may be configured to selectively absorb light in a green wavelength spectrum having a peak absorption wavelength in a wavelength region of about 500 nm to about 600 nm, and may be configured to absorb light emitted from the green light emitting element among the first, second and third light emitting elements 410, 420, and 430 and then reflected by the recognition target 40. Within the range, the peak absorption wavelength of photoelectric conversion layer 130 may belong to about 510 nm to about 580 nm, about 520 nm to about 570 nm, about 520 nm to about 560 nm, or about 520 nm to about 550 nm.

The photoelectric conversion layer 130 may include a p-type semiconductor and an n-type semiconductor that form a pn junction. The aforementioned compound may be included in the photoelectric conversion layer 130, and for example, it may be a p-type semiconductor. The photoelectric conversion layer 130 may further include an n-type semiconductor capable of forming a pn junction with the aforementioned compound. For example, the LUMO energy level (based on an absolute value) of the n-type semiconductor may be about 2.5 eV to about 4.0 eV, and within the above range, about 2.6 eV to about 4.0 eV, about 2.7 eV to about 4.0 eV, or about 2.8 eV to about 3.9 eV.

For example, the n-type semiconductor may be a transparent material that does not substantially absorb light of a visible light wavelength spectrum. The transparent material may have a wide energy bandgap so as not to substantially absorb light of a visible light wavelength spectrum, and for example, may have an energy bandgap of greater than or equal to about 2.5 eV. The energy bandgap of the transparent material may be, for example, about 2.5 eV to about 6.0 eV, within the above range.

The p-type semiconductor and the n-type semiconductor may have a difference in sublimation temperature within a particular (or, alternatively, predetermined) range so that they may be deposited in the same chamber, wherein each sublimation temperature of a given semiconductor of the p-type semiconductor or the n-type semiconductor is a temperature at which a weight loss of the given semiconductor of 10% compared to an initial weight of the given semiconductor occurs during thermogravimetric analysis of the given semiconductor at an ambient pressure of 10 Pa or less. For example, the difference between the sublimation temperature of the p-type semiconductor and the n-type semiconductor may be less than or equal to about 150° C., within the above range, for example less than or equal to about 130° C., less than or equal to about 120° C., less than or equal to about 110° C., less than or equal to about 100° C., less than or equal to about 90° C., less than or equal to about 80° C., less than or equal to about 70° C., less than or equal to about 60° C., less than or equal to about 50° C., less than or equal to about 40° C., less than or equal to about 30° C., less than or equal to about 20° C., less than or equal to about 15° C., or less than or equal to about 10° C., within the above range, about 0° C. to about 150° C., about 0° C. to about 130° C., about 0° C. to about 120° C., about 0° C. to about 110° C., about 0° C. to about 100° C., about 0° C. to about 90° C., about 0° C. to about 80° C., about 0° C. to about 70° C., about 0° C. to about 60° C., about 0° C. to about 50° C., about 0° C. to about 40° C., about 0° C. to about 30° C., about 0° C. to about 20° C., about 0° C. to about 10° C., about 2° C. to about 150° C., about 2° C. to about 130° C., about 2° C. to about 120° C., about 2° C. to about 110° C., about 2° C. to about 100° C., about 2° C. to about 90° C., about 2° C. to about 80° C., about 2° C. to about 70° C., about 2° C. to about 60° C., about 2° C. to about 50° C., about 2° C. to about 40° C., about 2° C. to about 30° C., about 2° C. to about 20° C., about 2° C. to about 15° C., or about 2° C. to about 10° C.

For example, the sublimation temperatures of the p-type semiconductor and the n-type semiconductor may be each less than or equal to about 380° C., within the above range, less than or equal to about 370° C., less than or equal to about 350° C., less than or equal to about 340° C., less than or equal to about 330° C., less than or equal to about 320° C., less than or equal to about 310° C., less than or equal to about 300° C., less than or equal to about 290° C., less than or equal to about 280° C., less than or equal to about 270° C., or less than or equal to about 250° C., about 100° C. to about 380° C., about 100° C. to about 370° C., about 100° C. to about 350° C., about 100° C. to about 340° C., about 100° C. to about 330° C., about 100° C. to about 320° C., about 100° C. to about 310° C., about 100° C. to about 300° C., about 100° C. to about 290° C., about 100° C. to about 280° C., about 100° C. to about 270° C., about 100° C. to about 250° C., about 150° C. to about 380° C., about 150° C. to about 370° C., about 150° C. to about 350° C., about 150° C. to about 340° C., about 150° C. to about 330° C., about 150° C. to about 320° C., about 150° C. to about 310° C., about 150° C. to about 300° C., about 150° C. to about 290° C., about 150° C. to about 280° C., about 150° C. to about 270° C., or about 150° C. to about 250° C.

As described above, the photoelectric conversion layer 130 may include an intrinsic layer (I-layer) in which a p-type semiconductor and an n-type semiconductor are blended in a bulk heterojunction form, and in various combinations such as an I-layer, a p-type layer/I-layer, an I-layer/n-type layer, p-type layer/I-layer/n-type layer, or may include a bi-layer including a p-type layer including a p-type semiconductor and an n-type layer including the aforementioned n-type semiconductor. When the photoelectric conversion layer 130 is a bi-layer, the p-type layer may be disposed close to the pixel electrode 110 and the n-type layer may be disposed close to the common electrode 120.

The p-type semiconductor of the photoelectric conversion layer 130 may have an energy level capable of forming effective electrical matching with the first common auxiliary layer 140, and for example, a difference between a HOMO energy level of the first common auxiliary layer 140 and a HOMO energy level of the p-type semiconductor (the aforementioned compound) may be less than or equal to about 1.2 eV, within the above range, less than or equal to about 1.1 eV, less than or equal to about 1.0 eV, less than or equal to about 0.8 eV, less than or equal to about 0.7 eV, less than or equal to about 0.5 eV, about 0 eV to about 1.2 eV, about 0 eV to about 1.1 eV, about 0 eV to about 1.0 eV, about 0 eV to about 0.8 eV, about 0 eV to about 0.7 eV, about 0 eV to about 0.5 eV, about 0.01 eV to about 1.2 eV, about 0.01 eV to about 1.1 eV, about 0.01 eV to about 1.0 eV, about 0.01 eV to about 0.8 eV, about 0.01 eV to about 0.7 eV, or about 0.01 eV to about 0.5 eV. Accordingly, charges (e.g., holes) generated in the photoelectric conversion layer 130 may pass through the first common auxiliary layer 140 and may be effectively moved and/or extracted to the pixel electrode 110.

The n-type semiconductor of the photoelectric conversion layer 130 may have an energy level capable of forming effective electrical matching with the second common auxiliary layer 150. For example, the difference between the LUMO energy level of the second common auxiliary layer 150 and the LUMO energy level of the n-type semiconductor may be less than or equal to about 1.2 eV, and within the above range, less than or equal to about 1.1 eV, less than or equal to about 1.0 eV, less than or equal to about 0.8 eV, less than or equal to about 0.7 eV, less than or equal to about 0.5 eV, about 0 eV to about 1.2 eV, about 0 eV to about 1.1 eV, about 0 eV to about 1.0 eV, about 0 eV to about 0.8 eV, about 0 eV to about 0.7 eV, about 0 eV to about 0.5 eV, about 0.01 eV to about 1.2 eV, about 0.01 eV to about 1.1 eV, about 0.01 eV to about 1.0 eV, about 0.01 eV to about 0.8 eV, about 0.01 eV to about 0.7 eV, or about 0.01 eV to about 0.5 eV. Accordingly, charges (e.g., electrons) generated in the photoelectric conversion layer 130 may pass through the second common auxiliary layer 150 and may be effectively moved and/or extracted to the common electrode 120.

For example, the light emitting layers 412, 422, and 432 may include an organic light emitting material, and the organic light emitting material of the light emitting layers 412, 422, and 432 and the p-type semiconductor and the n-type semiconductor of the photoelectric conversion layer 130 may be vacuum-deposited in the same chamber. Accordingly, a difference between the sublimation temperatures of the organic light emitting material of the light emitting layers 412, 422, and 432 and the p-type semiconductor and the n-type semiconductor of the photoelectric conversion layer 130 may be less than or equal to about 150° C., within the above range, for example less than or equal to about 130° C., less than or equal to about 120° C., less than or equal to about 110° C., less than or equal to about 100° C., less than or equal to about 90° C., less than or equal to about 80° C., less than or equal to about 70° C., less than or equal to about 60° C., less than or equal to about 50° C., less than or equal to about 40° C., less than or equal to about 30° C., less than or equal to about 20° C., less than or equal to about 15° C., or less than or equal to about 10° C., and within the above range, about 0° C. to about 150° C., about 0° C. to about 130° C., about 0° C. to about 120° C., about 0° C. to about 110° C., about 0° C. to about 100° C., about 0° C. to about 90° C., about 0° C. to about 80° C., about 0° C. to about 70° C., about 0° C. to about 60° C., about 0° C. to about 50° C., about 0° C. to about 40° C., about 0° C. to about 30° C., about 0° C. to about 20° C., about 0° C. to about 10° C., about 2° C. to about 150° C., about 2° C. to about 130° C., about 2° C. to about 120° C., about 2° C. to about 110° C., about 2° C. to about 100° C., about 2° C. to about 90° C., about 2° C. to about 80° C., about 2° C. to about 70° C., about 2° C. to about 60° C., about 2° C. to about 50° C., about 2° C. to about 40° C., about 2° C. to about 30° C., about 2° C. to about 20° C., about 2° C. to about 15° C., or about 2° C. to about 10° C.

For example, the sublimation temperatures of the organic light emitting material of the light emitting layers 412, 422, and 432 and the p-type semiconductor and the n-type semiconductor of the photoelectric conversion layer 130 may be each less than or equal to about 380° C., within the above range, less than or equal to about 370° C., less than or equal to about 360° C., less than or equal to about 350° C., less than or equal to about 340° C., less than or equal to about 330° C., less than or equal to about 320° C., less than or equal to about 310° C., less than or equal to about 300° C., less than or equal to about 290° C., less than or equal to about 280° C., less than or equal to about 270° C., or less than or equal to about 250° C., about 100° C. to about 380° C., about 100° C. to about 370° C., about 100° C. to about 360° C., about 100° C. to about 350° C., about 100° C. to about 340° C., about 100° C. to about 330° C., about 100° C. to about 320° C., about 100° C. to about 310° C., about 100° C. to about 300° C., about 100° C. to about 290° C., about 100° C. to about 280° C., about 100° C. to about 270° C., about 100° C. to about 250° C., about 150° C. to about 380° C., about 150° C. to about 370° C., about 150° C. to about 360° C., about 150° C. to about 350° C., about 150° C. to about 340° C., about 150° C. to about 330° C., about 150° C. to about 320° C., about 150° C. to about 310° C., about 150° C. to about 300° C., about 150° C. to about 290° C., about 150° C. to about 280° C., about 150° C. to about 270° C., or about 150° C. to about 250° C.

In this way, since the p-type semiconductor and the n-type semiconductor of the photoelectric conversion layer 130 may form the aforementioned electrical matching with the first and second common auxiliary layers 140 and 150, and the light emitting material of the light emitting layers 412, 422, and 432 and the p-type semiconductor and the n-type semiconductor of the photoelectric conversion layer 130 have similar thermal properties, the sensor may be effectively formed in the display panel without deterioration of electrical properties and complexity of the process.

The thickness of the light emitting layers 412, 422, and 432 and the thickness of the photoelectric conversion layer 130 may each independently be about 5 nm to about 300 nm, and within the above range, about 10 nm to about 250 nm, about 20 nm to about 200 nm, or about 30 nm to about 180 nm. A difference in thickness between the light emitting layers 412, 422, and 432 and the photoelectric conversion layer 130 may be less than or equal to about 20 nm, and within the above range, less than or equal to about 15 nm, less than or equal to about 10 nm, or less than or equal to about 5 nm, and the light emitting layers 412, 422, and 432 and the photoelectric conversion layer 130 may have substantially the same thickness.

An encapsulation layer 380 is formed on the first, second, and third light emitting elements 410, 420, 430, and the sensor 100. The encapsulation layer 380 may include, for example, a glass plate, a metal thin film, an organic layer, an inorganic layer, an organic-inorganic layer, or any combination thereof. The organic film may include, for example, an acrylic resin, a (meth)acrylic resin, polyisoprene, a vinyl resin, an epoxy resin, a urethane resin, a cellulose resin, a perylene resin, or any combination thereof, but is not limited thereto. The inorganic film may include, for example, an oxides, a nitride, and/or an oxynitride, for example silicon oxide, silicon nitride, silicon oxynitride, aluminum oxide, aluminum nitride, aluminum oxynitride, zirconium oxide, zirconium nitride, zirconium oxynitride, titanium oxide, titanium nitride, titanium oxynitride, hafnium oxide, hafnium nitride, hafnium oxynitride, tantalum oxide, tantalum nitride, tantalum oxynitride, lithium fluoride, or any combination thereof, but is not limited thereto. The organic-inorganic film may include, for example, polyorganosiloxane, but is not limited thereto. The encapsulation layer 380 may be one layer or two or more layers.

As described above, the sensor-embedded display panel 1000 according to some example embodiments includes the first, second, and third light emitting elements 410, 420, and 430 configured to emit light in a particular (or, alternatively, predetermined) wavelength spectrum to display colors, and the sensor 100 configured to absorb light reflected by the recognition target 40 and convert it into an electrical signal, in the same plane on the substrate 200, thereby performing a display function and a recognition function (e.g., biometric recognition function). Accordingly, unlike conventional display panels formed outside the display panel or formed under the display panel by manufacturing the sensor as a separate module, it may improve performance without increasing the thickness, implementing a slim-type high performance sensor-embedded display panel 1000.

In addition, since the sensor 100 uses light emitted from the first, second, and third light emitting elements 410, 420, and 430, a recognition function (e.g., biometric recognition function) may be performed without a separate light source. Therefore, it is not necessary to provide a separate light source outside the display panel, thereby reducing or preventing a decrease in the aperture ratio of the display panel due to the area occupied by the light source, and at the same time saving power consumed by the separate light source to improve power consumption.

In addition, as described above, the first, second, and third light emitting elements 410, 420, and 430 and the sensor 100 share a common electrode 120, a first common auxiliary layer 140, and a second common auxiliary layer 150, and thus the structure and process may be simplified compared with the case where the first, second, and third light emitting elements 410, 420, and 430 and the sensor 100 are formed in separate processes.

In addition, as described above, the sensor 100 may be an organic sensor including an organic photoelectric conversion layer. Accordingly, since the sensor 100 has a light absorbance that is twice or more higher than that of an inorganic diode such as a silicon photodiode, it may have a high sensitivity sensing function with a thinner thickness.

In addition, since the sensor 100 may be disposed anywhere in the non-display area NDA, they may be disposed at a desired location of the sensor-embedded display panel 1000 as many as desired. Therefore, for example, by randomly or regularly arranging the sensor 100 over the entire sensor-embedded display panel 1000, the biometric recognition function may be performed on any portion of the screen of an electronic device such as a mobile device and the biometric recognition function may be selectively performed only in a specific location where the biometric recognition function is required.

Hereinafter, another example of the sensor-embedded display panel 1000 according to some example embodiments will be described.

Figure 11:
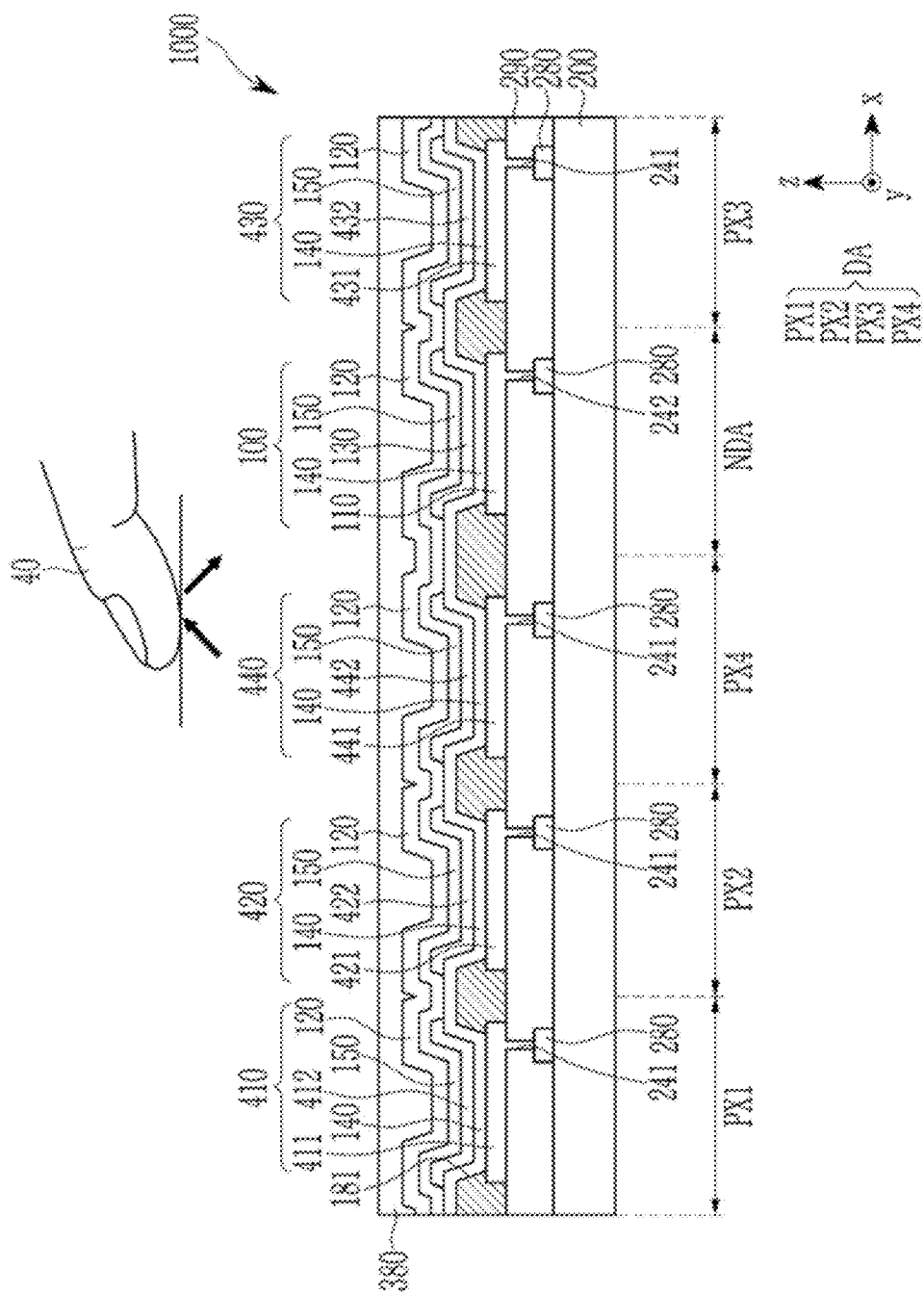
FIG. 11 is a cross-sectional view illustrating another example of a sensor-embedded display panel according to some example embodiments.

FIG. 11 is a cross-sectional view illustrating another example of a sensor-embedded display panel according to some example embodiments.

Referring to FIG. 11, a sensor-embedded display panel 1000 according to some example embodiments includes a plurality of subpixels PXs configured to display different colors, that is, a first subpixel PX1, a second subpixel PX2, and a third subpixel PX3 configured to display a first color, a second color, and a third color selected from red, green, and blue, and the first subpixel PX1, the second subpixel PX2, and the third subpixel PX3 include a first light emitting element 410, a second light emitting element 420, and a third light emitting element 430, respectively, like some example embodiments, including the example embodiments shown in FIGS. 9 and 10.

However, unlike some example embodiments, including the example embodiments shown in FIGS. 9 and 10, the sensor-embedded display panel 1000 according to some example embodiments may include the fourth light emitting element 440 configured to emit light in an infrared wavelength spectrum. For example, the fourth light emitting element 440 may be included in a fourth subpixel PX4 adjacent to the first subpixel PX1, the second subpixel PX2, and/or the third subpixel PX3, or may be included in a non-display area NDA. The fourth subpixel PX4 may form one unit pixel UP together with the first subpixel PX1, the second subpixel PX2, and the third subpixel PX3, and the unit pixel UP may be arranged repeatedly along rows and/or columns.

Descriptions of the first subpixel PX1, the second subpixel PX2, the third subpixel PX3, the first light emitting element 410, the second light emitting element 420, the third light emitting element 430, and the sensor 100 are the same as described above.

The fourth light emitting element 440 is disposed on the substrate 200 and may be disposed on the same plane as the first, second, and third light emitting elements 410, 420, and 430 and the sensor 100. The fourth light emitting element 440 may be electrically connected to a separate thin film transistor 280 and driven independently. The fourth light emitting element 440 may have a structure in which the pixel electrode 441, the first common auxiliary layer 140, the light emitting layer 442, the second common auxiliary layer 150, and the common electrode 120 are sequentially stacked. Among them, the common electrode 120, the first common auxiliary layer 140, and the second common auxiliary layer 150 may be shared with the first, second, third light emitting elements 410, 420, and 430 and the sensor 100. The light emitting layer 442 may be configured to emit light in an infrared wavelength spectrum, and may have, for example, a peak emission wavelength in greater than or equal to about 750 nm, about 750 nm to about 20 μm, about 780 nm to about 20 μm, about 800 nm to about 20 μm, about 750 nm to about 15 μm, about 780 nm to about 15 μm, about 800 nm to about 15 μm, about 750 nm to about 10 μm, about 780 nm to about 10 μm, about 800 nm to about 10 μm, about 750 nm to about 5 μm, about 780 nm to about 5 μm, about 800 nm to about 5 μm, about 750 nm to about 3 μm, about 780 nm to about 3 μm, about 800 nm to about 3 μm, about 750 nm to about 2 μm, about 780 nm to about 2 μm, about 800 nm to about 2 μm, about 750 nm to about 1.5 μm, about 780 nm to about 1.5 μm, or about 800 nm to about 1.5 μm.

The sensor 100 may be configured to absorb light emitted from at least one of the first, second, third, or fourth light emitting elements 410, 420, 430, or 440 and then reflected by a recognition target 40 such as a living body or a tool, and then convert it into an electrical signal. For example, the sensor 100 may be configured to absorb light emitted from at least one of the first, second, third, or fourth light emitting elements 410, 420, 430, or 440.

For example, the sensor 100 may be configured to absorb the light emitted from the first, second, or third light emitting elements 410, 420, and 430 configured to emit light of a green wavelength spectrum and then reflected by the recognition target 40, and to convert it into an electrical signal, or the sensor 100 may be configured to absorb the light emitted from the fourth light emitting element 440 configured to emit light of the infrared wavelength spectrum and then reflected by the recognition target 40, and to convert it into an electrical signal, but is not limited thereto. The sensor-embedded display panel 1000 according to the present example includes the fourth light emitting element 440 configured to emit light in the infrared wavelength spectrum and the sensor 100 configured to absorb light in the infrared wavelength spectrum. Therefore, in addition to the biometric detection function, the sensitivity of the sensor 100 may be improved even in a low-illumination environment, and the detection capability of a 3D image may be further increased by widening a dynamic range for detailed division of black and white contrast. Accordingly, the sensing capability of the sensor-embedded display panel 1000 may be further improved. In particular, since light in the infrared wavelength spectrum may have a deeper penetration depth due to its long wavelength characteristics and information located at different distances may be effectively obtained, images or changes in blood vessels such as veins, iris and/or face, etc., in addition to fingerprints may be effectively detected, and the scope of application nay be further expanded.

The aforementioned sensor-embedded display panel 1000 may be applied to (e.g., included in) electronic devices such as various display devices. Electronic devices such as display devices may be applied to, for example, mobile phones, video phones, smart phones, mobile phones, smart pads, smart watches, digital cameras, tablet PCs, laptop PCs, notebook computers, computer monitors, wearable computers, televisions, digital broadcasting terminals, e-books, personal digital assistants (PDAs), portable multimedia player (PMP), enterprise digital assistant (EDA), head mounted display (HMD), vehicle navigation, Internet of Things (IoT), Internet of all things (IoE), drones, door locks, safes, automatic teller machines (ATM), security devices, medical devices, or automotive electronic components, but are not limited thereto.

Figure 12:
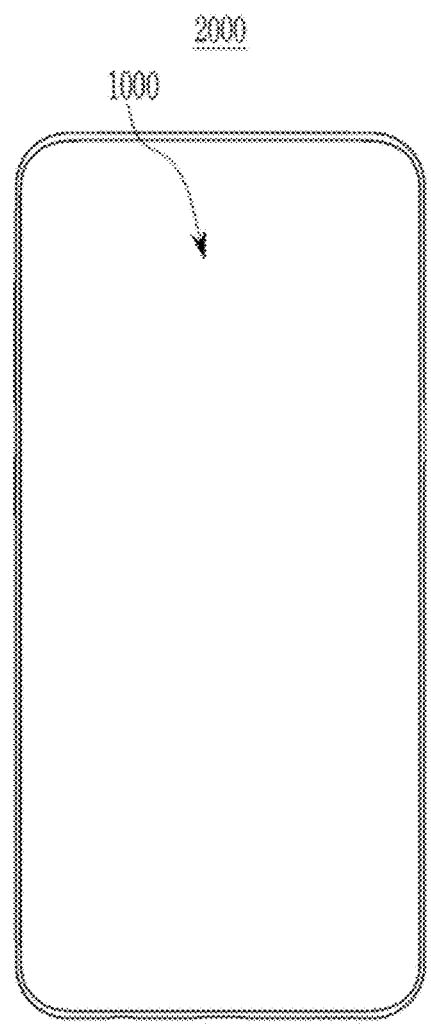
FIG. 12 is a schematic diagram illustrating an example of a smart phone as an electronic device according to some example embodiments.

FIG. 12 is a schematic view illustrating an example of a smart phone as an electronic device according to some example embodiments.

Referring to FIG. 12, the electronic device 2000 may include the aforementioned sensor-embedded display panel 1000, and the sensor 100 on the whole or a part of the sensor-embedded display panel 1000, and thus a biometric recognition function may be performed on any part of the screen, and according to the user's selection, the biometric recognition function may be selectively performed only at a specific location where the biometric recognition function is required.

An example of a method of recognizing the recognition target 40 in an electronic device 2000 such as a display device may include, for example, driving the first, second, and third light emitting elements 410, 420, and 430 of the sensor-embedded display panel 1000 (or the first, second, third, and fourth light emitting elements 410, 420, 430, and 440) and the sensor 100 to detect the light reflected from the recognition target 40 among the light emitted from the first, second, and third light emitting elements 410, 420, and 430 (or the first, second, third and fourth light emitting element 410, 420, 430, and 440), in the sensor 100; comparing the image of the recognition target 40 stored in advance with the image of the recognition target 40 detected by the sensor 100; and judging the consistency of the compared images and if they match according to the determination that recognition of the recognition target 40 is complete, turning off the sensor 100, permitting user's access to the display device, and driving the sensor-embedded display panel 1000 to display an image.

Figure 13:
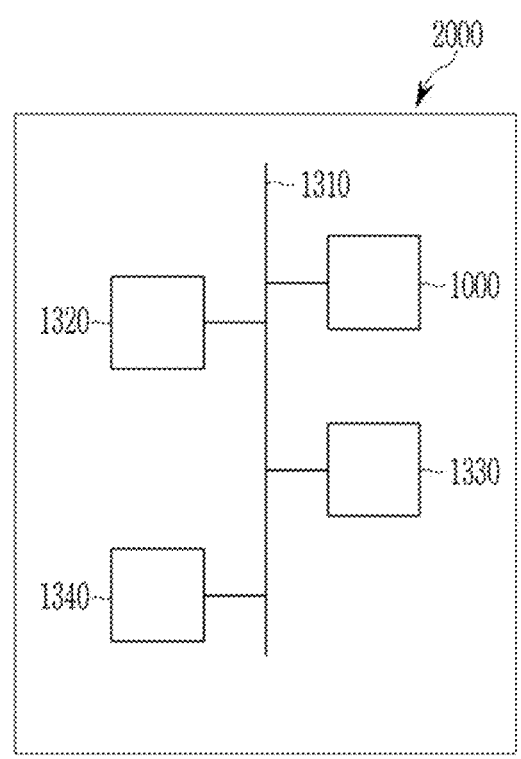
FIG. 13 is a schematic diagram illustrating an example of a configuration diagram of an electronic device according to some example embodiments.

FIG. 13 is a schematic view illustrating an example of a configuration diagram of an electronic device according to some example embodiments.

Referring to FIG. 13, in addition to the aforementioned constituent elements (e.g., the sensor-embedded display panel 1000), the electronic device 2000 may further include a bus 1310, a processor 1320, a memory 1330, and at least one additional device 1340. Information of the aforementioned sensor-embedded display panel 1000, processor 1320, memory 1330, and at least one additional device 1340 may be transmitted to each other through the bus 1310. In some example embodiments, the at least one additional device 1340 may be omitted. In some example embodiments, the sensor-embedded display panel 1000 may be replaced by a display device including, for example, exclusively light emitting elements and no light absorption sensors, while the at least one additional device 1340 may include one or a plurality (e.g., an array) of photosensors according to any of the example embodiments which may serve as a biometric sensor, a camera, or the like.

The processor 1320 may include one or more articles of processing circuitry such as a hardware including logic circuits; a hardware/software combination such as processor-implemented software; or any combination thereof. For example, the processing circuitry may be a central processing unit (CPU), an arithmetic logic unit (ALU), a digital signal processor, a microcomputer, a field programmable gate array (FPGA), System-on-Chip (SoC), a programmable logic unit, a microprocessor, an application-specific integrated circuit (ASIC), and the like. As an example, the processing circuitry may include a non-transitory computer readable storage device. The processor 1320 may control, for example, a display operation of the sensor-embedded display panel 1000 or a sensor operation of the sensor 100.

The memory 1330 may be a non-transitory computer readable storage medium, such as, for example, as a solid state drive (SSD) and may store an instruction program (e.g., program of instructions), and the processor 1320 may perform a function related to the sensor-embedded display panel 1000 by executing the stored instruction program.

The at least one additional device 1340 may include one or more communication interfaces (e.g., wireless communication interfaces, wired interfaces), user interfaces (e.g., keyboard, mouse, buttons, etc.), power supply and/or power supply interfaces, or any combination thereof.

The units and/or modules described herein may be implemented using hardware constituent elements and software constituent elements. The units and/or modules described herein may include, may be included in, and/or may be implemented by one or more articles of processing circuitry such as a hardware including logic circuits; a hardware/software combination such as processor-implemented software; or any combination thereof. For example, the processing circuitry may be a central processing unit (CPU), an arithmetic logic unit (ALU), a digital signal processor, a microcomputer, a field programmable gate array (FPGA), System-on-Chip (SoC), a programmable logic unit, a microprocessor, an application-specific integrated circuit (ASIC), and the like. For example, the hardware constituent elements may include microphones, amplifiers, band pass filters, audio-to-digital converters, and processing devices. The processing device may be implemented using one or more hardware devices configured to perform and/or execute program code by performing arithmetic, logic, and input/output operations. The processing device may include a processor, a controller and an arithmetic logic unit, a digital signal processor, a microcomputer, a field programmable array, a programmable logic unit, a microprocessor, or any other device capable of responding to and executing instructions. The processing device may access, store, operate, process, and generate data in response to execution of an operating system (OS) and one or more software running on the operating system.

The software may include a computer program, a code, an instruction, or any combination thereof, and may transform a processing device for a special purpose by instructing and/or configuring the processing device independently or collectively to operate as desired. The software and data may be implemented permanently or temporarily as signal waves capable of providing or interpreting instructions or data to machines, parts, physical or virtual equipment, computer storage media or devices, or processing devices. The software may also be distributed over networked computer systems so that the software may be stored and executed in a distributed manner. The software and data may be stored by one or more non-transitory computer readable storage devices.

The method according to the foregoing embodiments may be recorded in a non-transitory computer readable storage device including program instructions for implementing various operations of some example embodiments. The storage device may also include program instructions, data files, data structures, and the like alone or in combination. The program instructions recorded in the storage device may be specially designed for some example embodiments or may be known to those skilled in computer software and available for use. Examples of non-transitory computer-readable storage devices may include magnetic media such as hard disks, floppy disks, and magnetic tapes; optical media such as CD-ROM discs, DVDs and/or blue-ray discs; magneto-optical media such as optical disks; and a hardware device configured to store and execute program instructions such as ROM, RAM, flash memory, and the like. The aforementioned device may be configured to operate as one or more software modules to perform the operations of some example embodiments.

Hereinafter, some example embodiments are illustrated in more detail with reference to examples. However, the inventive concepts are not limited to these examples.

Synthesis Example I: Synthesis of p-Type Semiconductor

Synthesis Example 1

[Compound 1]

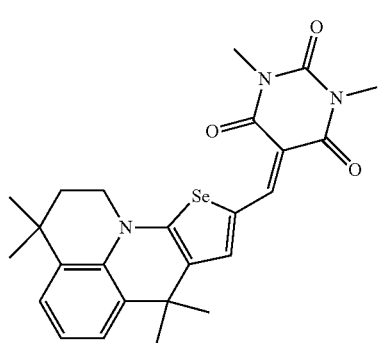

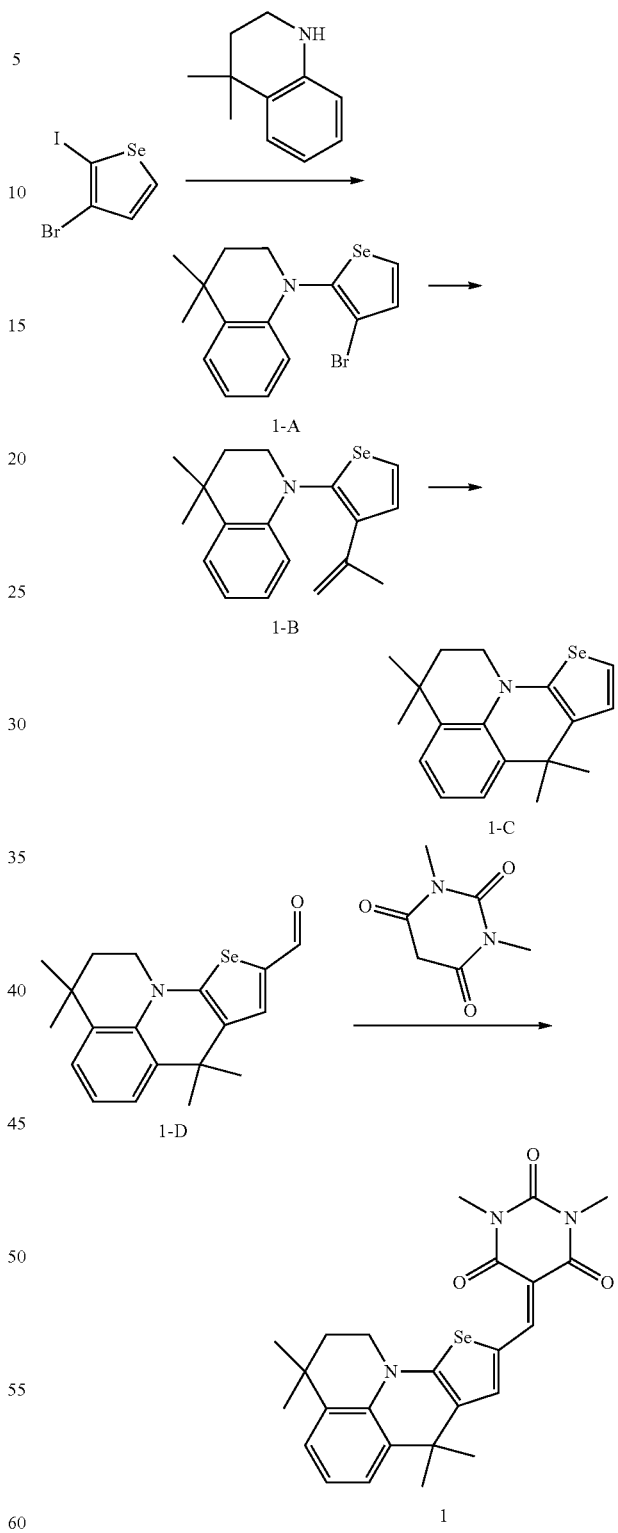

(i) Synthesis of Compound 1-A 10.0 g (62.0 mmol) of 4,4-dimethyl-1,2,3,4-tetrahydroquinoline, 3.57 g (6.20 mmol) of bis(dibenzylideneacetone)

palladium (Pd(dba)₂), 7.18 g (12.4 mmol) of Xantphos, 60.6 g (186 mmol) of cesium carbonate (Cs₂CO₃), and 200 ml of toluene are transferred to a round-bottomed flask. Subsequently, 25.0 g (74.4 mmol) of 3-bromo-2-iodoselenophene is added thereto and then, stirred at 100° C. for 12 hours. Then, a product therefrom is filtered with Celite, and a filtrate therefrom is concentrated and then, separated and purified through silica gel column chromatography (n-hexane:dichloromethane=19:1 (v/v)), obtaining 12.0 g of Compound 1-A (Yield: 52%).

(ii) Synthesis of Compound 1-B 9.00 g (24.4 mmol) of Compound 1-A, 0.55 g (2.4 mmol) of palladium(II)acetate (Pd(OAc)₂), 2.00 g (4.88 mmol) of Sphos, and 15.5 g (73.1 mmol) of potassium phosphate are transferred to a round-bottomed flask and then, dissolved in 1,4-dioxane:water (H₂O)=9:1 (v/v). Subsequently, 9.21 ml (48.8 mmol) of isopropenylboronic acid pinacol ester is added thereto and then, stirred at 100° C. for 12 hours. Then, a product therefrom is washed with a sodium chloride aqueous solution, extracted with ethyl acetate, and dried by adding anhydrous magnesium sulfate thereto. The obtained product is separated and purified through silica gel column chromatography (hexane:dichloromethane=1:9 (v/v)), obtaining 7.0 g of Compound 1-B (Yield: 87%).

(iii) Synthesis of Compound 1-C 5.00 g (15.1 mmol) of Compound 1-B is dissolved in 300 ml of toluene. Subsequently, 9.7 ml (150 mmol) of methanesulfonic acid is added dropwise thereto and then, stirred for 12 hours. The obtained product is poured into ice water and then, neutralized by adding a 2 M sodium hydroxide aqueous solution thereto, and an organic layer extracted with toluene therefrom is washed with a sodium chloride aqueous solution. The organic layer is dried by adding anhydrous magnesium sulfate thereto and then, concentrated through silica gel column chromatography (hexane:dichloromethane=9:1 (v/v)), obtaining 2.6 g of Compound 1-C (Yield: 52%).

(iv) Synthesis of Compound 1-D 1.3 ml (13 mmol) of phosphoryl chloride is added dropwise to 3.4 ml (44 mmol) of N,N-dimethyl formamide at 0° C. and then, stirred at room temperature for 2 hours. This solution is slowly dropped to a solution prepared by dissolving 2.6 g (6.9 mmol) of Compound 1-C in 70 ml of dichloromethane at 0° C. and then, stirred at room temperature for 1 hour. Subsequently, after adding water to a product obtained therefrom, a 2 M sodium hydroxide aqueous solution is added thereto until pH becomes 14 and then, stirred at room temperature for 2 hours. Then, an organic layer extracted therefrom with dichloromethane is washed with a sodium chloride aqueous solution, dried by adding anhydrous magnesium sulfate thereto, and concentrated. A product obtained therefrom is separated and purified through silica gel column chromatography (by changing a volume ratio of hexane:dichloromethane=3:2 (v/v) to 100% of dichloromethane), obtaining 2.4 g of Compound 1-D (Yield: 97%).

(v) Synthesis of Compound 1

1.00 g (2.79 mmol) of Compound 1-D is dissolved in 150 ml of ethanol, and 0.48 g (3.07 mmol) of 1,3-dimethylbarbituric acid is added thereto and then, stirred at 50° C. for 12 hours and concentrated under a reduced pressure. Subsequently, the reactant is dissolved in chloroform and silica-filtered. Herein, the obtained filtrate is concentrated and recrystallized with chloroform and ethanol, obtaining 1.20 g of Compound 1 (Yield: 87%). Compound 1 obtained therefrom is purified through sublimation up to 99.9%.

¹H-NMR (500 MHz, CD₂Cl₂): δ 8.43 (s, 1H), 7.98 (s, 1H), 7.30 (d, 1H), 7.26 (d, 1H), 7.10 (t, 1H), 3.86 (t, 2H), 3.33 (s, 6H), 2.03 (t, 2H), 1.60 (s, 6H), 1.37 (s, 6H).

Synthesis Example 2

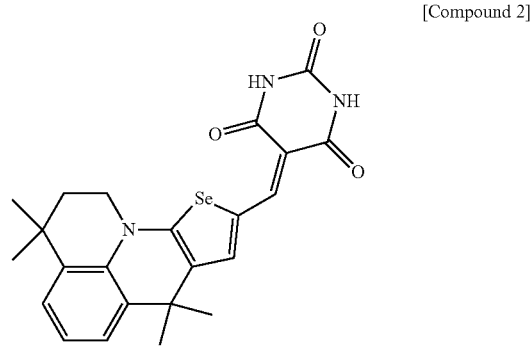 [SMILES: CC1(C)CCN2c3[se]c(C=C4C(=O)NC(=O)NC4=O)cc3C(C)(C)c3cccc1c32]

[Compound 2]

In the step (v) of Synthesis Example 1, 0.95 g of Compound 2 (Yield: 81%) is obtained in the same manner as Synthesis Example 1 except that barbituric acid is used instead of the 1,3-dimethylbarbituric acid. Compound 2 obtained therefrom is purified through sublimation up to purity of 99.9%.

¹H-NMR (500 MHz, CD₂Cl₂): δ 8.33 (s, 1H), 7.98 (s, 1H), 7.61 (s, 1H), 7.51 (s, 1H), 7.30 (d, 1H), 7.28 (d, 1H), 7.12 (t, 1H), 3.86 (t, 2H), 2.03 (t, 2H), 1.60 (s, 6H), 1.37 (s, 6H).

Synthesis Example 3

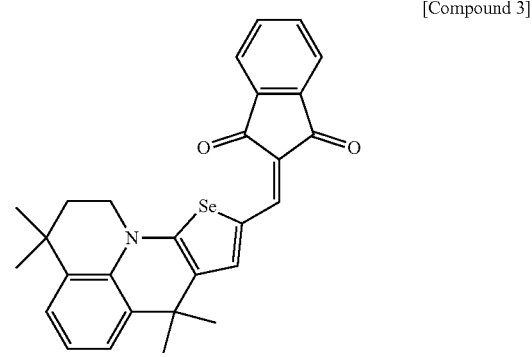 [SMILES: CC1(C)CCN2c3[se]c(C=C4C(=O)c5ccccc5C4=O)cc3C(C)(C)c3cccc1c32]

[Compound 3]

In the step (v) of Synthesis Example 1, 1.05 g of Compound 3 (Yield: 77%) is synthesized in the same manner as Synthesis Example 1 except that 1H-indene-1,3(2H)-dione is used instead of the 1,3-dimethylbarbituric acid. Compound 3 obtained therefrom is purified through sublimation up to purity of 99.9%. ¹H-NMR (500 MHz, CD₂Cl₂): δ 7.91 (s, 1H), 7.84 (s, 1H), 7.77-7.75 (m, 2H), 7.66-7.64 (m, 2H), 7.30 (d, 1H), 7.26 (d, 1H), 7.10 (t, 1H), 3.88 (t, 2H), 2.04 (t, 2H), 1.60 (s, 6H), 1.38 (s, 6H).

Synthesis Example 4

[Compound 4]

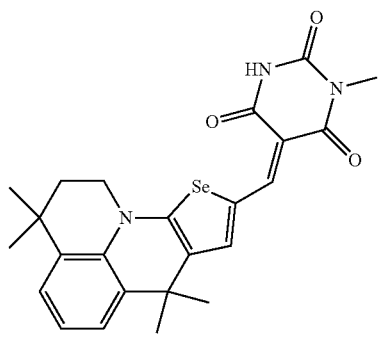

In the step (v) of Synthesis Example 1, 0.98 g of Compound 4 (Yield: 81%) is synthesized in the same manner as Synthesis Example 1 except that 1-methylbarbituric acid is used instead of the 1,3-dimethylbarbituric acid. Compound 4 obtained therefrom is purified through sublimation up to purity of 99.9%. $^1$H-NMR (500 MHz, CD$_2$Cl$_2$): δ 8.33 (s, 1H), 7.98 (s, 1H), 7.62 (s, 1H), 7.30 (d, 1H), 7.28 (d, 1H), 7.12 (t, 1H), 3.86 (t, 2H), 3.62 (s, 3H), 2.03 (t, 2H), 1.60 (s, 6H), 1.37 (s, 6H).

Synthesis Example 5

[Compound 5]

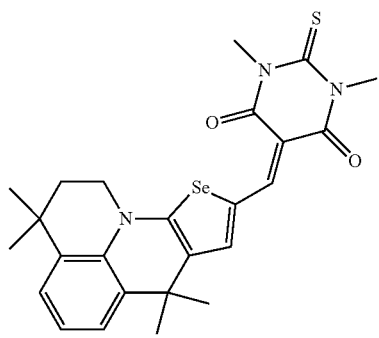

In the step (v) of Synthesis Example 1, 1.25 g of Compound 5 (Yield: 82%) is synthesized in the same manner as Synthesis Example 1 except that 1,3-dimethyl-2-thiobarbituric acid is used instead of the 1,3-dimethyl barbituric acid. Compound 5 obtained therefrom is purified through sublimation up to purity of 99.9%. $^1$H-NMR (500 MHz, CD$_2$Cl$_2$): δ 8.43 (s, 1H), 7.98 (s, 1H), 7.30 (d, 1H), 7.26 (d, 1H), 7.10 (t, 1H), 3.86 (t, 2H), 3.53 (s, 6H), 2.03 (t, 2H), 1.60 (s, 6H), 1.37 (s, 6H).

Synthesis Example 6

[Compound 6]

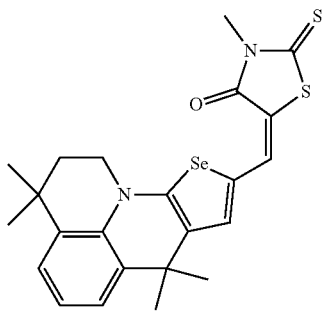

In the step (v) of Synthesis Example 1, 0.98 g of Compound 6 (Yield: 80%) is synthesized in the same manner as Synthesis Example 1 except that 3-methyl-2-thioxothiazolidin-4-one is used instead of the 1,3-dimethylbarbituric acid. Compound 6 obtained therefrom is purified through sublimation up to purity of 99.9%. $^1$H-NMR (500 MHz, CD$_2$Cl$_2$): δ 7.98 (s, 1H), 7.30 (d, 1H), 7.26 (d, 1H), 7.10 (t, 1H), 6.96 (s, 1H), 3.86 (t, 2H), 3.54 (s, 3H), 2.03 (t, 2H), 1.60 (s, 6H), 1.37 (s, 6H).

Synthesis Example 11: Synthesis of n-Type Semiconductor

Synthesis Example 7

[Compound A]

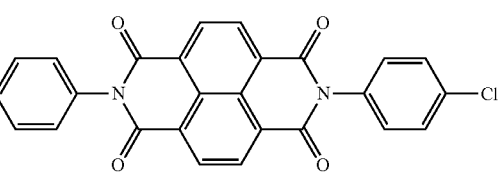

A mixture of 1,4,5,8-naphthalenetetracarboxylic dianhydride (1 eq.) and 4-chloroaniline (2.2 eq.) is dissolved in a dimethyl formamide (DMF) solvent and then, put in a two-necked and round-bottomed flask and stirred at 180° C. for 24 hours. Subsequently, after decreasing the temperature to room temperature, methanol is added thereto to precipitate a product and then, filtered, obtaining a powder-type material. Then, the material is several times washed with methanol and recrystallized for purification by using ethyl acetate and dimethylsulfoxide (DMSO). Subsequently, the obtained product is put in an oven and dried under vacuum at 80° C. for 24 hours, obtaining Compound A. A yield thereof is 50% or more. $^1$H-NMR (300 MHz, CDCl$_3$ with Hexafluoroisopropanol): δ=8.85 (s, 4H), 7.63 (s, 4H), 7.60 (s, 4H).

Evaluation I

The compounds obtained in Synthesis Examples are respectively deposited on a glass substrate, and the deposited thin films are evaluated with respect to energy levels.

A HOMO energy level is evaluated by irradiating UV light to the thin films with AC-2 (Hitachi) or AC-3 (Riken Keiki Co., Ltd.) and measuring an amount of photoelectrons emitted according to energy. A LUMO energy level may be calculated by obtaining a bandgap energy with a UV-Vis spectrometer (Shimadzu Corporation) and then, using the bandgap energy and the HOMO energy level.

The results are shown i Tables 1 and 2.

TABLE 1

|  | HOMO (eV) | LUMO (eV) | Energy bandgap (eV) |
|---|---|---|---|
| Compound 1 | 5.25 | 3.15 | 2.10 |
| Compound 2 | 5.27 | 3.19 | 2.08 |
| Compound 3 | NA | NA | 1.96 |
| Compound 4 | 5.25 | 3.16 | 2.09 |
| Compound 6 | 5.57 | 3.60 | 1.97 |

* HOMO, LUMO: absolute value

TABLE 2

|  | HOMO (eV) | LUMO (eV) | Energy bandgap (eV) |
|---|---|---|---|
| Compound A | 6.19 | 3.20 | 2.99 |

* HOMO, LUMO: absolute value

Evaluation II

The compounds according to Synthesis Examples are evaluated with respect to a sublimation temperature.

The sublimation temperature is evaluated through a thermogravimetric analysis (TGA) by increasing a temperature under a high vacuum degree of 10 Pa or less to check a temperature at which a weight of a sample decreases by 10% from the initial weight.

The results are shown in Tables 3 and 4.

TABLE 3

|  | $T_s$ (10, °C.) |
|---|---|
| Compound 1 | 208 |
| Compound 2 | 263 |
| Compound 3 | 225 |
| Compound 4 | 237 |
| Compound 5 | 225 |
| Compound 6 | 197 |

* Ts (10) (° C.): A temperature at which a weight of a sample decreases by 10% compared to its initial weight

TABLE 4

|  | $T_s$ (10, °C.) |
|---|---|
| Compound A | 270 |

* Ts (10) (°C): A temperature at which a weight of a sample decreases by 10% compared to its initial weight Example: Manufacture of Sensor I Example 1

ITO is deposited on a glass substrate to form a lower electrode. On the lower electrode, N,N'-bis(3-methylphenyl)-N,N'-diphenyl-[1,1-biphenyl]-4,4'-diamine is deposited to form a hole auxiliary layer (HOMO: 5.3 to 5.6 eV, LUMO: 2.0 to 2.3 eV). On the hole auxiliary layer, Compound 1 (p-type semiconductor) according to Synthesis Example 1 and fullerene (C60, n-type semiconductor) are co-deposited in a volume ratio (thickness ratio) of 1:1 to form a photoelectric conversion layer. Subsequently, on the photoelectric conversion layer, ITO is deposited to form an upper electrode, manufacturing a sensor.

Example 2

A sensor is manufactured in the same manner as Example 1 except that Compound 2 according to Synthesis Example 2 is used instead of Compound 1 according to Synthesis Example 1 to form a photoelectric conversion layer.

Example 3

A sensor is manufactured in the same manner as Example 1 except that Compound 3 according to Synthesis Example 3 is used instead of Compound 1 according to Synthesis Example 1 to form a photoelectric conversion layer.

Evaluation III

Light absorption characteristics and electrical properties of the sensors according to Examples are evaluated.

The light absorption characteristics are evaluated from a peak absorption wavelength $\lambda_{peak}$ and a full width at half maximum FWHM of an absorption spectrum.

The electrical properties are evaluated from external quantum efficiency EQE and a dark current under a reverse bias voltage. The EQE may be evaluated from EQE at a peak absorption wavelength λpeak with incident photon to current efficiency IPCE in blue (450 nm, B), green (λpeak, G), and red (630 nm, R) wavelengths at 3 V. The dark current is evaluated from dark current density obtained by measuring a dark current with a current-voltage evaluation equipment (Keithley K4200 parameter analyzer) and dividing it by a unit pixel area (0.04 cm$^2$), wherein the dark current density is evaluated from a current flowing when a reverse bias of −3 V is applied.

The results are shown in Table 5 and 6.

TABLE 5

|  | $\lambda_{peak}$ (nm) | FWHM (nm) |
|---|---|---|
| Example 1 | 530 | 103 |
| Example 2 | 535 | 114 |
| Example 3 | 565 | 98 |

TABLE 6

|  | EQE (@-3V, %) (B/G/R) | Dark current (h/s/μm$^2$) |
|---|---|---|
| Example 1 | 16/61/19 | 3.4 |
| Example 2 | 18/60/15 | — |
| Example 3 | 17/53/32 | — |

Referring to Tables 5 and 6, the sensors according to Examples exhibit high wavelength selectivity and improved photoelectric conversion efficiency in the green wavelength spectrum.

Example: Manufacture of Sensor II

Example 4

ITO is deposited on a glass substrate to form a lower electrode. Subsequently, on the lower electrode, N,N'-bis(3-methylphenyl)-N,N'-diphenyl-[1,1-biphenyl]-4,4'-diamine is deposited to form a hole auxiliary layer (HOMO: 5.3 to 5.6 eV, LUMO: 2.0 to 2.3 eV). On the hole auxiliary layer, Compound 1 according to Synthesis Example 1 is deposited to form a 10 nm-thick p-type semiconductor layer, and Compound A according to Synthesis Example 7 is deposited thereon to form a 5 nm-thick n-type semiconductor layer, forming a bi-layered photoelectric conversion layer. On the bi-layered photoelectric conversion layer, 4,7-diphenyl-1,10-phenanthroline is deposited to form an electron auxiliary layer (HOMO: 6.1 to 6.4 eV, LUMO: 2.9 to 3.2 eV). On the electron auxiliary layer, magnesium and silver are deposited to form a Mg:Ag upper electrode, manufacturing a sensor.

Example 5

A sensor is manufactured in the same manner as Example 4 except that Compound 2 according to Synthesis Example 2 is used instead of Compound 1 according to Synthesis Example 1 to form a p-type semiconductor layer.

Example 6

A sensor is manufactured in the same manner as Example 4 except that Compound 3 according to Synthesis Example 3 is used instead of Compound 1 according to Synthesis Example 1 to form a p-type semiconductor layer.

Evaluation IV

The sensors according to Examples are evaluated with respect to light absorption characteristics and electrical properties.

The light absorption characteristics are evaluated from a full width at half maximum FWHM of an absorption spectrum.

The electrical properties are evaluated from 1) maximum external quantum efficiency (EQEmax) when a reverse bias of 0 to −10 V is applied, 2) external quantum efficiency (EQE@−3 V, 85° C. 1 h) in wavelengths of 450 nm (blue, B), 530 nm (green, G) and 630 nm (red, R) when the sensors are annealed (allowed to stand at 85° C. for 1 hour), and a reverse bias of −3 V is applied thereto, and 3) dark current density obtained by dividing a dark current, which is measured with a current-voltage evaluation equipment (Keithley K4200 parameter analyzer) before and after annealing the sensors (allowed to stand at 85° C. for 1 hour), by a unit pixel area (0.04 cm$^2$). The dark current density is evaluated from a current flowing when the reverse bias of −3 V is applied.

The results are shown in Tables 7 to 9.

TABLE 7

|  | FWHM (nm) |
| --- | --- |
| Example 4 | 90 |
| Example 5 | 94 |
| Example 6 | 96 |

TABLE 8

|  | EQE$_{max}$ (%) | EQE (@-3V, 85° C., 1h, %) (B/G/R) |
| --- | --- | --- |
| Example 4 | 53.8 | 1.6/51.0/0.1 |
| Example 5 | 49.2 | 1.5/50.2/0.1 |
| Example 6 | 48.4 | 0.4/36.9/0.5 |

TABLE 9

|  | Dark current (mA/cm$^2$) | |
| --- | --- | --- |
|  | Before annealing | After annealing (85° C., 1 h) |
| Example 4 | 2.00 × 10$^{-6}$ | 2.40 × 10$^{-6}$ |
| Example 5 | 7.80 × 10$^{-5}$ | 2.40 × 10$^{-5}$ |
| Example 6 | 1.90 × 10$^{-4}$ | 4.80 × 10$^{-5}$ |

Referring to Tables 7 to 9, the sensors according to Examples exhibit high wavelength selectivity and good electrical properties.

While this inventive concepts have been described in connection with what is presently considered to be practical example embodiments, it is to be understood that the inventive concepts are not limited to such example embodiments. On the contrary, the inventive concepts are intended to cover various modifications and equivalent arrangements included within the spirit and scope of the appended claims.

What is claimed is:

1. A compound represented by Chemical Formula 1:

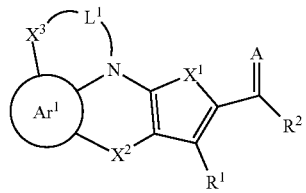

[Chemical Formula 1]

wherein, in Chemical Formula 1,

X$^1$ is Se, Te, SO, SO$_2$, NR$^a$, BR$^b$, CR$^c$R$^d$, SiR$^e$R$^f$, or GeR$^g$R$^h$,

Ar$^1$ is a substituted or unsubstituted C6 to C30 aromatic ring, a substituted or unsubstituted C2 to C30 heteroaromatic ring, or a fused ring thereof, X$^2$ and X$^3$ are each independently O, S, Se, Te, SO, SO$_2$, NR$^i$, BR$^j$, CR$^k$R$^l$, SiR$^m$R$^n$, or GeR$^o$R$^p$, L$^1$ is (CR$^3$R$^4$)$_n$ or R$^5$C═CR$^6$, wherein n is an integer of 1 to 3, A is a cyclic group including C═Z$^1$, a halogen, a C1 to C30 haloalkyl group, a cyano group, a dicyanovinyl group, or any combination thereof, wherein Z$^1$ is O, S, Se, Te, or CR$^q$R$^r$, R$^q$ and R$^r$ are each independently hydrogen, a substituted or unsubstituted C1 to C20 alkyl group, a carbonyl group, a cyano group, a dicyanovinyl group, or any combination thereof, and R$^q$ and R$^r$ are each independently present or linked to each other to form a ring, R$^1$ to R$^6$ and R$^a$ to R$^p$ are each independently hydrogen, a substituted or unsubstituted C1 to C20 alkyl group, a substituted or unsubstituted C2 to C30 alkenyl group, a substituted or unsubstituted C1 to C30 alkoxy group, a substituted or unsubstituted C1 to C30 alkylthio group, a substituted or unsubstituted C6 to C30 aryl group, a substituted or unsubstituted C3 to C30 heterocyclic group, a halogen, a cyano group, or any combination thereof, and R$^1$ to R$^6$ and R$^a$ to R$^p$ are each independently present or adjacent two of R$^1$ to R$^6$ and R$^a$ to R$^p$ are linked to each other to form a ring.

2. The compound of claim 1, wherein Ar$^1$ is a substituted or unsubstituted benzene, a substituted or unsubstituted naphthalene, a substituted or unsubstituted anthracene, a substituted or unsubstituted phenanthrene, a substituted or unsubstituted tetracene, a substituted or unsubstituted furan, a substituted or unsubstituted thiophene, a substituted or unsubstituted selenophene, a substituted or unsubstituted tellurophene, or a fused ring of two or more therefrom.

3. The compound of claim 1, wherein
at least one of $X^2$ or $X^3$ is $CR^kR^l$, $SiR^mR^n$, or $GeR^oR^p$, and $R^k$ to $R^p$ are each independently hydrogen, a substituted or unsubstituted C1 to C20 alkyl group, a substituted or unsubstituted C2 to C30 alkenyl group, a substituted or unsubstituted C1 to C30 alkoxy group, a substituted or unsubstituted C1 to C30 alkylthio group, a substituted or unsubstituted C6 to C30 aryl group, a substituted or unsubstituted C3 to C30 heterocyclic group, a halogen, a cyano group, or any combination thereof.

4. The compound of claim 1, wherein A is a cyclic group represented by any one of Chemical Formulas 1A to 1E:

[Chemical Formula 1A]

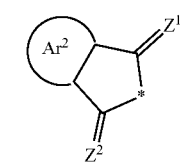

[Chemical Formula 1B]

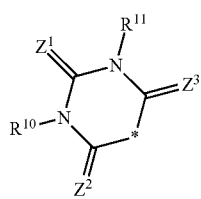

[Chemical Formula 1C]

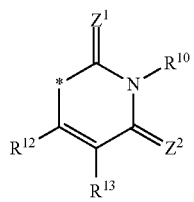

[Chemical Formula 1D]

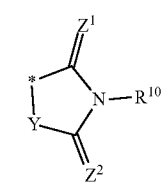

[Chemical Formula 1E]

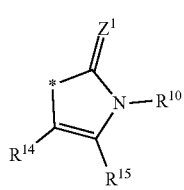

wherein, in Chemical Formulas 1A to 1E,
Ar$^2$ is a substituted or unsubstituted C6 to C30 arylene group, a substituted or unsubstituted C3 to C30 cycloalkylene group, a substituted or unsubstituted C3 to C30 cycloalkenylene group, a substituted or unsubstituted C2 to C30 heterocyclic group, or a fused ring thereof,
$Z^1$ to $Z^3$ are each independently O, S, Se, Te, or $CR^qR^r$, wherein $R^q$ and $R^r$ are each independently hydrogen, a substituted or unsubstituted C1 to C20 alkyl group, a carbonyl group, a cyano group, a dicyanovinyl group, or any combination thereof, and $R^q$ and $R^r$ are each independently present or linked to each other to form a ring, Y is O, S, Se, or Te, $R^{10}$ to $R^{15}$ are each independently hydrogen, a substituted or unsubstituted C1 to C20 alkyl group, a substituted or unsubstituted C2 to C30 alkenyl group, a substituted or unsubstituted C1 to C30 alkoxy group, a substituted or unsubstituted C1 to C30 alkylthio group, a substituted or unsubstituted C6 to C30 aryl group, a substituted or unsubstituted C3 to C30 heterocyclic group, a halogen, a cyano group, or any combination thereof, $R^{10}$ to $R^{15}$ are each independently present or adjacent two of $R^{10}$ to $R^{15}$ are linked to each other to form a ring, and

* is a linking point with Chemical Formula 1.

5. The compound of claim 4, wherein the cyclic group represented by Chemical Formula 1A is represented by any one of Chemical Formulas 1AA to 1AD:

[Chemical Formula 1AA]

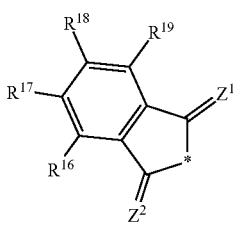

[Chemical Formula 1AB]

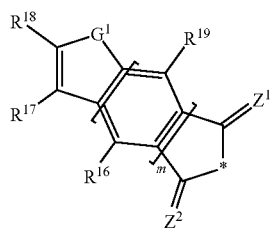

[Chemical Formula 1AC]

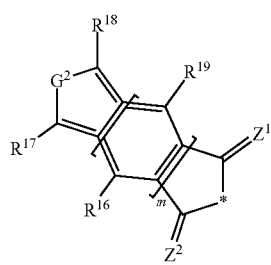

[Chemical Formula 1AD]

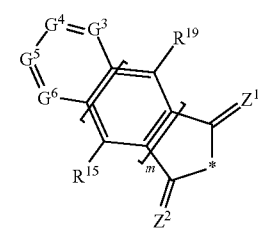

wherein, in Chemical Formulas 1AA to 1AD,
$Z^1$ and $Z^2$ are each independently O, S, Se, Te or $CR^qR^r$, wherein $R^q$ and $R^r$ are each independently hydrogen, a substituted or unsubstituted C1 to C20 alkyl group, a carbonyl group, a cyano group, a dicyanovinyl group, or any combination thereof, and $R^q$ and $R^r$ are each independently present or linked to each other to form a ring, $G^1$ and $G^2$ are each independently O, S, Se, or Te, $G^3$ to $G^6$ are each independently N or $CR^{20}$, $R^{16}$ to $R^{20}$ are each independently hydrogen, a substituted or unsubstituted C1 to C20 alkyl group, a substituted or unsubstituted C2 to C30 alkenyl group, a substituted or unsubstituted C1 to C30 alkoxy group, a substituted or unsubstituted C1 to C30 alkylthio group, a substituted or unsubstituted C6 to C30 aryl group, a substituted or unsubstituted C3 to C30 heterocyclic group, a halogen, a cyano group, or any combination thereof, $R^{16}$ to $R^{20}$ are each independently present or adjacent two of $R^{16}$ to $R^{20}$ are linked to each other to form a ring, m is an integer of 0 to 2, and

* is a linking point with Chemical Formula 1.

6. The compound of claim 1, wherein the compound is represented by Chemical Formula 2 or 3:

[Chemical Formula 2]

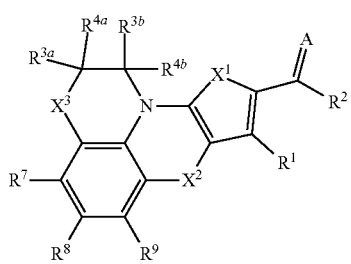

[Chemical Formula 3]

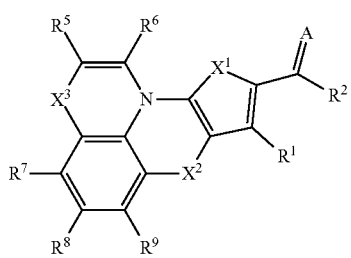

wherein, in Chemical Formula 2 or 3, $X^1$ is Se, Te, SO, $SO_2$, $NR^a$, $BR^b$, $CR^cR^d$, $SiR^eR^f$, or $GeR^gR^h$, $X^2$ and $X^3$ are each independently O, S, Se, Te, SO, $SO_2$, $NR^i$, $BR^j$, $CR^kR^l$, $SiR^mR^n$, or $GeR^oR^p$, A is a cyclic group including $C=Z^1$, a halogen, a C1 to C30 haloalkyl group, a cyano group, a dicyanovinyl group, or any combination thereof, wherein $Z^1$ is O, S, Se, Te, or $CR^qR^r$, $R^q$ and $R^r$ are each independently hydrogen, a substituted or unsubstituted C1 to C20 alkyl group, a carbonyl group, a cyano group, a dicyanovinyl group, or any combination thereof, and $R^q$ and $R^r$ are each independently present or linked to each other to form a ring, $R^1$, $R^2$, $R^{3a}$, $R^{3b}$, $R^{4a}$, $R^{4b}$, $R^5$ to $R^9$, and $R^a$ to $R^p$ are each independently hydrogen, a substituted or unsubstituted C1 to C20 alkyl group, a substituted or unsubstituted C2 to C30 alkenyl group, a substituted or unsubstituted C1 to C30 alkoxy group, a substituted or unsubstituted C1 to C30 alkylthio group, a substituted or unsubstituted C6 to C30 aryl group, a substituted or unsubstituted C3 to C30 heterocyclic group, a halogen, a cyano group, or any combination thereof, and $R^1$, $R^2$, $R^{3a}$, $R^{3b}$, $R^{4a}$, $R^{4b}$, $R^5$ to $R^9$, and $R^a$ to $R^p$ are each independently present or adjacent two of $R^1$, $R^2$, $R^{3a}$, $R^{3b}$, $R^{4a}$, $R^{4b}$, $R^5$ to $R^9$, and $R^a$ to $R^p$ are linked to each other to form a ring.

7. The compound of claim 1, wherein the compound is represented by any one of Chemical Formulas 1-1 to 1-5:

[Chemical Formula 1-1]

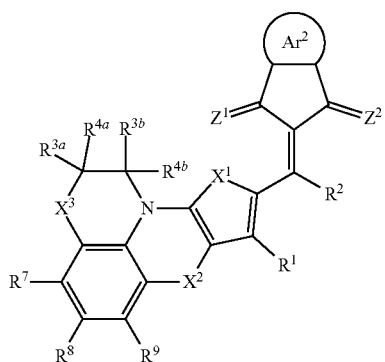

[Chemical Formula 1-2]

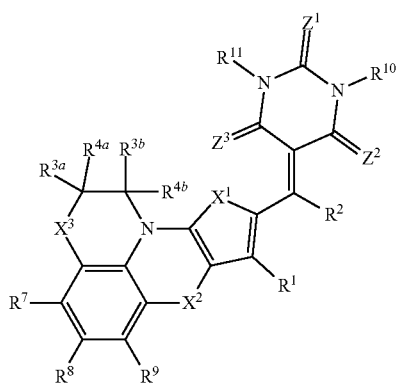

[Chemical Formula 1-3]

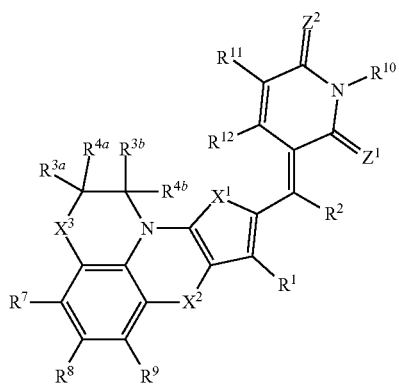

-continued

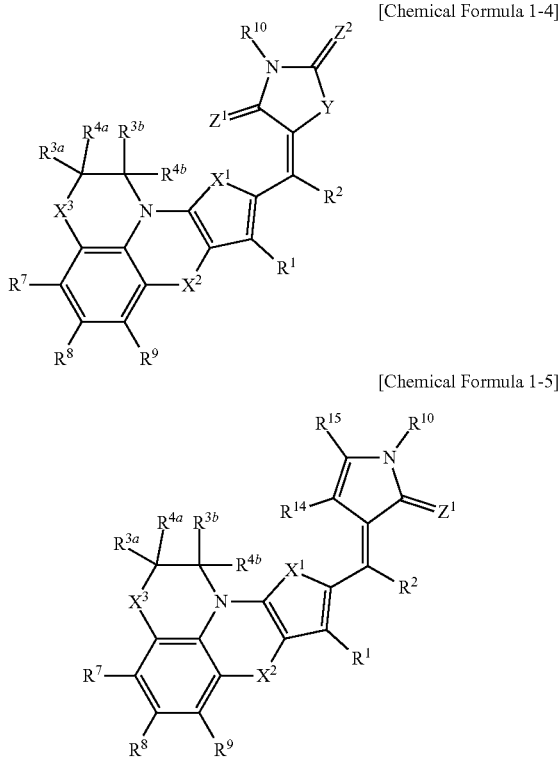

wherein, in Chemical Formulas 1-1 to 1-5, $X^1$ is Se, Te, SO, $SO_2$, $NR^a$, $BR^b$, $CR^cR^d$, $SiR^eR^f$, or $GeR^gR^h$, $X^2$ and $X^3$ are each independently O, S, Se, Te, SO, $SO_2$, $NR^i$, $BR^j$, $CR^kR^l$, $SiR^mR^n$, or $GeR^oR^p$, $Ar^2$ is a substituted or unsubstituted C6 to C30 arylene group, a substituted or unsubstituted C3 to C30 cycloalkylene group, a substituted or unsubstituted C3 to C30 cycloalkenylene group, a substituted or unsubstituted C2 to C30 heterocyclic group, or a fused ring thereof, $Z^1$ to $Z^3$ are each independently O, S, Se, Te or $CR^qR^r$, wherein $R^q$ and $R^r$ are each independently hydrogen, a substituted or unsubstituted C1 to C20 alkyl group, a carbonyl group, a cyano group, a dicyanovinyl group, or any combination thereof, and $R^q$ and $R^r$ are each independently present or linked to each other to form a ring, Y is O, S, Se, or Te, $R^1$, $R^2$, $R^{3a}$, $R^{3b}$, $R^{4a}$, $R^{4b}$, $R^7$ to $R^{15}$, and $R^a$ to $R^p$ are each independently hydrogen, a substituted or unsubstituted C1 to C20 alkyl group, a substituted or unsubstituted C2 to C30 alkenyl group, a substituted or unsubstituted C1 to C30 alkoxy group, a substituted or unsubstituted C1 to C30 alkylthio group, a substituted or unsubstituted C6 to C30 aryl group, a substituted or unsubstituted C3 to C30 heterocyclic group, a halogen, a cyano group, or any combination thereof, and $R^1$, $R^2$, $R^{3a}$, $R^{3b}$, $R^{4a}$, $R^{4b}$, $R^7$ to $R^{15}$, and $R^a$ to $R^p$ are each independently present or adjacent two of $R^1$, $R^2$, $R^{3a}$, $R^{3b}$, $R^{4a}$, $R^{4b}$, $R^7$ to $R^{15}$, and $R^a$ to $R^p$ are linked to each other to form a ring.

8. A sensor, comprising:
a first electrode;
a second electrode; and
a photoelectric conversion layer between the first electrode and the second electrode, the photoelectric conversion layer including the compound according to claim 1.

9. The sensor of claim 8, wherein
the compound is a p-type semiconductor, and
the photoelectric conversion layer further comprises an n-type semiconductor forming a pn junction with the compound.

10. A sensor-embedded display panel, comprising:
a substrate;
a light emitting element on the substrate, the light emitting element including a light emitting layer; and
a light absorption sensor on the substrate, the light absorption sensor including a photoelectric conversion layer,
wherein the light emitting element and the light absorption sensor are arranged in parallel along an in-plane direction of the substrate such that the light absorption sensor and the light emitting element at least partially overlap in the in-plane direction, and
the photoelectric conversion layer includes the compound of claim 1.

11. The sensor-embedded display panel of claim 10, wherein
the light emitting element comprises first, second, and third light emitting elements, the first, second, and third light emitting elements configured to emit light of different wavelength spectrum in relation to each other, and
the light absorption sensor is configured to absorb light that is emitted from at least one of the first, second, or third light emitting elements and then reflected by a recognition target, and convert the light into an electrical signal.

12. The sensor-embedded display panel of claim 10, wherein
the compound is a p-type semiconductor,
the photoelectric conversion layer further comprises an n-type semiconductor forming a pn junction with the compound, and
a difference between sublimation temperatures of the p-type semiconductor and the n-type semiconductor is less than or equal to 150° C., wherein each sublimation temperature of a given semiconductor of the p-type semiconductor or the n-type semiconductor is a temperature at which a weight loss of the given semiconductor of 10% compared to an initial weight of the given semiconductor occurs during thermogravimetric analysis of the given semiconductor at an ambient pressure of 10 Pa or less.

13. The sensor-embedded display panel of claim 12, wherein the sublimation temperatures of the p-type semiconductor and the n-type semiconductor are 100° C. to 380° C., respectively.

14. The sensor-embedded display panel of claim 12, wherein
the p-type semiconductor is a light absorbing material configured to absorb at least a portion of light in a visible light wavelength spectrum,
the n-type semiconductor is a transparent semiconductor configured not to substantially absorb light in the visible light wavelength spectrum.

15. The sensor-embedded display panel of claim 10, further comprising a common electrode, the common electrode is configured to apply a common voltage to the light emitting element and the light absorption sensor.

16. The sensor-embedded display panel of claim 15, further comprising:
  a first common auxiliary layer that is a single piece of material that extends continuously between the light emitting element and the common electrode and between the light absorption sensor and the common electrode, and
  a second common auxiliary layer that is another single piece of material that extends continuously between the light emitting element and the substrate and between the light absorption sensor and the substrate.

17. The sensor-embedded display panel of claim 10, wherein
  the sensor-embedded display panel comprises
    a display area configured to display a color, and
    a non-display area excluding the display area, and
  the light absorption sensor is in the non-display area.

18. The sensor-embedded display panel of claim 17, wherein
  the light emitting element comprises a first light emitting element configured to emit light of a red wavelength spectrum, a second light emitting element configured to emit light of a green wavelength spectrum, and a third light emitting element configured to emit light of a blue emission spectrum,
  the display area comprises
    a plurality of first subpixels configured to display red and comprising the first light emitting element,
    a plurality of second subpixels configured to display green and comprising the second light emitting element, and
    a plurality of third subpixels configured to display blue and comprising
  the third light emitting element, and
  the light absorption sensor is between at least two subpixels of a first subpixel of the plurality of first subpixels, a second subpixel of the plurality of second subpixels, or a third subpixel of the plurality of third subpixels.

19. An electronic device comprising the sensor of claim 8.

20. An electronic device comprising the sensor-embedded display panel of claim 10.

* * * * *